(12) United States Patent
Luk et al.

(10) Patent No.: US 9,150,788 B2
(45) Date of Patent: Oct. 6, 2015

(54) NON-AMPHIPHILE-BASED WATER-IN-WATER EMULSION AND USES THEREOF

(75) Inventors: Yan-Yeung Luk, Manlius, NY (US); Karen A. Simon, Syracuse, NY (US); Dacheng Ren, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 1578 days.

(21) Appl. No.: 12/233,337

(22) Filed: Sep. 18, 2008

(65) Prior Publication Data

US 2009/0269323 A1    Oct. 29, 2009

Related U.S. Application Data

(60) Provisional application No. 60/973,267, filed on Sep. 18, 2007.

(51) Int. Cl.
| | |
|---|---|
| *C09K 19/06* | (2006.01) |
| *A61K 38/43* | (2006.01) |
| *C12N 11/08* | (2006.01) |
| *C12P 21/06* | (2006.01) |
| *C09K 19/54* | (2006.01) |
| *A01N 25/04* | (2006.01) |
| *C07D 307/58* | (2006.01) |
| *C09K 19/02* | (2006.01) |
| *C09K 19/60* | (2006.01) |
| *C12N 11/04* | (2006.01) |

(52) U.S. Cl.
CPC .............. *C09K 19/544* (2013.01); *A01N 25/04* (2013.01); *C07D 307/58* (2013.01); *C09K 19/02* (2013.01); *C09K 19/06* (2013.01); *C09K 19/60* (2013.01); *C12N 11/04* (2013.01)

(58) Field of Classification Search
None
See application file for complete search history.

(56) References Cited

U.S. PATENT DOCUMENTS

| | | | |
|---|---|---|---|
| 7,365,184 B2 | 4/2008 | Jones et al. | |
| 7,420,024 B2 * | 9/2008 | Chu et al. | 527/300 |
| 7,824,732 B2 * | 11/2010 | Sahouani et al. | 427/213.3 |
| 2005/0042634 A1 | 2/2005 | Jones et al. | |
| 2007/0099249 A1 * | 5/2007 | Abbott et al. | 435/7.5 |
| 2008/0299153 A1 | 12/2008 | Jones et al. | |

FOREIGN PATENT DOCUMENTS

| | | | |
|---|---|---|---|
| WO | 2005/005598 A2 | | 1/2005 |
| WO | WO 2005/087201 | * | 9/2005 |

OTHER PUBLICATIONS

Duo et al., "New Brominated Furanones as Biofilm Inhibitors," Poster Presentation at the 107th American Society for Microbiology (ASM) General Meeting, Toronto, Canada (May 22, 2007).
Simon et al., "Water-in-Water Emulsions Stabilized by Non-Amphiphilic Interactions: Polymer-Dispersed Lyotropic Liquid Crystals," *Langmuir*, 23(3):1453-1458 (2007).

* cited by examiner

*Primary Examiner* — Sarae Bausch
(74) *Attorney, Agent, or Firm* — David L. Nocilly; George R. McGuire; Bond Schoeneck & King, PLLC

(57) ABSTRACT

The present invention relates to a non-amphiphile-based water-in-water emulsion composition. The non-amphiphile-based water-in-water emulsion composition includes a water-soluble polymer, a non-amphiphilic lyotropic mesogen encapsulated by the water-soluble polymer; and water. In one embodiment, the non-amphiphilic lyotropic mesogen includes, without limitation, a lyotropic chromonic liquid crystal, and more specifically disodium cromoglycate (DSCG). In another embodiment, the water-soluble polymer can include, without limitation, a polyacrylamide, a polyol, a polyvinylpyrrolidone, a polysaccharide, or a water-soluble fluoride-bearing polymer. The present invention also relates to a porous hydrogel made with the use of the non-amphiphile-based water-in-water emulsion. The present invention further relates to using the emulsion and hydrogel for various applications.

22 Claims, 28 Drawing Sheets

(preferred on pores of PAAm hydrogel)

ß-CD  Brominated
Furanone

SEQUENCE LISTING

<160> NUMBER OF SEQ ID NOS: 2

<210> SEQ ID NO 1
<211> LENGTH: 19
<212> TYPE: PRT
<213> ORGANISM: Pseudomonas aeruginosa

<400> SEQUENCE: 1

Asn Ala Cys Thr Ser Asp Gln Ser Pro Met Phe Ile Pro Lys Gly Cys
1               5                   10                  15

Ser Lys Cys

<210> SEQ ID NO 2
<211> LENGTH: 19
<212> TYPE: PRT
<213> ORGANISM: Pseudomonas aeruginosa -continued

<400> SEQUENCE: 2

Asn Lys Cys Thr Ser Asp Gln Asp Glu Gln Phe Ile Pro Lys Gly Cys
1               5                   10                  15

Ser Lys Cys

NON-AMPHIPHILE-BASED WATER-IN-WATER EMULSION AND USES THEREOF

CROSS-REFERENCE TO RELATED APPLICATIONS

This application claims priority under 35 U.S.C. §119 to U.S. Provisional Application No. 60/973,267, filed Sep. 18, 2007, which is herein incorporated by reference in its entirety.

GOVERNMENT RIGHTS STATEMENT

The present invention was made with U.S. Government support under National Science Foundation (NSF) Grant No. NSF-CMMI 0826288, NSF Grant No. NSF-CMMI 0727491, and Environmental Protection Agency Grant No. X-83232501-0. The U.S. Government has certain rights in the invention.

BACKGROUND OF THE INVENTION

1. Technical Field

The present invention generally relates to a non-amphiphile-based water-in-water emulsion composition and uses thereof.

2. Background Information

The use of surfactant materials has been known as early as 2,800 B.C. as evidenced by the discovery of soap-like materials in clay cylinders during the excavation of ancient Babylon (Routh, H. B et al., A. *Clin. Dermatol.* 1996, 14, (1), 3-6; Hunt, J. A., *The Pharm. J.* 1999, 263, (7076), 985-989). Since then, the science of emulsions has been believed to depend on the existence of amphiphilic molecules in a solution—where the aliphatic part of the molecule is excluded from water to either self-assemble into different aggregate structures or to solvate hydrophobic molecules into a dispersion of oily materials in water (Routh, H. B et al., A. *Clin. Dermatol.* 1996, 14, (1), 3-6).

Colloidal and interfacial sciences are rapidly merging with advances in soft and condensed matter physics as well as with biological phenomena at interfaces (Terentjev, E. M., *Europhys. Lett.* 1995, 32, (7), 607-12; Weitz, D. A., *Nature* 2001, 410, (6824), 32-33). The impact of liquid crystalline materials on the structure of emulsions is striking for both water-in-oil and oil-in-water emulsions (Tixier, T. et al., *Langmuir* 2006, 22, (5), 2365-2370). For instance, Poulin and Weitz have reported a linear ordering of water droplets in an anisotropic medium of nematic liquid crystal (Poulin, P. et al., *Science* 1997, 275, (5307), 1770-1773). This order is believed to arise from a delicate balance between the stabilization of the emulsion by surfactants and the anisotropic forces exerted by the liquid crystals (Poulin, P. et al., *Science* 1997, 275, (5307), 1770-1773; Drzaic, P. S., *Liquid Crystal Dispersions*. Wiley-Interscience: Singapore, 1995, Vol. 1; Poulin, P. et al., *Phys. Rev. E: Stat. Phys. Plasmas, Fluids,* 1998, 57, (1), 626-637). Seminal work on liquid crystal droplets dispersed in water (oil-in-water) was also done by Lavrentovich and coworkers (Lavrentovich, O. D. et al., *Phys. Rev. E: Stat. Phys. Plasmas, Fluids,* 1998, 57, (6), R6269-R6272; Volovik, G. E. et al., *JETP Lett.* 1983, 58, 1159-1167). Some applications for nematic liquid crystal droplets dispersed in a polymer solution were also developed for switchable windows and light valves (Doane, J. W. et al., *Macromol. Symp.* 1995, 96, (International Conference on Liquid Crystal Polymers, 1994), 51-60; Fernandez-Nieves, A. et al., *Phys. Rev. Lett.* 2004, 92, (10), 105503/1-105503/4).

Many phenomena observed at the aqueous interface between a surface and a biological entity such as a protein or a whole mammalian cell are far more complicated than merely simple hydrophobic/hydrophobic interactions (Luk, Y.-Y. et al., *Chem. Mater.* 2005, 17, (19), 4774-4782; Luk, Y.-Y. et al., *Langmuir* 2000, 16, (24), 9604-9608). For instance, proteins adsorb and mammalian cells adhere to most surfaces that can be both hydrophobic and hydrophilic (Luk, Y.-Y. et al., *Langmuir* 2000, 16, (24), 9604-9608; Kane, R. et al., *Langmuir* 2003, 19, (6), 2388-2391). Multiple chemistries and mechanisms have been proposed to control the adsorption of proteins and adhesion of cells on surfaces (Kane, R. S. et al., *Langmuir* 2003, 19, (6), 2388-2391; Arakawa, T. et al., *Seikagaku* 1982, 54, (11), 1255-9; Arakawa, T. et al., *Biochem.* 1982, 21, (25), 6536-44; Arakawa, T. et al., *Biochem.* 1985, 24, (24), 6756-62). Nature uses sophisticated molecular forces to assemble complex and uniquely folded structures (Berg, J. M. et al., *Biochemistry.* 6 ed., W.H. Freeman Company: New York, 2006, p 1120). For example, the base stacking and hydrogen bonding of nucleic acids give rise to the structured double-stranded helix of DNA even though water can compete with the hydrogen bonding between the base pairs (Crothers, D. M. et al., *Nucleic Acids: Structures, Properties, and Functions*. University Science Books: Sausalito, Calif., 2000; p 808). A folded protein excludes most of the water from the interior of a folded structure while maintaining the polar amino acid residues in the active site (Creighton, T., *Proteins: Structures and Molecular Properties.* 6 ed.; W.H. Freeman Company: New York, 1992; p 512).

Many methods have been developed to immobilize proteins on materials. For example, proteins have been immobilized on agarose (a galactose-based polyssacharide) (Spagna, G., R. N. Barbagallo, P. G. Pifferi, R. M. Blanco, and J. M. Guisan, Stabilization of a beta-glucosidase from *Aspergillus niger* by binding to an amine agarose gel. J. Mol. Catal. B: Enzym., 2000. 11(2-3): p. 63-69; Axen, R. and S. Ernback, Chemical fixation of enzymes to cyanogen halide activated polysaccharide carriers. European Journal of Biochemistry, 1971. 18(3): p. 351-60; Axen, R., J. Porath, and S. Ernback, Chemical coupling of peptides and proteins to polysaccharides by means of cyanogen halides. Nature, 1967. 214(5095): p. 1302-4; Hearn, M. T. W., 1,1'-Carbonyldiimidazole-mediated immobilization of enzymes and affinity ligands. Methods Enzymol. FIELD Full Journal Title: Methods in Enzymology, 1987. 135(Immobilized Enzymes Cells, Pt. B): p. 102-17; and Wei, Y., G. Ning, H.-Q. Zhang, J.-G. Wu, Y.-H. Wang, and K.-D. Wesche, Microarray preparation based on oxidation of agarose-gel and subsequent enzyme immunoassay. Sens. Actuators, B FIELD Full Journal Title: Sensors and Actuators, B: Chemical, 2004. B98(1): p. 83-91), polyacrylonitrile (PAN) membranes (Biondi, P. A., M. Pace, O. Brenna, and P. G. Pietta, Coupling of enzymes to polyacrylonitrile. Eur. J. Biochem., 1976. 61(1): p. 171-4; Godjevargova, T., R. Nenkova, and V. Konsulov, Immobilization of glucose oxidase by acrylonitrile copolymer coated silica supports. J. Mol. Catal. B: Enzym., 2006. 38(2): p. 59-64; Hicke, H.-G., P. Boehme, M. Becker, H. Schulze, and M. Ulbricht, Immobilization of enzymes onto modified polyacrylonitrile membranes: application of the acyl azide method. J. Appl. Polym. Sci., 1996. 60(8): p. 1147-61; Hunter, M. J. and M. L. Ludwig, The reaction of imidoesters with proteins and related small molecules. J. Am. Chem. Soc., 1962. 84: p. 3491-504), mesoporous silica (Chaudhary, Y. S., S. K. Manna, S. Mazumdar, and D. Khushalani, Protein encapsulation into mesoporous silica hosts. Microporous Mesoporous Mater., 2008. 109(1-3): p. 535-541; Vinu, A., N. Gokulakrishnan, T.

Mori, and K. Ariga, Immobilization of biomolecules on mesoporous structured materials. Bio-Inorg. Hybrid Nanomater., 2008: p. 113-157; Slowing, I. I., B. G. Trewyn, and V. S. Y. and F. Caruso, Bioinspired porous hybrid materials via layer-by-layer assembly. Bio-Inorg. Hybrid Nanomater., 2008: p. 209-238) via often multiple steps of chemical reactions. Some conjugation methods including disulfide (Carlsson, J., R. Axen, and T. Unge, Reversible, covalent immobilization of enzymes by thiol-disulfide interchange. Eur. J. Biochem., 1975. 59(2): p. 567-72; Ljungquist, C., B. Jansson, T. Moks, and M. Uhlen, Thiol-directed immobilization of recombinant IgG-binding receptors. Eur. J. Biochem. FIELD Full Journal Title: European Journal of Biochemistry, 1989. 186(3): p. 557-61) and imine (Spagna, G., R. N. Barbagallo, P. G. Pifferi, R. M. Blanco, and J. M. Guisan, Stabilization of a beta-glucosidase from *Aspergillus niger* by binding to an amine agarose gel. J. Mol. Catal. B: Enzym., 2000. 11(2-3): p. 63-69; Blanco, R. M. and J. M. Guisan, Protecting effect of competitive inhibitors during very intense insolubilized enzyme-activated support multipoint attachments: trypsin (amine)-agarose (aldehyde) system. Enzyme and Microbial Technology, 1988. 10(4): p. 227-32; Shainoff, J. R., Zonal immobilization of proteins. Biochemical and Biophysical Research Communications, 1980. 95(2): p. 690-5) bond formation between protein and solid support are reversible and unstable at certain pH, and thus are less desired methods. The locations of the immobilized protein in materials are often not controlled. Overall, these methods are primarily aimed for biotechnology purposes such as making the enzyme reusable and the product easily purified (Ong, E., J. M. Greenwood, N. R. Gilkes, D. G. Kilburn, R. C. Miller, Jr., and R. A. J. Warren, The cellulose-binding domains of cellulases: tools for biotechnology. Trends Biotechnol., 1989. 7(9): p. 239-43). However, there is a need for new ways of immobilizing proteins for a variety of uses.

Relative to the success in the semi-conductor and electronic industry, man-made materials with biological functions aimed for potential artificial cells and organ still fall embarrassingly far behind the powerful and sophisticated biological machinery such as enzymes, DNA transcription, protein synthesis or a whole organ such an eye or a heart. Several novel core-shell and sophisticated porous materials have been made by using colloidal and soft matter sciences (Jiang, P., J. F. Bertone, and V. L. Colvin, *A lost-wax approach to monodisperse colloids and their crystals.* Science (Washington, D.C., U.S.), 2001. 291(5503): p. 453-457; Utada, A. S., E. Lorenceau, D. R. Link, P. D. Kaplan, H. A. Stone, and D. A. Weitz, *Monodisperse Double Emulsions Generated from a Microcapillary Device.* Science (Washington, D.C., U.S.), 2005. 308(5721): p. 537-541; Kuykendall, D. W. and S. C. Zimmerman, *Nanoparticles: A very versatile nanocapsule.* Nat. Nanotechnol., 2007. 2(4): p. 201-202.). Others have used inorganic templates (Caruso, F., R. A. Caruso, and H. Moehwald, *Nanoengineering of inorganic and hybrid hollow spheres by colloidal templating.* Science, 1998. 282(5391): p. 1111-1114.). These studies have focused on building novel structures for applications such as drug delivery, but not on biocompatibility issues such as how the chemistry of materials influence the immobilized protein activities or how materials can be rationally engineered such that the immobilized protein will have superior catalytic activities. For artificial materials to mimic or surpass the functions in biological systems, materials must be made highly biocompatible for supporting the biological functions from immobilized proteins, and with structures that allow efficient transport of reagents in and out of the materials (FIG. 1).

An "emulsion" is generally known in the art as two immiscible liquids mixed together (by shaking for example) with small droplets of one liquid dispersed (i.e., separated and distributed throughout the space) in the other liquid. This dispersion is usually not stable and all the droplets will "clump" together over time and forms two layers. Because of the immiscibility, the emulsion is classified according to the chemical nature of the liquids. For example, an emulsion may be classified as an oil-in-water (O/W) emulsion (e.g., micelles), a water-in-oil (W/O) emulsion (e.g., inverted micelles), and sometimes such as water-in-oil-in-water (W/O/W). These classical types of emulsions can be stabilized from coalescence (i.e. preventing the droplets from clumping together) by the presence of surfactant molecules, of which part of the molecular structure is soluble in water, and the other part is soluble in oil-like solvents (see FIG. 2A).

One of the most general and paramount challenges for designing surfaces and materials that are in contact with biological fluids and living systems is biofouling at three different levels: protein adsorption (Wilson, C. J., R. E. Clegg, D. I. Leavesley, and M. J. Pearcy, Mediation of Biomaterial-Cell Interactions by Adsorbed Proteins: A Review. Tissue Engineering, 2005. 11(1/2): p. 1-18; Magnani, A., G. Peluso, S. Margarucci, and K. K. Chittur, Protein adsorption and cellular/tissue interactions. Integrated Biomaterials Science, 2002: p. 669-689; Mrksich, M. and G. M. Whitesides, Using self-assembled monolayers to understand the interactions of man-made surfaces with proteins and cells. Annual Review of Biophysics and Biomolecular Structure, 1996. 25: p. 55-78), mammalian cell adhesion (Mrksich, M., L. E. Dike, J. Tien, D. E. Ingber, and G. M. Whitesides, Using microcontact printing to pattern the attachment of mammalian cells to self-assembled monolayers of alkanethiolates on transparent films of gold and silver. Experimental Cell Research, 1997. 235(2): p. 305-313), and biofilm formation (Callow, J. A. and M. E. Callow, Biofilms. Progress in Molecular and Subcellular Biology, 2006. 42(Antifouling Compounds): p. 141-169; Coetser, S. E. and T. E. Cloete, Biofouling and biocorrosion in industrial water systems. Critical Reviews in Microbiology, 2005. 31(4): p. 213-232). These biofoulings cause a wide range of problems for the biomedical research, public health (Parsek, M. and P. Singh, Bacterial Biofilms: An Emerging Link to Disease Pathogenesis. Annual Review of Microbiology, 2003. 57: p. 677-701; Costerton, J. W., P. S. Stewart, and E. P. Greenberg, Bacterial biofilms: a common cause of persistent infections. Science, 1999. 284(5418): p. 1318-1322), and industry (Coetser, S. E. and T. E. Cloete, Biofouling and biocorrosion in industrial water systems. Critical Reviews in Microbiology, 2005. 31(4): p. 213-232; Cloete, T. E., Biofouling control in industrial water systems: what we know and what we need to know. Materials and Corrosion, 2003. 54(7): p. 520-526).

First, proteins adsorb to almost all types of surfaces, significantly compromising the effort to build multi-array protein assays that require proper orientation and non-denatured protein structure in a small area (Lee, Y.-S, and M. Mrksich, Protein chips, from concept to practice. Trends in Biotechnology, 2002. 20(12, Suppl.): p. S14-S18). Protein adsorption and mammalian cell adhesion are also the primary cause of undesired resistance to medical implants that result in inflammation and sometimes life threatening situations (Wilson, C. J., R. E. Clegg, D. I. Leavesley, and M. J. Pearcy, Mediation of Biomaterial-Cell Interactions by Adsorbed Proteins: A Review. Tissue Engineering, 2005. 11(1/2): p. 1-18; Magnani, A., G. Peluso, S. Margarucci, and K. K. Chittur, Protein adsorption and cellular/tissue interactions. Integrated Biomaterials Science, 2002: p. 669-689). Second, under conditions that support proliferation, most types of mammalian cells adhere to surfaces as an essential requirement for vitality. This adhesion also is also a primary source for the undesired immuno-resistance of medical implants (Wilson, C. J., R. E. Clegg, D. I. Leavesley, and M. J. Pearcy, Mediation of Biomaterial-Cell Interactions by Adsorbed Proteins: A Review. Tissue Engineering, 2005. 11(1/2): p. 1-18; Magnani, A., G. Peluso, S. Margarucci, and K. K. Chittur, Protein adsorption and cellular/tissue interactions. Integrated Biomaterials Science, 2002: p. 669-689; Brunette, D. M., Principles of cell behavior on titanium surfaces and their application to implanted devices. Titanium in Medicine, 2001: p. 485-512). Third, through a multi-step process, microbes (bacteria and fungi) form films of multicellular structures imbedded in a sticky polysaccharide matrix that strongly attaches to surfaces (Callow, J. A. and M. E. Callow, Biofilms. Progress in Molecular and Subcellular Biology, 2006. 42(Antifouling Compounds): p. 141-169). These biofilms cause a wide spectrum of health-related problems, including infections due to medical devices such as intravenous catheters, joint prostheses, cardiac pacemakers, prosthetic heart valves, peritoneal dialysis catheters and cerebrospinal fluid shunts (Parsek, M. and P. Singh, Bacterial Biofilms: An Emerging Link to Disease Pathogenesis. Annual Review of Microbiology, 2003. 57: p. 677-701; Costerton, J. W., P. S. Stewart, and E. P. Greenberg, Bacterial biofilms: a common cause of persistent infections. Science, 1999. 284(5418): p. 1318-1322). These biofilms also cause billions of dollars worth of damage in industries including enhanced corrosion of metallic materials and equipments (Coetser, S. E. and T. E. Cloete, Biofouling and biocorrosion in industrial water systems. Critical Reviews in Microbiology, 2005. 31(4): p. 213-232; Cloete, T. E., Biofouling control in industrial water systems: what we know and what we need to know. Materials and Corrosion, 2003. 54(7): p. 520-526).

Two challenges significantly hinder the development of methods to control biofouling. First, the mechanism of biofouling is not well-understood at molecular level. Although both mammalian cell adhesion and biofilm formation proceed with protein adsorption at the early stage of bio fouling, protein adsorption itself is a multi-step and complex process. There are mixed opinions and theories as to how a surface can resist protein adsorption. Thus, this challenge calls for a reevaluation of the current opinions and the development of new theories. It also requires an experimental system that can both test the new hypotheses and potentially achieve competent anti-fouling surfaces. Second, living organisms continuously sense, respond to (at genetic level) and modify their environments. Thus, even a competent anti-fouling surface may be compromised after prolonged exposure to biological fluids.

Thus, there is a need to work beyond the two-dimensional surfaces and consider a porous interfacial structure that can accommodate both chemical and biological changes over time. Further, a need exists for more advanced and efficient means to (i) study the effect of the chemistry of the gel material on enzymatic activity of immobilized proteins and (ii) tailor different microenvironments on the porous hydrogel for enabling the immobilized enzymes to have a higher catalytic activity than that of free enzymes in solution, (iii) provide a new one-pot method using water-in-water emulsion to make protein-immobilized hydrogel and (iv) introduce a hierarchy in the novel structures of hydrogel allowing preferred location of immobilized proteins.

The present invention is useful for overcoming the various deficiencies in the art.

SUMMARY OF THE INVENTION

Briefly, the present invention satisfies the need for an amphiphile-free emulsion, and enables applications that are unique to the use of such an emulsion.

In accordance with the above, it is an object of the present invention to describe a new water-in-water emulsion system that does not require amphiphilic molecules.

The present invention provides, in a first aspect, a non-amphiphile-based water-in-water emulsion composition. The non-amphiphile-based water-in-water emulsion composition includes a water-soluble polymer, a non-amphiphilic lyotropic mesogen encapsulated by the water-soluble polymer; and water. In one embodiment, the non-amphiphilic lyotropic mesogen includes, without limitation, a lyotropic chromonic liquid crystal, and more specifically disodium cromoglycate (DSCG). In another embodiment, the water-soluble polymer can include, without limitation, a polyacrylamide, a polyol, a polyvinylpyrrolidone, a polysaccharide, or a water-soluble fluoride-bearing polymer.

In a further embodiment, the non-amphiphile-based water-in-water emulsion composition can further include a protein. The protein can include, without limitation, an enzyme.

The present invention provides, in a second aspect, a porous hydrogel composition. The porous hydrogel composition includes a cross-linked water-soluble polymer network containing a plurality of pores. In one embodiment, the pores are produced by (i) encapsulating a non-amphiphilic lyotropic mesogen within a shell comprised of a cross-linked water-soluble polymer; and (ii) removing the non-amphiphilic lyotropic mesogen to form the pores. In another embodiment, the pores have an average pore diameter of about 5 µm to about 40 µm.

In a further embodiment, the porous hydrogel composition can further include a biocatalytic compound. The biocatalytic compound can be either covalently or non-covalently immobilized. In a particular embodiment, the biocatalytic compound can be, without limitation, any compound that is effective for inhibiting the formation of biofilm, detecting a target substance in an aqueous solution, or degrading a polysaccharide in solution. In a more particular embodiment, the biocatalytic compound can include a bromosubstituted furanone.

The present invention provides, in a third aspect, a method for forming a porous hydrogel composition. This method involves preparing a water-in-water emulsion composition that comprises at least one water-soluble monomer, a non-amphiphilic lyotropic mesogen, at least one modifier compound, and water. The water-soluble monomer is polymerized into a water-soluble polymer that encapsulates the non-amphiphilic lyotropic mesogen. The non-amphiphilic lyotropic mesogen is then removed from the water-soluble polymer, thereby forming the porous hydrogel composition.

The present invention provides, in a fourth aspect, a three-dimensional cell culture having a scaffold comprised of the porous hydrogel composition of the present invention.

The present invention provides, in a fifth aspect, a substrate that includes a layer formed on the substrate, where the layer comprises the porous hydrogel composition of the present invention.

The present invention provides, in a sixth aspect, a method for inhibiting biofilm formation. This method involves providing a surface that is susceptible to biofilm formation. The surface is then modified by introducing onto the surface the porous hydrogel composition of the present invention, where the hydrogel is effective to inhibit bio film formation on the surface.

The present invention provides, in a seventh aspect, a method for preparing a therapeutic compound. This method involves providing a precursor to a therapeutic compound. The precursor is contacted to the porous hydrogel composition of the present invention under conditions effective to form the therapeutic compound. In this aspect, the porous hydrogel composition further comprises a covalently immobilized enzyme that is effective to catalyze formation of the therapeutic compound from the precursor.

The present invention provides, in an eighth aspect, a method for modifying a protein biopharmaceutical compound. This method involves providing an unmodified protein biopharmaceutical compound that is subject to a desired modification. The unmodified protein biopharmaceutical compound is contacted to the porous hydrogel composition of the present invention under conditions effective to form a modified protein biopharmaceutical compound. In this aspect, the porous hydrogel composition further comprises a covalently immobilized enzyme that is effective to catalyze the desired modification of the unmodified protein biopharmaceutical compound.

The present invention provides, in a ninth aspect, a method for modifying a surface. This method involves providing a surface to be modified. The surface is coated with a porous hydrogel composition of the present invention, thereby modifying the surface so that the surface has the same functionality as the porous hydrogel composition.

The present invention provides, in a tenth aspect, a method of analyzing an aqueous solution for the presence of a target substance. This method involves providing a porous hydrogel composition of the present invention, where the porous hydrogel composition comprises an antibody that is effective for detecting the presence of a target substance. The porous hydrogel composition is contacted to an aqueous sample suspected of containing the target substance under conditions effective to produce a detection signal if the target substance is present. Thereafter, analysis is conducted to determine the presence of a detection signal output, where the presence of the detection signal indicates the presence of the target substance.

The present invention provides, in a eleventh aspect, a bromosubstituted furanone having a structure of the formula:

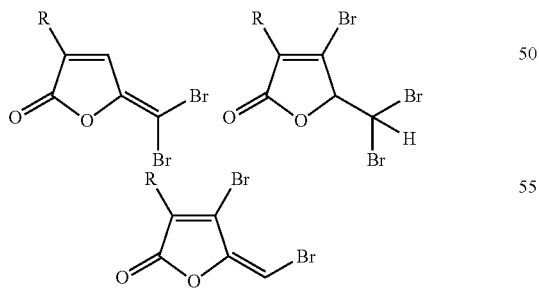

where R can include, without limitation, alkyl, aromatic rings, coumarin, cromolyn, or adamantane. These new bromosubstituted furanones of the present invention have been found to be effective in inhibiting biofilm formation.

More specifically, the bromosubstituted furanone has a structure, including, but not limited to, a structure of the following formulae:

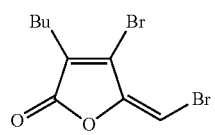 #1

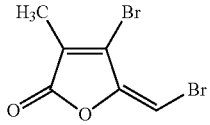 #8a

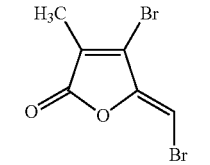 #8b

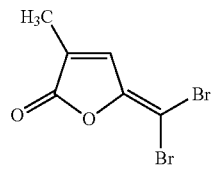 #9

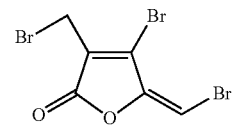 #10

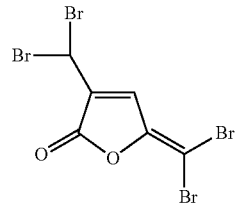 #11

11a

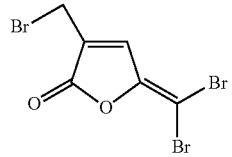 #12

13

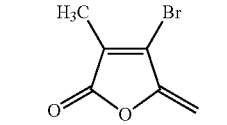 #14

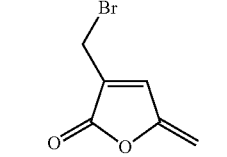

The structure denoted above as #1 is a natural furanone.

These, and other objects, features, and advantages of this invention will become apparent from the following detailed description of the various aspects of the invention taken in conjunction with the accompanying drawings.

DETAILED DESCRIPTION OF THE INVENTION

Figure 1:
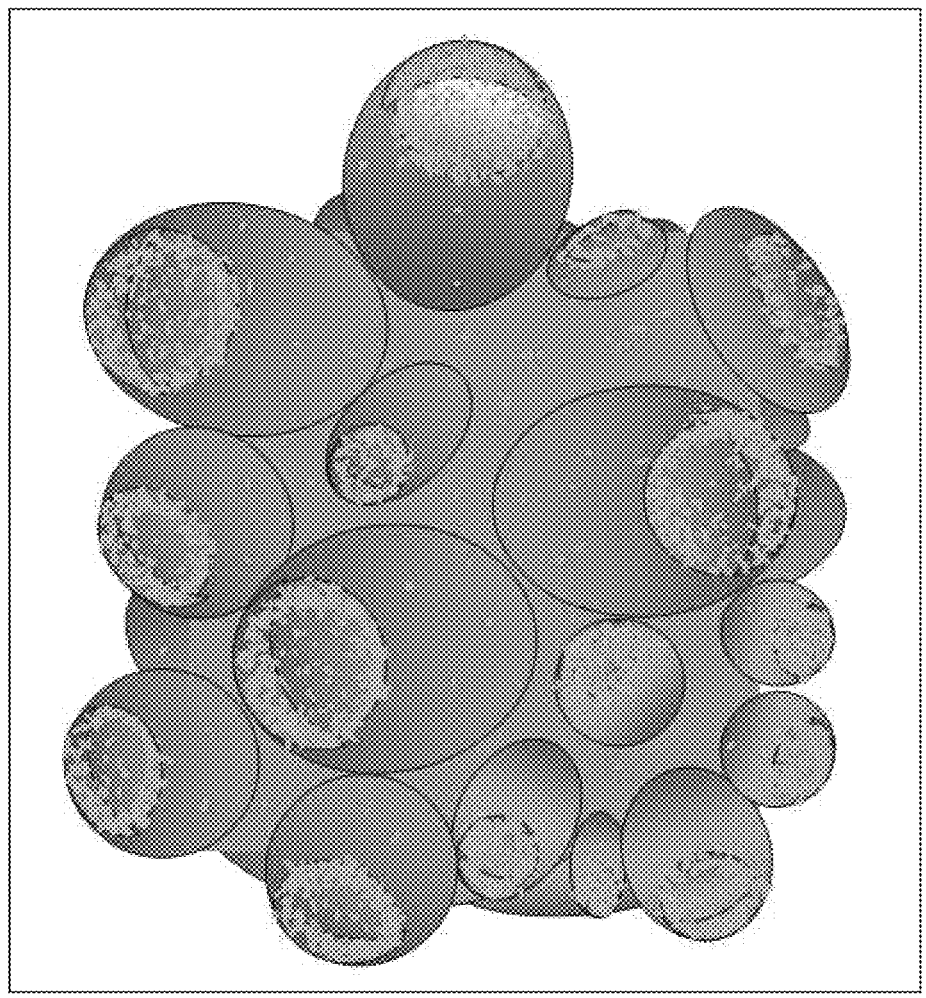
FIG. 1 is a three-dimensional illustration of a hydrogel having protein immobilized on preferred locations.

The present invention provides a new water-in-water emulsion system in which droplets of water-solvated chemicals are dispersed and stabilized in an aqueous solution of certain classes of water-soluble polymers. Therefore, it is an object of the present invention to use this new emulsion to prepare porous hydrogels that are effective for a number of uses, and therefore useful in overcoming many of the deficiencies in the prior art.

All references cited in the Detailed Description are hereby incorporated by reference in their entirety.

Non-Amphiphile-Based Water-in-Water Emulsion Composition:

The present invention provides, in a first aspect, a non-amphiphile-based water-in-water emulsion composition. The non-amphiphile-based water-in-water emulsion composition includes a water-soluble polymer, a non-amphiphilic lyotropic mesogen encapsulated by the water-soluble polymer; and water.

As used herein, the term "water-soluble polymer" refers to any polymer that is soluble in water. The water-soluble polymer can be crosslinked. Suitable water-soluble polymers can include polymers having functional groups including, but not limited to, hydroxyl groups, amide groups, and pyrrolidone groups. Therefore, the present invention contemplates the water-soluble polymers to include, without limitation, polyacrylamides, polyols, poly(pyrrolidones), polysaccharides, and water-soluble fluoride-bearing polymers.

Examples of suitable polyamides include, without limitation, polyacrylamides, poly(N-isopropylacrylamide). and poly(non-charged amino acids). Non-charged amino acids are naturally occurring amino acids that do not bear a charge in the side chain residue, including Alanine, Glycine, Histidine, Isoleucine, Leucine, Methionine, Phenylalanine, Proline, Serine, Threonine, Tryptophan, Tyrosine, and Valine.

Examples of suitable polyols include, without limitation, 2-hydroxyethyl cellulose, 2-hydroxypropyl cellulose, poly alditols (sugar alcohol), and polyvinyl alcohol.

Examples of suitable poly(pyrrolidones) include polyvinylpyrrolidones.

Examples of suitable polysaccharides include, without limitation, pullulan, and hydrophobically modified celluloses that are made water soluble.

Examples of water-soluble fluoride-bearing polymers include, without limitation, a polyamide backbone bearing side chains that are perfluorinated side chains.

It is noted that a non-charged water-soluble polymer includes a polymer that does not have charges, and whose water solubility can come from either or both the backbone and/or the side chain being water-soluble.

As used herein, the term "non-amphiphilic lyotropic mesogen" refers to a non-amphiphilic molecule that can form self-assembly in water; such molecules can include, without limitation, a lyotropic chromonic liquid crystal. A material is referred to as "lyotropic" if it forms liquid crystal phases because of the addition of a solvent. Historically, lyotropic materials composed of amphiphilic molecules. Such molecules comprise a water-loving (hydrophilic) head-group (which may be ionic or non-ionic) attached to a water-hating (hydrophobic) group. Typical hydrophobic groups include, for example, saturated or unsaturated hydrocarbon chains. Examples of amphiphilic compounds include, for example, the salts of fatty acids and phospholipids. Many simple amphiphiles are used as detergents. Lyotropic liquid crystal phases in these materials are formed by a process of self-assembly that is driven by the hydrophobic effect.

The term lyotropic has also been applied to the liquid crystalline phases that are formed by certain polymeric materials, particularly those consisting of rigid rod-like macromolecules, when they are mixed with appropriate solvents. Examples are suspensions of rod-like viruses as the Tobacco Mosaic Virus as well as man-made colloidal suspensions of non-spherical colloidal particles. Other examples include DNA and Kevlar, which dissolves in sulfuric acid to give a lyotropic phase. It is noted that in these cases the solvent acts to lower the melting point of the materials thereby enabling the liquid crystalline phases to be accessible. These liquid crystalline phases are closer in architecture to thermotropic liquid crystalline phases than to the conventional lyotropic phases. In contrast to the behaviour of amphiphilic molecules, the lyotropic behavior of the rod-like molecules does not involve self-assembly.

More specifically, a lyotropic chromonic liquid crystal can include, without limitation, chromonyl molecules. Example of chromonyl molecules include disodium cromoglycate (DSCG), and have a structure as shown below:

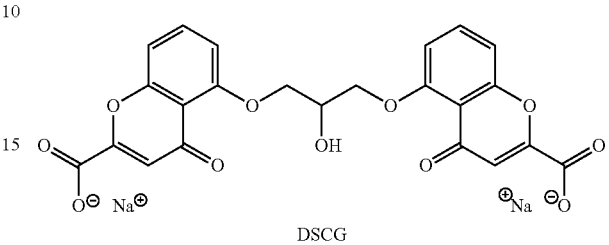

DSCG

Disodium cromoglycate (DSCG), also known as cromolyn sodium salt, is an anti-asthmatic drug discovered in 1936 (Attwood, T. K. et al., J. E. *Mol. Cryst. Liq. Cryst.* 1984, 108, (3-4), 349-57). This molecule forms highly birefringent liquid crystal phases when solvated in deionized water at concentrations ranging from 11 wt % to 21 wt % at room temperature (Lydon, J., *Curr. Opin. Colloid Interface Sci.* 2004, 8, (6), 480-490; Kostko, A. et al., Salt Effects on the Phase Behavior, Structure, and Rheology of Chromonic Liquid Crystals. *J. Phy. Chem. B* 2005, 109, (41), 19126-19133; Lee, H. et al., Phase diagram and thermodynamic properties of disodium cromoglycate-water lyomesophases, *Mol. Cryst. Liq Cryst.* 1983, 91, (1-2), 53-8). The molecular interactions that give rise to the liquid crystalline phase comprised of DSCG are unusual in comparison with other liquid crystals— both thermotropic and lyotropic. As an organic salt, DSCG needs to be solvated in water to form liquid crystals. However, DSCG is not regarded as amphiphilic as the traditional surfactants, of which the aliphatic chain constitutes the hydrophobic component (Lydon, J. *Curr. Opin. Colloid Interface Sci.* 2004, 8, (6), 480-490; Attwood, T. K et al., The distinction between chromonic and amphiphilic lyotropic mesophases. *LIq. Cryst.* 1990, 7, (5), 657-68; Attwood, T. K. et al., The chromonic phases of dyes. *LIq. Cryst.* 1986, 1, (6), 499-507). Consequently, the hydrophobic/hydrophilic segregation that accounts for the self-assembly of surfactants (i.e., traditional lyotropic liquid crystals) cannot be applied to the DSCG liquid crystal system. The molecular-level organization of the DSCG mesogens and their interaction with water are not fully understood, and have been the subject of controversy in the past (Hartshorne, N. H. et al., *Cryst. Liq. Cryst.* 1973, 23, (3/4), 343-68; Hartshorne, N. H. et al., *Mol. Cryst. Liq. Cryst.* 1981, 64, (5-6), 153-4; Lydon, J. E., *Mol. Cryst. Liq. Cryst.* 1980, 64, (1), 19-24). Because DSCG molecule can assume a wide variety of conformations due to the flexible covalent linkage between the two rigid aromatic rings, the director and the optical axis are not as rigorously known as those traditional thermotropic liquid crystals such as 4-cyano-4-n-pentylbiphenyl (5CB) or Methoxybenzilidene butylanaline (MBBA) (Luk, Y.-Y. et al., *Science* 2003, 301, (5633), 623-626). Numerous spectroscopy studies indicate that DSCG molecules self-associate in water at relatively low concentrations (lower than the concentration for the formation of liquid crystals) (Ding, X. S., Thomas C.; Robinson, Joseph R. *J. Pharm. Sci.* 2004, 93, (5), 1351-1358). Because DSCG lacks a "perfectly" well-defined circular disc shape, DSCG liquid crystal is also referred to as "lyotropic chromonic liquid crystal" (Lydon, J. *Curr. Opin. Colloid Interface Sci.* 2004, 8, (6), 480-490; Attwood, T. K. et al., *Mol. Cryst. Liq. Cryst., Lett. Sect.* 1986, 4, (1), 9-14).

When a liquid crystal forms droplets in a carrier phase, the droplet configuration—alignment of liquid crystal in the bulk and on the surface of the droplet, the shape of the droplet, and the topological defects of the liquid crystal—critically depends on the interplay between two sets of molecular effects (Drzaic, P. S., *Liquid Crystal Dispersions.* Wiley-Interscience: Singapore, 1995, Vol. 1; Lavrentovich, O. D., *Liq. Cryst.* 1998, 24, (1), 117-125). First, molecular interactions at the interface can have either a strong or a weak influence on the orientation of the liquid crystal at the surface of the droplet. Second, the elastic constants of the liquid crystal in the bulk determine how amenable it is for the liquid crystal molecules on the surface to orient according to the influence of the surface chemistry at the interface, and consequently determines the shape and the topological defects of the liquid crystal in the droplet effects (Drzaic, P. S., *Liquid Crystal Dispersions.* Wiley-Interscience: Singapore, 1995, Vol. 1; Lavrentovich, O. D., *Liq. Cryst.* 1998, 24, (1), 117-125).

Figure 3:
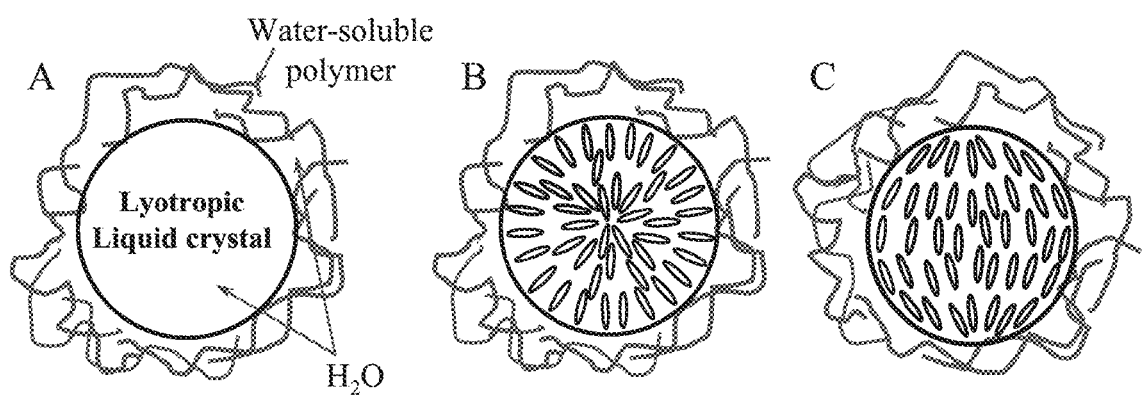
FIGS. 3A-3C depict the following: (A) Model of emulsions of water-solvated liquid crystal (LC) droplets stabilized from coalescence by the adsorption of polymers in a continuous aqueous media. Two possible droplet configurations: (B) Radial configuration: LC molecules align perpendicular to the interface, also known as Hedgehog configuration; (C) Tangential configuration: LC molecules align parallel to the interface, also known as bipolar or "Boojum" configuration (Doane, J. W. *MRS Bull.* 1991, 16, (1), 22-8.).

Dispersions of solid colloidal particles can be stabilized by polymer adsorption on the colloids, while dispersion of oil in water can be stabilized by using surfactants to solubilize the oil droplets (Sato, T.; Ruch, R., *Stabilization of Colloidal Dispersions by Polymer Adsorption.* 1980; p 155). The mechanisms for using surfactant versus polymer to stabilize a dispersion are different—coalescence of oil-loaded micelles is prevented by electrostatic repulsion of the surfactant head groups (Opawale, F. O. et al., *J. Colloid Interface Sci.* 1998, 197, (1), 142-150) whereas flocculation of solid colloids is prevented by so-called "steric repulsion" of the adsorbed polymers (Sato, T. et al., *Stabilization of Colloidal Dispersions by Polymer Adsorption.* 1980; p 155). In this work, we explore the possibility of using polymers to stabilize the emulsion droplets formed by liquid crystals instead of solid particles. Our hypothesis is that liquid droplets can also be stabilized from coalescence by steric repulsion of polymer if the molecular interactions involved are significantly different. Models for stabilized liquid crystal droplets with strong orientational anchoring at the droplet surface are shown in FIGS. 3A-3C.

The present invention also contemplates the use of lyotropic chromonic liquid crystals that include, but are not limited to, 2,5-disulfonic acid diammonium salt-peryleno[3",4":3,4, 5; 10",9":3',4',5']dipyridino[1,2-a: 1',2'-a']bisbenzimidazol-6,11-diol, 6,15-Disulfonicacid-7,16-dichloro-6,15-dihydro-dinaptho[2,3-a;2',3'-h]phenazine-5,9,14,18-tetraone diammonium salt, 4-hydroxy-3-((4-sulfo-1-naphthalenyl) azo)-1-naphthalenesulfonic acid disodium salt, 4-hydroxy-5-[[4-[[1-hydroxy-6-(phenylamino)-3-sulfo-2-naphthalenyl] azo]-5-methoxy-2-methylphenyl]azo]-2,7-naphthalenedisulfonic acid, trisodium salt, (Dimethylamino) phenylazo]benzenesulfonic acid sodium salt, 2-((4'-sulfoniumphenyl azo)-5-(4'-ethoxyphenyl azo)naphthalene sulfonic acid disodium salt, 7-(S-methylsulfonimidoyl)-5-(n-hexyl)-xanthen-9-one-2-carboxylic acid disodium salt, Copper-tetracarboxyphthalocyanine, methine di(3'-propylsulfonic acid, -6'-chloro)thiacarbocyanine triethylamine salt, 2-,6-amino-5-((4-chloro-2-(trifluoromethyl)phenyl)azo)-4-hydroxy-naphthalenesulfonic acid, monosodium salt, 5-[[4'-[(2-amino-8-hydroxy-6-sulfo-1-naphthalenyl)azo][1,1'-biphenyl]-4-yl]azo]-2-hydroxy-benzoic acid, disodium salt, 3,3'-((3,3'-dimethyl(1,1'-biphenyl)-4,4'-diyl)bis(azo))bis(4-amino-1-naphthalenesulfonic acid)disodium salt, 3,3'-[[1,1'-Biphenyl]-4,4'-diylbis(azo)]bis[4-amino-1-naphthalene- sulfonic acid disodium salt, 4-((4-((2-hydroxy-1-naphthenyl) azo)phenyl)azo)-benzenesulfonic acid, monosodium salt, 4,5-Dihydro-5-oxo-1-(4-sulphophenyl)-4-[(4-sulphophenyl) azo-1 h-pyrazole-3-carbolyc acid, 6-Chloro-9-(4-diethylamino-1-methylbutylamino)-2-methoxyacridine dihydrochloride, 4-(2-hydroxynaphthylazo)benzenesulfonic acid sodium salt, trisodium 5-[[4-chloro-6-(phenylamino)-1,3,5-triazin-2-yl]amino]-4-hydroxy-3-[(2-sulphonatophenyl)azo] naphthalene-2,7-disulphonate, and sodium and ammonium salts of perylenetetracarboxylic bisimides (see U.S. Pat. No. 7,294,370).

More specifically, as used herein, chromonyl molecules can include the follow structures (European Patent Application No. EP 90-308997, 19900816):

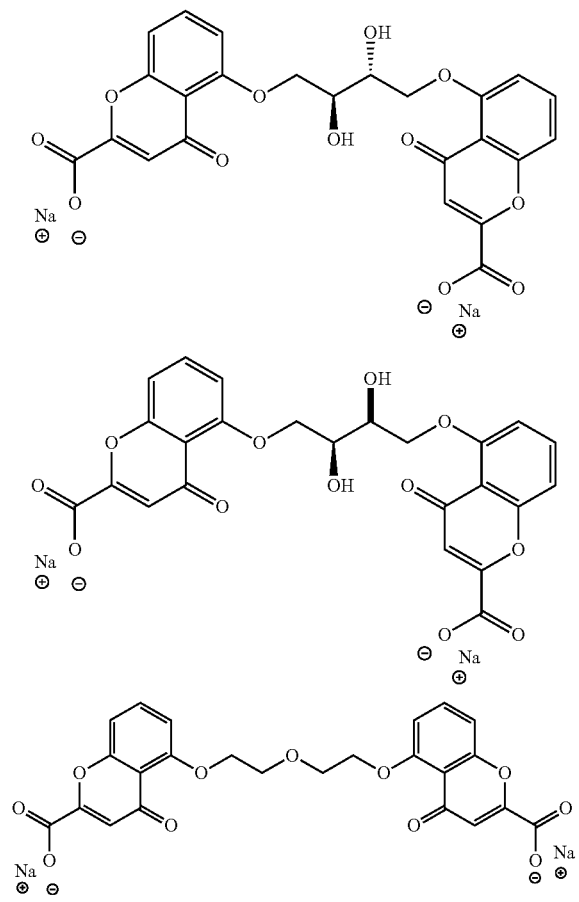

More specifically, as used herein, chromonyl molecules can also include the follow structures:

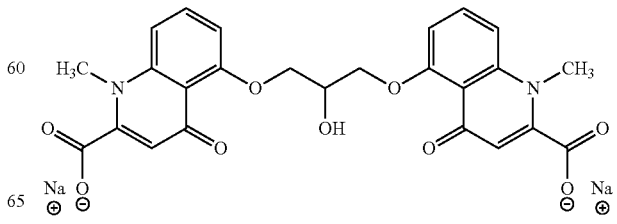

-continued

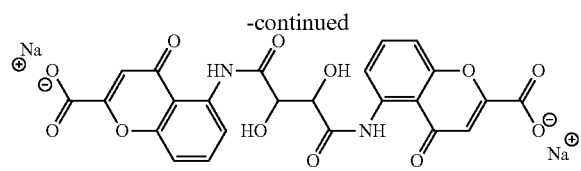

The amount of water-soluble polymer in the water-in-water emulsion composition can be any amount that will support encapsulation of the non-amphiphilic lyotropic mesogen by the water-soluble polymer.

In one embodiment, the non-amphiphilic lyotropic mesogen is present in an amount of about 2 wt. % to about 20 wt. %, based on the total weight of non-amphiphilic lyotropic mesogen and the water-soluble polymer.

All ranges recited herein are meant to include all combinations and subcombinations included within a range's limits.

In a further embodiment, the water-soluble polymer is present in an amount of about 1 wt. % to about 30 wt. %, and the non-amphiphilic lyotropic mesogen is present in an amount of about 2 wt. % to about 20 wt. %. More specifically, the water-soluble polymer is present in an amount of about 6 wt. % to about 8 wt. %, and the non-amphiphilic lyotropic mesogen is present in an amount of about 8 wt. % to about 10 wt. %. Still more specifically, the water-soluble polymer is present in an amount of about 5 wt. % to about 8 wt. %, and the non-amphiphilic lyotropic mesogen is present in an amount of about 5 wt. % to about 8 wt. %.

The non-amphiphile-based water-in-water emulsion composition can further include a compound or other molecule, in addition to the water-soluble polymer and the non-amphiphile lytropic mesogen. The compound or molecule can have, but is not required to have, biocatalytic properties or other desired biochemical properties. In one embodiment, the compound or molecule is a peptide, polypeptide, or more particularly a protein. An example of a suitable protein is one that contains a polymerizable vinyl group.

Even more particularly, the protein can be, without limitation, an enzyme. Examples of suitable enzymes for use in the present invention include, but are not limited to, the following: horseradish peroxidase, amylase, aldolase, lyase, lipase, protease, nitrilase, amino acylase, amidase deaminase, amino acid transaminase, dehydrogenase, amino acid oxidase, amine transaminase, hydroxy oxidase, ketoreductase, ene reductase, and combinations thereof.

Figure 2:
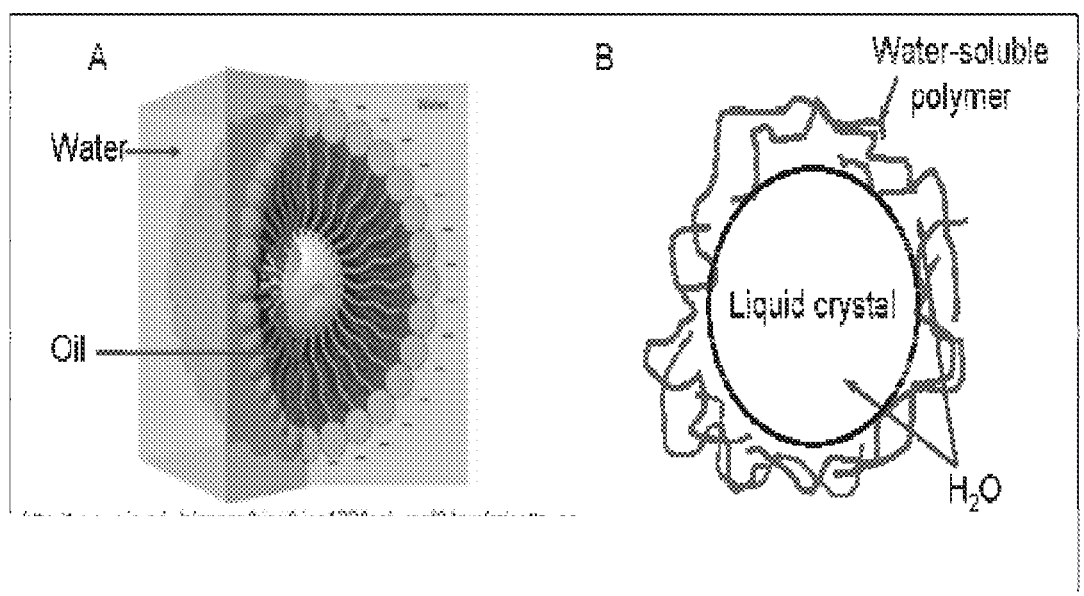
FIGS. 2A-2B are illustrations of a typical oil-in-water emulsion known in the art (FIG. 2A) and a water-in-water emulsion of the present invention (FIG. 2B).

As used herein, a "water-in-water emulsion" (W/W or w/w emulsion) is a system that includes droplets of water-solvated molecules in another continuous aqueous solution. Both the droplet and continuous phases contain different molecules that are entirely water-soluble. As such, when two entirely aqueous solutions containing different water-soluble molecules are mixed together, water droplets containing predominantly one component are dispersed in water solution containing another component. The present invention relates to a water-in-water emulsion that has been found to be stable from coalescence by the separation of different types of non-amphiphilic, but water-soluble, molecular interactions. These molecular interactions include, for example, hydrogen bonding, π stacking, and salt bridging. This W/W emulsion can be generated when the different water-solvated molecular functional groups are segregated in an aqueous mixture comprising polymer and liquid crystal molecules (see FIG. 2B).

In one embodiment of the present invention, the water-in-water emulsion includes liquid crystals suspended as water-solvated droplets dispersed in a solution of polymer whose solvent is also water. The liquid crystal component of the emulsion is disodium cromolyn glycate (DSCG). This molecule is an anti-asthmatic drug, but also exists as a special type of liquid crystal when the concentration of DSCG is ~9-21 wt. %. Unlike conventional lyotropic liquid crystals that consist of oily molecules such as 5CB, DSCG molecules are not amphiphilic, but entirely water-soluble. Thus, the separation of hydrophobic/hydrophilic groups cannot be applied to DSCG. The polymer solution serves as the medium or continuous phase of the w/w emulsion. Apart from being water-soluble, another criterion for the generation of this w/w emulsion system is that the polymer does not bear functional groups that interact strongly with DSCG. As such, an ionic polymer when mixed with DSCG does not form w/w emulsion, but gives rise to a homogeneous solution or a precipitate solution. Some of these water-in-water emulsions can be exceptionally stable from coalescence for up to 30 days.

Because molecules of liquid crystal assume a preferred common orientation among themselves, the overall orientation of liquid crystals in a droplet is stable in certain configurations (see FIGS. 3A-3C). As water solvated droplets in a w/w emulsion, DSCG molecules would align in a preferred direction on the surface of the droplet. In order to minimize the overall energy of the system, the DSCG molecules in the droplet prefer to align either parallel or perpendicular to the surfaces of the droplets (see FIGS. 3B-3C).

The stability of the water-in-water emulsion of the present invention from coalescence can be attributed to three molecular forces. First, the separation of different molecular forces at the beginning of the droplet formation affects coalescence. In particular, similar forces tend to stay together: π-stacking and salt bridging are the two dominant forces in the liquid crystal droplet phase, while hydrogen bonding governs in the continuous polymer phase. Second, as the droplet size increases, the molecular interactions at the interface of the droplet phase and the continuous phase become stronger through multivalent interactions. The strengthening of interfacial molecular interactions in w/w emulsions results in the formation of a layer of polymer that coats the surface of the droplet that consequently prevents droplets from clumping together. Third, it is also proposed that when two liquid crystal droplets merge together (i.e., coalescence), the orientation of the liquid crystal molecules in the two merging droplets must change to "adapt" to each other, and thus incur an energy penalty which prevents the occurrence of coalescence.

The w/w emulsion of the present invention represents a new class of polymer-dispersed liquid crystals (PDLC). As traditionally known, PDLC consists of an oil-in-water emulsion where the oily droplet is a thermotropic liquid crystal such as 4-pentyl-4'-cyanobiphenyl (5CB), and the water phase contains certain polymers. In comparison, in one particular embodiment of the present invention, the water-in-water emulsion includes polymer-dispersed lyotropic liquid crystals, where the lyotropic liquid crystal is DSCG molecules solvated in water. Traditional PDLCs have been found to be useful in applications such as switchable windows and projection displays. In contrast, the water-in-water emulsion of polymer-dispersed lyotropic liquid crystals of the present invention has the potential for building highly bio-functional materials because of its compatibility with protein structure.

Porous Hydrogel Composition:

The present invention provides, in a second aspect, a porous hydrogel composition. The porous hydrogel composition includes a cross-linked water-soluble polymer network containing a plurality of pores. In one embodiment, the pores are produced by (i) encapsulating a non-amphiphilic lyotropic mesogen within a shell comprised of a cross-linked water-soluble polymer; and (ii) removing the non-amphiphilic lyotropic mesogen to form the pores. Suitable means for removing the non-amphiphilic lyotropic mesogen from the shell can include, without limitation, the process of diffusion.

The pores of the porous hydrogel composition of the present invention can have an average pore diameter of about 5 μm to about 40 μm. Further, the porous hydrogel composition can have pores that are interconnected, non-interconnected, or a combination of interconnected and non-interconnected pores.

In a further embodiment, the porous hydrogel composition can further include a biocatalytic compound. The biocatalytic compound can be either covalently or non-covalently immobilized. In a particular embodiment, the biocatalytic compound can be, without limitation, any compound that is effective for inhibiting the formation of biofilm, detecting a target substance in an aqueous solution, or degrading a polysaccharide in solution. In a more particular embodiment, the biocatalytic compound can include a bromosubstituted furanone, particularly those described herein.

The biocatalytic compound can also include a compound such as previously mentioned above in relation to the non-amphiphile-based water-in-water emulsion composition. It is also contemplated that the biocatalytic compound can include compounds or molecules that function as detecting agents for other compounds or organisms. An example of a suitable detecting agent can include an antigen, an antibody, or an enzyme. Enzymes suitable for this aspect of the invention include, without limitation, horseradish peroxidase, an amylase, an aldolase, a lyase, a lipase, a protease, a nitrilase, an amino acylase, an amidase deaminase, an amino acid transaminase, a dehydrogenase, an amino acid oxidase, an amine transaminase, a hydroxy oxidase, a ketoreductase, an ene reductase, and combinations thereof.

Antibody-antigen pairs used in the water-in-water emulsion and porous hydrogel of the present invention can include, without limitation, the following: (1) antibody for the pilin protein of *Pseudomonas aeruginosa* strain K and the peptide sequence containing the epitope (N-ACTSDQDPMFIP-KGCSK-C) (SEQ ID NO:1) on the pilin protein, which is derived from the native epitope (N-KCTSDQDEQFIP-KGCSK-C) (SEQ ID NO:2); and (2) goat anti-rabbit IgG and rabbit IgG. However, the present invention is not limited by these particular examples of antibody-antigen pairs, as any antibody-antigen pair can be used in the water-in-water emulsion and/or the porous hydrogel of the present invention.

The present invention provides, in a third aspect, a method for forming the porous hydrogel composition of the present invention. This method involves preparing a water-in-water emulsion composition that comprises at least one water-soluble monomer, a non-amphiphilic lyotropic mesogen, at least one modifier compound, and water. The water-soluble monomer is polymerized into a water-soluble polymer that encapsulates the non-amphiphilic lyotropic mesogen. The non-amphiphilic lyotropic mesogen is then removed from the water-soluble polymer, thereby forming the porous hydrogel composition.

The at least one water-soluble monomer can include any monomer suitable for polymerization into a water-soluble polymer. Particular suitable monomers are as previously discussed herein. Suitable non-amphiphilic lyotropic mesogens are also as previously described herein. The at least one modifier compound can include, without limitation, a biocatalytic compound, also as previously described herein.

Three-Dimensional Cell Culture:

The present invention provides, in a fourth aspect, a three-dimensional cell culture having a scaffold comprised of the porous hydrogel composition of the present invention. The porous hydrogen is modified with cell adhesion protein such as fibronectin or cell adhesion peptides such as Argnine-Glycine-Aspartic acid (RGD). The present invention can be used to overcome the deficiencies in the art with regard to three-dimensional cell culture, as discussed below.

Activities of mammalian cells, living or dead, critically depend on some sort of ligand-receptor mediated adhesion on a surface. The most common type of ligand receptor interaction includes a transmembrane protein integrin (receptor) that binds to a tripeptide ligand (Arg-Gly-Asp, RGD), usually located in the protein fibronectin in the extracellular matrix. This integrin-RGD binding will induce integrins to migrate and form clusters in the membrane; such clusters will further recruit a collection of protein in the cytosol to form a highly orchestrated assembly (focal adhesion), enabling the normal physiology of the cell to proceed. Traditionally, such adhesion for culturing cells and tissues is conducted on flat surfaces of plastic Petri dishes, mainly because it is operationally easy and feasible. While many important discoveries were made with this two-dimensional approach, it is clear that work is essential in a three-dimensional context, in which cells grow in native biological systems, to answer many important questions in biology, including development of cancers and their response to drugs. For instance, in a landmark discovery by Bissell, it was found that an antibody that binds to a specific integrin ($\beta_1$) completely changed the characteristics of cancer cells, almost turning them non-cancerous, when the cells are cultured in a three-dimensional culture matrix (Malissard, M. and E. G. Berger, Improving the solubility of the catalytic domain of human beta-1,4-galactosyltransferase 1 through rationally designed amino-acid replacements. Eur. J. Biochem., 2001. 268(15): p. 4352-4358; Malissard, M., L. Borsig, S. Di Marco, M. G. Gruetter, U. Kragl, C. Wandrey, and E. G. Berger, Recombinant soluble beta-1,4-galactosyltransferases expressed in *Saccharomyces cerevisiae*. Purification, characterization and comparison with human enzyme. Eur. J. Biochem., 1996. 239(2): p. 340-348). Such drug effect from the antibody is not observed in the normal two-dimensional culture-ware. Other enhanced cell activities are also observed in three-dimensional culture matrix, but not on the usual two-dimensional Petri dishes (Seitz, O. and C.-H. Wong, Chemoenzymic solution- and solid-phase synthesis of O-glycopeptides of the Mucin domain of MAdCAM-1. A general route to O-LacNAc, O-Sialyl-LacNAc, and O-Sialyl-Lewis-X peptides. J. Am. Chem. Soc., 1997. 119(38): p. 8766-8776; Prieels, J. P., M. Dolmans, M. Schindler, and N. Sharon, The binding of glycoconjugates to human-milk D-galactosyltransferase. Eur. J. Biochem., 1976. 66(3): p. 579-82).

Currently, the most used three-dimensional culture matrix is a 1980s technology based on a material called Matrigel™, an undefined cocktail of substances extracted from the extracellular matrix of mouse tumor (Sheares, B. T. and P. W. Robbins, Glycosylation of ovalbumin in a heterologous cell: analysis of oligosaccharide chains of the cloned glycoprotein in mouse L cells. Proc. Natl. Acad. Sci. U.S.A. FIELD Full Journal Title: Proceedings of the National Academy of Sciences of the United States of America, 1986. 83(7): p. 1993-7; Chang, T. M. S., Therapeutic applications of polymeric artificial cells. Nat. Rev. Drug Discovery, 2005. 4(3): p. 221-235). Thus, the important cell responses seen in three-dimensional cell culture are due to a convoluted mixture of chemical, physical (hardness and elasticity, for example) and geometric effects.

Connected hydro-shells can be employed to present a well-defined chemical composition, toughness and geometry for three-dimensional cell culture, and compare the cell activities (focal adhesion and formation of actin filaments) with an equally well-defined two-dimensional counterpart. A cyclic peptide containing RGD residues (Peptide International Inc, KY) can be polymerized in the three-dimensional hydroshells in situ for binding to the receptor integrin of mammalian cells. Tests of the three-dimensional materials may be carried out using Swiss 3T3 fibroblast and neuron cells that have different growth preference to provide different toughness of the surfaces.

For the two-dimensional comparison, a well-defined surface composed of self-assembled alkanethiols presenting RGD ligands in bio-inert backgrounds of mannitols and oligo (ethylene glycol) on gold films can be employed. Even for a two-dimensional surface, the topography at nanometer scale can influence cell activity to great extent.

Biological characteristics of particular interest for the three-dimensional systems of the present invention include, without limitation, formation of focal adhesion and actin filaments, and the potency of natural ligands (RGD tripeptide) and synthetic drugs that block the binding site on the integrin. Because the three-dimensional cell culture presents curved surfaces resembling more the in vivo conditions, where cells do not need to attach as strongly as on a flat surface, it may be that less focal adhesion and actin filament is needed, and the inhibitors will exhibit a higher potency on the three-dimensional versus two-dimensional cell culture systems.

Substrate:

The present invention provides, in a fifth aspect, a substrate that includes a layer formed on the substrate, where the layer comprises the porous hydrogel composition of the present invention. In one embodiment, a thin layer of porous hydrogel is grafted on a glass substrate by in situ polymerization of acylamide and/or derivatized acrylamide on a glass slide modified with polymerizable acrylic groups. The porous hydrogel composition of the present invention can be used to form layers on any type of substrate surface, including those further discussed herein.

Method of Inhibiting Biofilm Formation:

The present invention provides, in a sixth aspect, a method for inhibiting biofilm formation. This method involves providing a surface that is susceptible to biofilm formation. The surface is then modified by introducing onto the surface the porous hydrogel composition of the present invention, where the hydrogel is effective to inhibit bio film formation on the surface.

Biofilms are well known in the art. Various studies show that some common biofilms found in the medical field (e.g., indwelling medical devices) are formed from microorganisms such as gram-positive bacteria, gram-negative bacteria, and/or yeasts. Examples of commonly isolated biofilm-forming bacteria include, for example, gram-positive bacteria such as *Enterococcus faecalis, Staphylococcus aureus, Staphylococcus epidermidis*, and *Streptococcus viridans*; and gram-negative bacteria such as *Escherichia coli, Klebsiella pneumoniae, Proteus mirabilis*, and *Pseudomonas aeruginosa*. Commonly encountered yeast species that can form biofilms include, for example, *Saccharomyces cerevisiae, Candida albicans, Candida parapsilosis, Candida krusei*, and *Torulopsis glabrata*. These organisms may originate from the skin of patients or health-care workers, tap water to which entry ports are exposed, or other sources in the environment. Biofilms may be composed of a single species or multiple species, depending on the device and its duration of use in the patient.

The method of inhibiting biofilm formation can be used to inhibit, prevent, and/or treat biofilm formed by one or more biofilm-forming bacteria. It is contemplated that such biofilm-forming bacteria can include, but is not limited to, *Pseudomonas* spp., *Klebsiella* spp., *Enterococcus* spp., *Bacillus* spp., *Escherichia* spp., *Haemophilus* spp., *Salmonella* spp., *Yersinia* spp., *Nessieria* spp., *Mycobacterium* spp., *Streptococcus* spp., *Staphylococcus* spp., and *Vibrio* spp. More particularly, the biofilm-forming bacteria can include, without limitation, the following species: *Pseudomonas aeruginosa, Klebsiella pneumoniae, Enterococcus faecalis, Bacillus subtilis, Bacillus anthracis, Bacillus cereus, Escherichia coli, Haemophilus influenzae, Salmonella typhimurium, Salmonella paratyphi, Salmonella typhi, Yersinia pestis, Nessieria menignitidis, Mycobacterium tuberculosis, Streptococcus mutans, Streptococcus salivarius, Streptococcus viridans, Streptococcus constellatus, Streptococcus agalactiae, Streptococcus pneumoniae, Staphylococcus aureus, Staphylococcus epidermidis, Vibrio haveryi*, and *Vibrio cholerae*.

The process of biofilm formation is complex and influenced by many factors. For example, the microorganisms must adhere to exposed surfaces (e.g., surface of a medical device) for sufficient time to become irreversibly attached. The rate of cell attachment depends on the number and types of cells in the liquid to which the surface is exposed, the flow rate of liquid through or on the surface, and the physicochemical characteristics of the surface. Components in the liquid may alter the surface properties and also affect rate of attachment. Once these cells irreversibly attach and produce extracellular polysaccharides to develop a biofilm, rate of growth is influenced by flow rate, nutrient composition of the medium, antimicrobial-drug concentration, and ambient temperature.

The method of inhibiting biofilm formation is useful in inhibiting such formation on all types of surfaces, including, without limitation, surfaces comprised of materials such as metal, metal alloy, glass, plastic, silicone, ceramic, wood, and combinations thereof.

As previously mentioned, a biocatalytic compound can be incorporated into the porous hydrogel composition of the present invention to function in inhibiting biofilm formation. In one embodiment, the biocatalytic compound is a covalently immobilized enzyme that is effective for degrading a polysaccharide in solution. Suitable enzymes can also include, but are not limited to, the following: lyase, aldolase, lipase, protease, nitrilase, amino acylase, amidase deaminase, amino acid transaminase, dehydrogenase, amino acid oxidase, amine transaminase, hydroxy oxidase, ketoreductase, ene reductase, and combinations thereof.

Another biocatalytic compound that can be incorporated into the porous hydrogel composition include bromosubstituted furanone that are effective in inhibiting and treating biofilm formation. In a particular embodiment, the bromosubstituted furanone can be non-covalently immobilized. Particular bromosubstituted furanones can also include those of the present invention, as described in more detail herein.

Method for Preparing a Therapeutic Compound:

The present invention provides, in a seventh aspect, a method for preparing a therapeutic compound. This method involves providing a precursor to a therapeutic compound. The precursor is contacted to the porous hydrogel composition of the present invention under conditions effective to form the therapeutic compound. In this aspect, the porous hydrogel composition further comprises a covalently immobilized enzyme that is effective to catalyze formation of the therapeutic compound from the precursor.

In one embodiment, this method can be used to prepare sialic acid. In this embodiment, the enzyme used is aldolase. The porous hydrogel containing covalently immobilized N-acetyl neuraminic acid aldolase (NeuAc aldolase) is immersed in an aqueous solution of sodium pyruvate and mannose to form a stereospecific sialic acid product. The progress of the reaction is monitored by an assay that measures the depletion of pyruvate.

Method for Modifying a Protein Biopharmaceutical Compound:

The present invention provides, in an eighth aspect, a method for modifying a protein biopharmaceutical compound. This method involves providing an unmodified protein biopharmaceutical compound that is subject to a desired modification. The unmodified protein biopharmaceutical compound is contacted to the porous hydrogel composition of the present invention under conditions effective to form a modified protein biopharmaceutical compound. In this aspect, the porous hydrogel composition further comprises a covalently immobilized enzyme that is effective to catalyze the desired modification of the unmodified protein biopharmaceutical compound.

Glycosylation of proteins and peptides is critical for chemical signaling that governs many activities of mammalians cells, but still remains one of the more difficult subjects in cell biology because of the difficulty in characterizing sugar molecules on the proteins. Control of glycosylation is also important for developing protein drugs (i.e., biopharmaceuticals) not only for maintaining the proper function of a protein, but also for preventing protein aggregation. Protein aggregation is a daunting problem for the biopharmaceutical industry as it increases the cost of production, and, more importantly, can cause extremely undesired, sometimes fatal, immunoresponse.

In one embodiment of this method, the enzyme catalyzes glycosylation of the unmodified protein biopharmaceutical compound. The porous hydrogel covalently immobilized with β-1,4-Galactosyl transferase (β4Gal-T1) is immersed in an aqueous solution containing galactose and a protein containing glycosylation sites for β4Gal-T1, ovalbumin, to form galactosylated proteins.

Method for Modifying a Surface:

The present invention provides, in a ninth aspect, a method for modifying a surface. This method involves providing a surface to be modified. The surface is coated with a porous hydrogel composition of the present invention, thereby modifying the surface so that the surface has the same functionality as the porous hydrogel composition. Various surfaces can be modified by this method, including, without limitation, a surface comprising a material such as metal, metal alloy, glass, plastic, silicone, ceramic, wood, and combinations thereof.

Method of Analyzing an Aqueous Solution for a Target Substance:

The present invention provides, in a tenth aspect, a method of analyzing an aqueous solution for the presence of a target substance. This method involves providing a porous hydrogel composition of the present invention, where the porous hydrogel composition comprises an antibody that is effective for detecting the presence of a target substance. The porous hydrogel composition is contacted to an aqueous sample suspected of containing the target substance under conditions effective to produce a detection signal if the target substance is present. Thereafter, analysis is conducted to determine the presence of a detection signal output, where the presence of the detection signal indicates the presence of the target substance.

In one embodiment, the present invention can involve using a weak antibody-antigen binding as part, or all, of the crosslinking for the porous hydrogel of the present invention. When a targeted antigen is present in solution, the crosslink formed by the weak antibody-antigen binding will be displaced by solution-borne antigen, causing an abrupt increase in the swelling, perhaps even complete dissolution, of the hydrogel, resulting in a readily visible change in the shape and size of the hydrogel. This antigen-responsive mechanism, in the absence of a porous structure, has been previously observed, but it suffered from a slow response time (~ one hour) and a less-than-desirable increase in swelling ratio (~10%), both of which cause the detection of hydrogel shape change by naked eye to be essentially impossible. The use of a porous structure, in accordance with the present invention, would lead to a faster response time that is enhanced by the rapid diffusion of agents in and out of the hydrogel, as well as an increase in signal magnitude, enhanced by the increased swelling ratio of the hydrogel.

This detection principle is broadly applicable to any aqueous borne toxin that generates an immunoresponse in animals to produce antibodies. Examples of such aqueous borne toxins include, without limitation, the following: the virulence factor HrpW, a protein secreted by plant pathogen *Pseudomonas syringae*; and the whole bacteria cell of *Pseudomonas aeruginosa*, an animal pathogen that infects immuno-compromised individuals, including burn victims, and patients with bone marrow transplant, cancer, AIDs or cystic fibrosis. Pillin protein initiates the attachment of *Pseudomonas aeruginosa* to the host cell. *Pseudomonas syringae* is a representative class of bacteria that infect a variety of plant species and cause diseases such as leaf spots, stem cankers, and bacterial speck.

The invasion of pathogenic bacteria depends on their adhesion to the host cells or tissues, and pilus-mediated adherence is considered the first step for initial colonization of *Pseudomonas aeruginosa*. Because both the antibody for the pilin protein of *Pseudomonas aeruginosa* strain K and the epitope on the pilin protein are both well-established, the monoclonal antibody and the peptide sequence constituting the epitope (N-ACTSDQDPMFIPKGCSK-C) (SEQ ID NO:1) can be incorporated into the polymers. (The residues in bold font indicate modifications of the sequence of the native epitope (N-KCTSDQDEQFIPKGCSK-C) (SEQ ID NO:2) such that the binding of the modified epitope with the antibody is known to be weaker than the native sequence. One of the lysine residues (K) can be modified with an acrylic group to enable polymerization. This relatively weak antibody-antigen binding facilitates a rapid displacement by the targeted free antigen that contains the native epitope on the pilin protein. The antibody can be developed towards the native epitope (N-KCTSDQDEQFIPKGCSK-C) (SEQ ID NO:2). The peptide sequence can be obtained by custom peptide synthesis and used to develop polyclonal antibody in rabbits using custom antibody production (Cocalico Biologicals, Inc., Reamstown, Pa.).

The preparation of anti-HrpW antibody is similar to that for pilin protein, except that HrpW antigen is a protein (43 kDa) that cannot be obtained by custom synthesis. The Gateway® cloning system (Invitrogen, Inc., Carlsbad, Calif.) can be employed to engineer an *Escherichia coli* strain to express the HrpW protein with 6×His tag, which can be purified by a Ni-NTA column (Qiagen, Inc., Valencia, Calif.). The purified protein can be used to manufacture its antibody by custom antibody production.

Both the antibody and antigen-laden linear polymer can be prepared by mixing the linear polymers that tether the antibody into a gel formation mixture of antigen monomers, acrylic amide monomer, and DSCG. As the gel forms, part of the crosslinking is provided by non-covalent antigen-antibody binding.

For the purpose of detection, the porous hydrogel crosslinked with antigen-antibody can be immersed directly in solutions containing different-concentrations of *Pseudomonas aeruginosa* and virulence factor Hrp W; the resulting change in the shape, size, and swelling ratio (wet weight/dry weight) of the hydrogel can then be recorded. As the binding constant of antibody is on the scale of nanomolar to picomolar, the sensitivity would be expected to be around tens to hundreds of nanomolar of both the *Pseudomonas aeruginosa* and the secreted virulence factor HrpW from *Pseudomonas syringae*.

In addition, the porous hydrogel can be designed to that horseradish peroxidase (HRP) is immobilized thereon to catalyze the chemiluminescence reaction of luminol, which generates a visible blue light having a wavelength maximum at 424 nm. For example, a porous hydrogel of the present invention can be soaked in a solution of HRP, resulting in non-covalent protein incorporation, and also prepared to determine the diffusion of protein in and out of the porous hydrogel. Because the light emission is significantly faster than the diffusion of the activated product at triplet state, the region emitting light indicates the presence of HRP.

In another embodiment, the porous hydrogel of the present invention can be designed to use the activity of an amylase-laden porous hydrogel on degrading oligosaccharides for detection purposes. For example, amylase catalyzes the breakdown of polysaccharide by hydrolyzing α-1,4-glycosidic linkages. Because the degraded sugar fragments have anomeric groups that can be oxidized by reducing other chemicals such as dinitrosalicylic acid (DNS), a colorimetric assay can be used to quantify the amylase's activity on hydrogel. Therefore, the present invention represents the beneficial effect of a porous biocatalytic scaffold.

Novel Bromosubstituted Furanones:

The present invention provides, in a eleventh aspect, a bromosubstituted furanone having a structure of the formula:

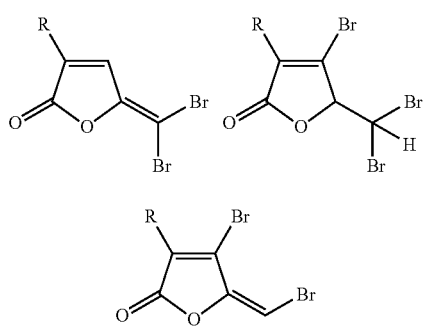

where R can include, without limitation, alkyl, aromatic rings, coumarin, cromolyn, or adamantane.

Examples of aromatic ring, coumarin, cromolyn, and adamantane are shown below.

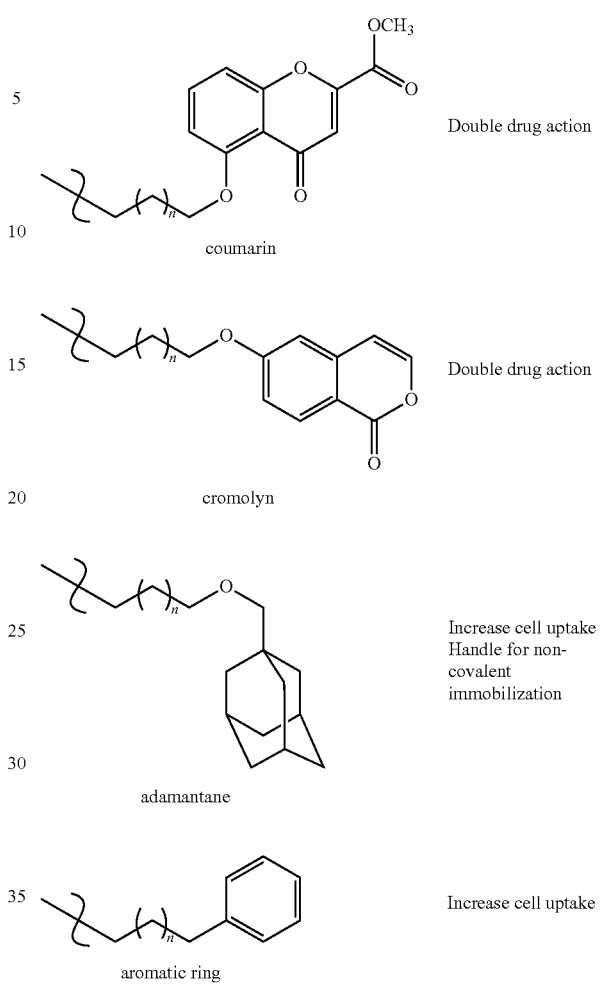

As used in reference to the above R groups, n=0, 1, 2, 3, 4, 5, 6, 7, 8, or 9.

More specifically, the bromosubstituted furanone has a structure, including, but not limited to, a structure of the following formulae:

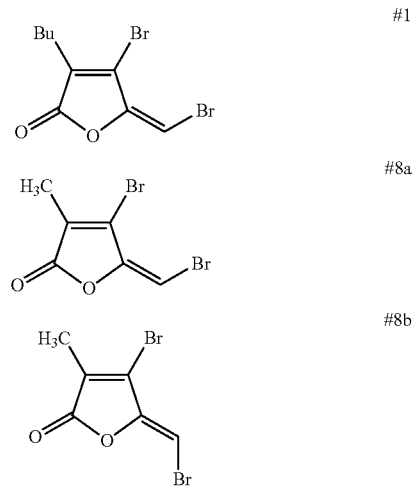

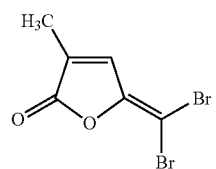
9

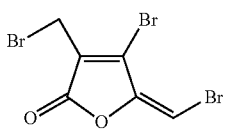
10

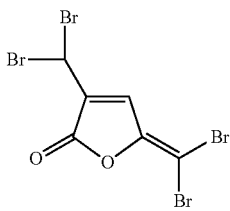
11

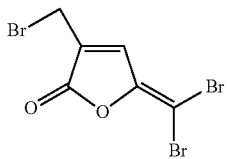
11a

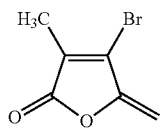
12

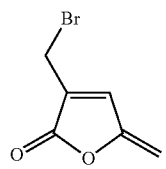
13

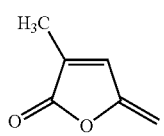
14

It is noted that structure indicated as #1 above is a nature furanone.

In one embodiment, certain of the bromosubstituted furanones of the present invention can be synthesized as follows:

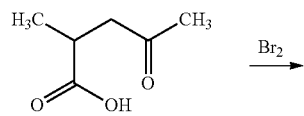

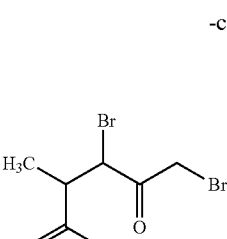

+

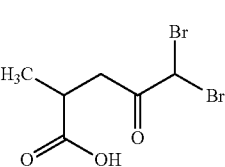

$\xrightarrow{\text{98\% H}_2\text{SO}_4}$

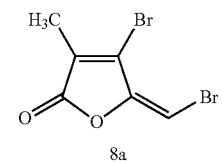
8a

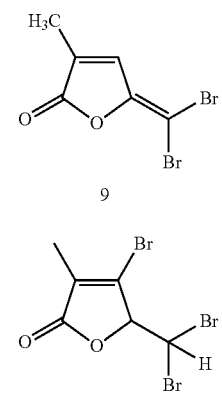

The brominated furanones of the present invention can be used for as previously described herein. Further, these brominated furanones can also be used for a number of other purposes, including, without limitation, for solutions for cleaning contact lenses, kitchens, countertops, dishwashers, bathrooms, fish tanks, and swimming pools. Further, the brominated furanones of the present invention can also be used in various other ways, including, for example, in shampoos, toothpastes, mouth wash solutions, tissues having antimicrobial functions, materials for wound-cleaning/healing. The brominated furanones can also be used to decontaminate hospital wards or other clinical facilities, and can be used in food packaging materials.

The brominated furanones of the present invention can also be immobilized on surfaces to prevent biofilm formation on various devices, including, but not limited to, such devices as: contact lenses, catheters, surgical tools, blood pressure cuffs, and implanted medical devices.

EXAMPLES

The following examples are intended to illustrate particular embodiments of the present invention, but are by no means intended to limit the scope of the present invention.

Example 1

Water-in-Water Emulsions Stabilized by Non-Amphiphilic Interactions: Polymers Dispersed Lyotropic Liquid Crystals Emulsion systems involving surfactants are mainly driven by the separation of the hydrophobic interactions of the aliphatic chains from the hydrophilic interactions of amphiphilic molecules in water. This example describes an emulsion system that does not include amphiphilic molecules, but molecules with functional groups that are completely solvated in water. These functional groups give rise to molecular interactions including hydrogen bonding, π-stacking, and salt bridging, and are segregated into a dispersion of droplets forming a water-in-water emulsion. This water-in-water emulsion consists of dispersing droplets of a water-solvated biocompatible liquid crystal-disodium cromoglycate (DSCG), in a continuous aqueous solution containing specific classes of water-soluble polymers. Whereas aqueous solutions of polyols support the formation of emulsions of spherical droplets consisting of lyotropic liquid crystal DSCG with long-term stability (for at least 30 days), aqueous solutions of polyamides afford droplets of DSCG in the shape of prolate ellipsoids that are stable for only 2 days. The DSCG liquid crystal in spherical droplets assumes a radial configuration, in which the optical axis of the liquid crystal aligns perpendicular to the surface to the droplets, but assumes a tangential configuration in prolate ellipsoids, in which the optical axis of the liquid crystal aligns parallel to the surface of the droplet. Other classes of water-soluble polymers including poly ethers, polycations and polyanions do not afford stable emulsion of DSCG droplets. Both the occurrence and stability of this unique emulsion system can be rationalized based on the functional groups of the polymer. The different configuration of the liquid crystal (DSCG) droplets was also found to correlate with the strength of the hydrogen bonding that can be formed by the functional groups on the polymer.

This example discusses the molecular interactions that are usually associated with biological molecules (not aliphatic hydrophobic interactions) to form a water-in-water emulsion (Simon, K. A., et al., "Water-in-Water Emulsions Stabilized by Non-Amphiphilic Interactions: Polymer-Dispersed Lyotropic Liquid Crystals," *Langmuir,* 2007, 23(3): p. 1453-1458). This emulsion system involves dispersing water-solvated droplets of a unique non-amphiphilic lyotropic liquid crystal in aqueous solutions containing different classes of polymers. Also presented is the interfacial chemistry that controls the orientation of the liquid crystals on the surface of the droplets.

Experimental Section

Materials.

Disodium cromolyn glycate (DSCG) was purchased from MP Biomedicals (Solon, Ohio). Poly(acrylic acid, sodium salt) (PAA-Na, $M_w$ 1,200, 45% and $M_w$ 15,000, 35%), poly (vinyl alcohol) (PVA, $M_w$ 89,000-98,000, 99+%), poly(ethylene glycol) (PEG, $M_n$ 1,305-1,595 waxy solid), poly(sodium 4-styrenesulfonate) (PSS, $M_w$ 70,000, powder), hydroxypropyl cellulose (HPC, $M_w$ 80,000 powder), polyacrylamide (PAAm, $M_w$ 10,000, 50%), poly(methacrylic acid, sodium salt) (PMAA-Na, Mw 9,500), polyethyleneimine (PEI, $M_w$ 750,000), poly(N-isopropylacrylamide) (PNIPAAm, M, 20,000-50,000), poly(allylamine hydrochloride) (PAH, $M_w$=70,000), and pullulan from *Aureobasidium pullulans* were purchased from Aldrich (St. Louis, Mo.). All reagents were used as received. Fisherfinest® glass microscope slides were purchased from Fisher Scientific. Deionized water with a resistivity of 18.2 MΩ-cm is used for preparation of all of the lyotropic liquid crystal samples.

Liquid Crystal Cell Assembly and Birefringence Measurement.

The liquid crystal samples were assembled in a sandwiched cell composed of two glass microscope slides with multiple sheets of Saran Wrap (13-15 μm thick each) to afford a spacer of about 42 μm thick. The sheets of Saran Wrap were punched to create a hole to accommodate the liquid crystal sample to be sandwiched between the glass slides. The sample was vortexed for at least 1 min before loading it in between the slides, and sealing it with binder clips on each side to prevent evaporation of water. Samples were viewed under crossed polarizers on Olympus BX51 Polarizing Microscope and were rotated in 15 degree increments from an arbitrary starting point to record the birefringence.

Results and Discussion

This work examined a broad range of water-soluble polymers with different functional groups that have the potential to exclude DSCG molecules to form water-solvated droplets (Scheme 2, below).

Scheme 2.

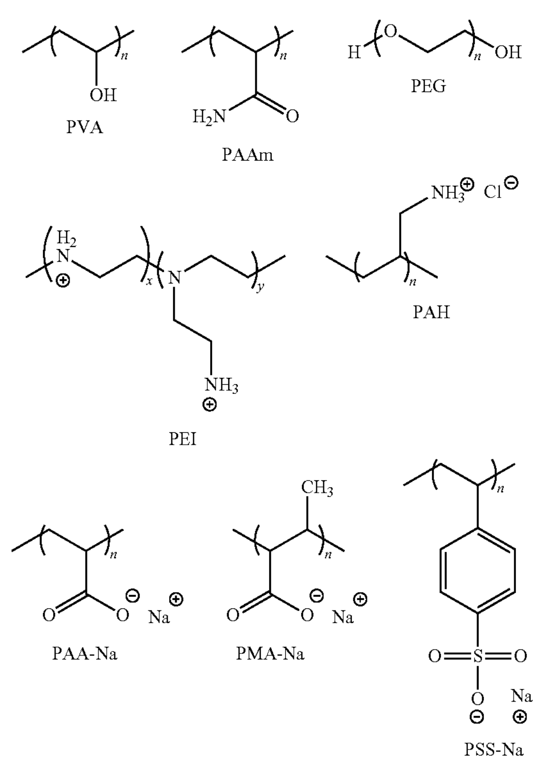

PVA, PAAm, PEG, PEI, PAH, PAA-Na, PMA-Na, PSS-Na

These polymers consist of non-ionic, anionic and cationic water-soluble polymers.

Non-ionic polymers include polyvinyl alcohol (PVA, $M_w$=89,000-98,000), hydroxypropyl cellulose (HPC, $M_w$=80,000), pullulan from *Aureobasidium pullulans*, polyacrylamide (PAAm, $M_w$=10,000), poly N-isopropylacrylamide (Poly-NIPAAm, $M_w$=20,000-25,000) and polyethylene glycol (PEG, $M_w$=1305-1595).

Anionic polymers include poly(acrylic acid, sodium salt) (PAA-Na, $M_w$=1,200 & 15,000), polysodium 4-styrenesulfonate (PSS, $M_w$=70,000), polymethacrylic acid, sodium salt (PMA-Na, Mw=9,500). Cationic polymers include polyethyleneimine (PEI, $M_w$=750,000), and poly(allylamine hydrochloride) (PAH, $M_w$=70,000). All samples were prepared with deionized water with a resistivity of at least 18.2 MΩ-cm.

It was discovered that, in general, nonionic polymers can give rise to stable emulsions of DSCG in water, whereas anionic polymers afford unstable emulsions of DSCG and cationic polymers afford precipitates of DSCG—polymer aggregates. The nonionic polymers were classified into three categories according to their functional groups: polyols, polyamides and polyethylene glycols. Polyols consists of a large variety of different polymers such as polyalcohols, modified cellulose and other polysaccharides. Polyamides, consist of polyacrylamide (PAAm) and poly N-isopropylacrylamide (Poly-NIPAAm).

Polyvinyl Alcohol.

Figure 4:
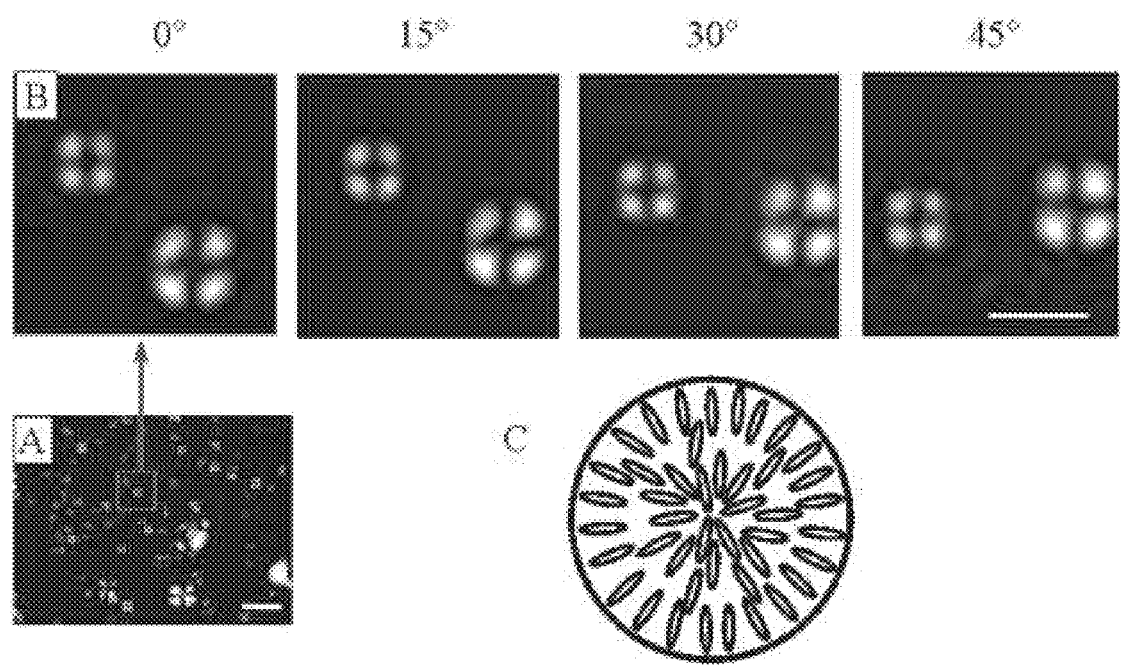
FIGS. 4A-4C depict the following: (A) Micrograph images of 6.4 wt % of DSCG and 10.9 wt % of PVA ($M_w$=89-98 K) in water between crossed polarizers. Scale bar=38 μm. (B) Enlarged images of the birefringent droplets at different orientations relative to the crossed polarizers. Scale bar=9.5 μm. Spacer thickness ~42 μm. (C) Schematic representation of the radial droplet configuration.

When mixed with polyvinyl alcohol (PVA), DSCG molecules formed an emulsion containing birefringent droplets at a concentration as low as 6 wt %, which is significantly lower than the concentration (11 wt %) required for liquid crystal phase in pure deionized water. In order to assist solubilization of PVA, the mixture of PVA, DSCG and water was heated to 90° C. and cooled to ambient temperature. The PVA remained dissolved when brought back to ambient temperature (Stauffer, S. R. et al, N. A. *Polymer* 1992, 33, (18), 3932-6). In order to achieve a stable emulsion, the sample was shaken vigorously on a vortex, and aged for 2 days; after which the sample was shaken again on a vortex. The solution at this stage appeared to be hazy and non-transparent, and contained an emulsion of liquid crystal droplets that were stable for at least one month on the shelf. FIG. 4 shows the optical micrograph of 6.4 wt % DSCG mixed with 10.9 wt % PVA ($M_w$=89-98K) with a 42 μm-thick spacer. Under crossed polarizers, this sample exhibited birefringent droplets in the shape of spheres with a cross image in each droplet. By rotating the sample under the crossed polarizers, there was no observable change in the cross images of the droplets. This result is consistent with the strong anchoring of the liquid crystal molecules on the surface of the droplets having a radial configuration—in which the optical axis of the liquid crystals orients perpendicular to the surface of the spherical droplet with a single topological point defect in the center of the droplet. Assuming that the dispersed droplets do not contain any polymer, and that a minimum concentration of 11 wt % of DSCG in deionized water is required to afford birefringence (Lee, H. et al., Phase diagram and thermodynamic properties of disodium cromoglycate-water lyomesophases. *Mol. Cryst. Liq. Cryst.* 1983, 91, (1-2), 53-8), the concentration of DSCG in each droplet should be at least 11 wt % or higher, which implies that the concentration of water in each droplet should be 89 wt % or lower. Comparing to the total concentration of DSCG and PVA used, this composition of the carrier phase corresponds to 26.1 wt % of PVA and 73.9 wt % of water in the emulsion. It is noted that the dispersed droplets likely contain a fraction, perhaps relatively small amount, of solvated polymers with DSCG molecules, this estimate of water content nevertheless serve to indicate a high content of water in the liquid crystal droplets. This high content of water in the droplets in an emulsion system is unusual and the detailed ternary phase diagram for this emulsion system is the subject of our ongoing research. It is further noted that in spite of being non-viscous, a solution of 10.9 wt % of PVA and 6.4 wt % of DSCG gives rise to stable droplets. This result indicates that the viscosity does not seem to play a primary role in stabilizing this water-in-water emulsion.

Polyacrylamide.

Figure 5:
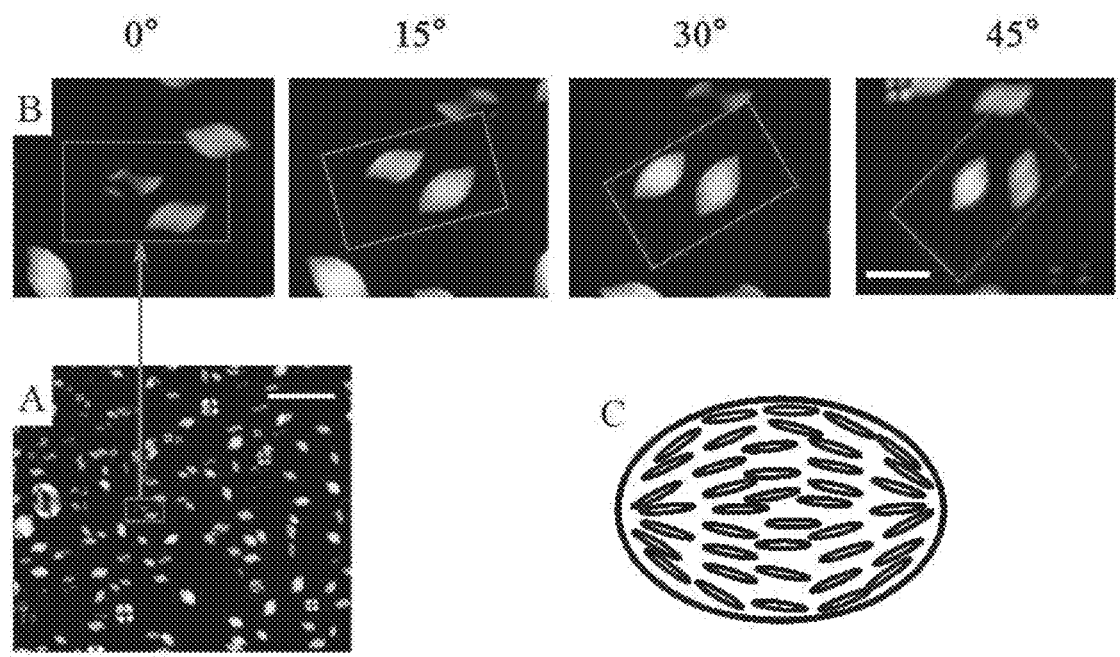
FIGS. 5A-5C depict the following: (A) Micrograph images (between crossed polarizers) of 8 wt % DSCG and 12 wt % PAAm (Mw=10K); scale bar=38 μm. (B) Enlarged images of the birefringent droplets at different orientations are shown; scale bar=7.6 μm. Spacer thickness ~42 μm. (C) Schematic representation of the bipolar droplet configuration in the shape of a prolate spheroid.

When mixed with polyacrylamide, DSCG molecules formed an emulsion solution with birefringent droplets immediately after mixing the solution on a vortex. FIG. 5 shows the micrograph images of 8 wt % DSCG and 12 wt % PAAm (Mw=10K) in water between crossed polarizers. The sample consisted of mostly ellipsoidal droplets and a few birefringent circles with a cross image. It is noted that past examples of liquid crystals droplets with non-spherical shape can have cusps affording shapes that are named tactoids (Bernal, J. D. et al., *J. Gen. Physiol.* 1941, 25, 111-20, 120-46; Nastishin, Y. A. et al., *Phys. Rev. E: Stat., Nonlinear, Soft Matter Phys.* 2005, 72, (4-1), 041711/1-041711/14). However, the present results show that, as the samples are rotated under the crossed polarizers, the droplets possess smooth curvature at the poles of the ellipsoids. The pattern of the modulation was consistent with a bipolar configuration where the molecules of the liquid crystal align parallel to the surface of the droplet, and with two topological defects located at the two polar ends of the ellipsoid that have the highest surface curvature (FIG. 5C). Assuming that the concentration of DSCG in the droplets is 11 wt % (89% water)—the same as that required to afford birefringence without the polymer in pure water (Lee, H. et al., Phase diagram and thermodynamic properties of disodium cromoglycate-water lyomesophases. *Mol. Cryst. Liq. Cryst.* 1983, 91, (1-2), 53-8)—and that the droplets do not contain any polymer, the composition of the carrier phase corresponds to 44 wt % of PAAm and 56 wt % of water.

Two kinds of ellipsoidal droplets are possible. One is a compressed sphere giving a disc-like "oblate spheroid," the other one is a stretched sphere giving a rod-like "prolate spheroid" (Drzaic, P. S., *Liquid Crystal Dispersions*. Wiley-Interscience: Singapore, 1995; Vol. 1). The present result is consistent with prolate spheroids having an average dimension of 25±4 μm in the long axis and 15±4 μm in the short axis. This ellipsoidal shape of the droplets in the PAAm solution likely reflects a state of liquid crystal orientation between weak and strong anchoring of liquid crystal on the surface. For the weak anchoring of liquid crystal, the alignment is dominated by the director in the bulk and is less affected by the surface chemistry (Drzaic, P. S., *Liquid Crystal Dispersions*. Wiley-Interscience: Singapore, 1995; Vol. 1). For the strong anchoring on the surface, the liquid crystal droplet assumes a spherical shape to minimize their surface areas, and thus surface energy (Drzaic, P. S., *Liquid Crystal Dispersions*. Wiley-Interscience: Singapore, 1995; Vol. 1).

A comparison in the order of magnitudes between the elastic energy in the liquid crystal droplets and the surface energy of the droplets also indicates that, for a liquid crystal droplet to have non-spherical shape due to the elastic strain of the liquid crystal, the interfacial tension between the lyotropic liquid crystal droplet and the carrier polymer solution should be very low. The elastic energy of liquids is of the order of KR, where K is the Frank's elastic constant and R is the radius of the droplet (Lavrentovich, O. D., *Liq. Cryst.* 1998, 24, (1), 117-125; Frank, F. C. *Faraday Discuss.* 1958, No. 25, 19-28). Whereas the surface energy of the droplet is of the order of $\gamma R^2$, where γ is the interfacial tension (Heimenz, P. C., *Principles of Colloid and Surface Chemistry: Revised and Expanded*. 2 ed.; Marcel Dekker: New York, 1986; p 815). Thus for the elastic strain to have an effect large enough to distort the droplet from being spherical, the interfacial tension γ must be very small in comparison with the Frank's elastic constant, K. Thus the prolate ellipsoid observed in DSCG droplets should have a very low interfacial tension, γ, in comparison with the Frank's elastic constant, K.

For the few droplets that showed cross images, the birefringence did not change as the sample was rotated under the crossed polarizers. Two possible droplet configurations can give rise to this observation. One possibility is a radial configuration that is different from the rest of the droplets. The other possibility is the same bipolar configuration mentioned above, but with the symmetry axis of the droplets aligned parallel to the path of the light (i.e., perpendicular to the crossed polarizers). In order to distinguish between these two possibilities, a liquid crystal cell was made whose space was sufficient enough to contain both the liquid crystal sample and some air. In this experiment, the liquid crystal could flow right after the liquid crystal cell was assembled and placed under the microscope. By monitoring the birefringence of the droplets as they flowed in the sample, it was observed that the birefringence of the droplets with cross images did change, showing the characteristics of a bipolar configuration. This result shows that PAAm supports exclusively the bipolar configuration of droplet formed by water solvated DSCG.

These bipolar droplets are not as stable as the radial droplets supported by PVA. When observed under a microscope over the course of 24 hours, these droplets grew to an average size of 36 and 25 µm (from 25 and 15 µm) in the two axes of the prolate spheroid. Furthermore, after aging two days in a vial, the emulsion of PAAm-dispersed DSCG phase separated into two layers. The top layer was transparent and the bottom layer was hazy, containing a birefringent liquid crystal phase.

Poly(ethylene glycol).

For poly(ethylene glycol) (PEG, $M_w$=600 and 1,500), neither emulsion droplets nor birefringence was observed in the solution over the entire range (7.6 wt %-8.1 wt %) of mixture composition. Oligo or poly(ethylene glycol) can have a high affinity to chelate metal ions (Artz, S. P. et al., *J. Am. Chem. Soc.* 1984, 106, (7), 2160-71; Cram, D. J. et al., *J. Am. Chem. Soc* 1981, 103, (20), 6228-32). For instance, it has been established that macro-cyclic ethylene glycols (crown ether) can effectively form complexes with cations such as potassium and sodium (Artz, S. P. et al., *J. Am. Chem. Soc.* 1984, 106, (7), 2160-71; Cram, D. J. et al., *J. Am. Chem. Soc* 1981, 103, (20), 6228-32). Because DSCG contains sodium ions, the oxygen atoms of polyethylene glycol chains can complex with the sodium ions of DSCG. At high concentrations of the ethylene glycol units, this complexation can lead to a competitive sequestering of sodium ions from the DSCG mesophase providing an enhanced solvation of the DSCG molecules and destroying the self-association of DSCG that is responsible for forming the liquid crystal phases (Ding, X. S. et al., *J. Pharm. Sci.* 2004, 93, (5), 1351-1358; Attwood, T. K. et al., *Mol. Cryst. Liq. Cryst., Lett. Sect.* 1986, 4, (1), 9-14).

Polyanions.

Figure 6:
FIGS. 6A-6C depict the following: Micrograph images of DSCG as a liquid crystal splash in a solution of polyanions, (A) PAA-Na, (B) PMA-Na, and (C) PSS-Na. Scale bar=76 μm.

Other classes of water-soluble polymers-polyanions and polycations—do not give stable droplets. For all three polyanions, PSS, PAA-Na and PMA-Na, liquid crystal phases mixed with isotropic solution were observed. These liquid crystal phases do not disperse into droplets (FIGS. 6A-6C). Because the carboxylic ions of DSCG are more similar in properties to the negative charges of the polyanions than the functional groups of polyamides or polyols, the polyanions can be more miscible with the liquid crystal phase of DSCG, allowing the co-existence of a mixture of liquid crystal and isotropic phases.

Polycations.

When mixed with DSCG, Poly(allylamine hydrochloride) (PAH) affords a solution with precipitates, and poly(ethyleneimine) (PEI) affords a yellow gel. No birefringence was observed in either the precipitate, the clear solution, or the gel phase. Thus, polycations appear to disrupt the formation of mesophase by DSCG molecules. This result is attributed to the chemical reaction of salt formation between the two negative charges of DSCG and the polycations. Because of the multivalent nature of the positive charges on the polymer, the polycations have a high propensity to react with the carboxylic anions on the DSCG molecules and hence displace the sodium ions into the solution. This reaction between the DSCG and polycations overcome the molecular interactions between the DSCG molecules that give rise to the mesophase. Together, these results suggest that, in general, only non-ionic water-soluble polymers, except poly(ethylene glycol), support water-solvated DSCG to form stable droplets in water.

Recently there was a finding that there is an extra energy penalty associated with the coalescence of liquid crystal droplets, which will be absent should the droplets be isotropic (Terentjev, E. M., *Europhys. Lett.* 1995, 32, (7), 607-12). From a physical point of view, the present results are fully consistent with this topological stabilization of liquid crystal droplets. Especially, the radial alignment is more stable than the tangential alignment. This "topological stabilization" is indeed fundamental and interesting, but does not concern the chemical functional groups in each of the liquid crystals. However, the present results clearly demonstrate that the nature of the chemical functional groups plays a critical role on maintaining the stability of the emulsion. Below is an analysis on the chemical origin which accounts for the stability of this water-in-water emulsion.

Figure 7:
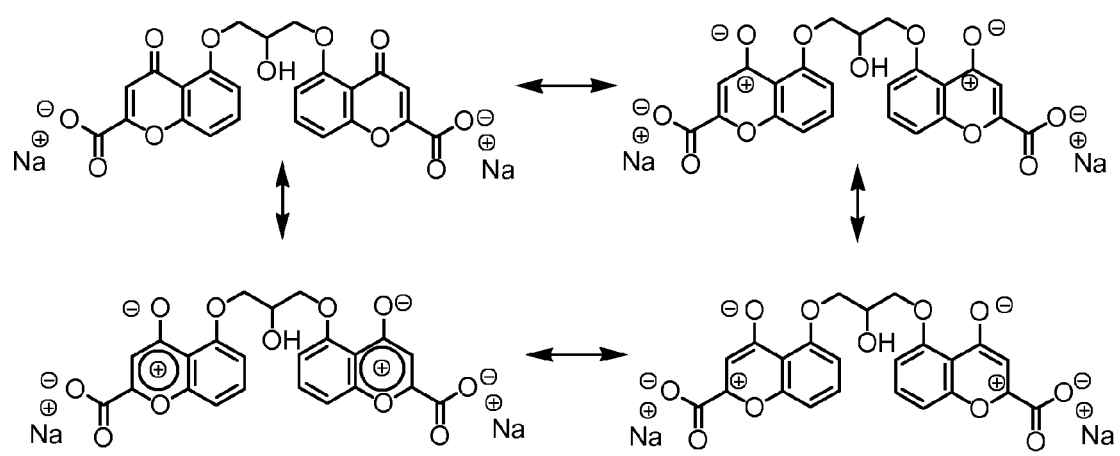
FIG. 7 is a schematic showing that the resonance structures of DSCG give rise to an increased characteristic of aromaticity in the hetero-atom rings.

While traditional lyotropic liquid crystals formed by surfactants in water are driven by hydrophobic interactions (Tanford, C., *The hydrophobic effect: Formation of micelles and biological membranes*. Wiley-Interscience: New York, 1980; Collings, P. J.; Patel, J. S.; Editors, *Handbook of Liquid Crystal Research*. 1997; p 600 pp), examining the molecular structure of DSCG indicates a different set of molecular interactions are responsible for the liquid crystal phases of DSCG. The possible molecular interactions between the DSCG molecules in an aqueous solution likely consist of (a) $\pi$-stacking ($\pi$-$\pi$* dispersion interactions) arising from the stacking of the fused aromatic rings of the DSCG molecules, (b) salt bridge formation by the carboxylic sodium salts at the periphery of the molecules, and (c) hydrogen bonds from the hydroxyl group at the center of the molecule. It is further noted that there exists a partial aromaticity in the heteroatom ring of the DSCG molecule (FIG. 7). As the resonance structure of the carbonyl group in this ring generates a positive charge, the heteroatom ring becomes a cyclic 6-$\pi$ electron system, and consequently becomes aromatic. This resonance structure further stabilizes the positive charge in the ring, which affords a charge separation that increases the polarizability of individual DSCG molecules and the dispersion forces between the molecules. Because the dispersion force is generally considered to be the most significant contribution for the formation of liquid crystals, it is believed that this increased polarizability plays an important role for DSCG to self-associate to form liquid crystal phases.

In contrast, hydrogen bonds are the predominant molecular interactions for polyols and polyacrylic amides in the solution. Although these hydrogen bonds also have an affinity for the carbonyl and the hydroxyl groups of DSCG, the overall thermodynamic partitioning of all molecular interactions (salt bridges, $\pi$-stacking of the aromatic rings, and hydrogen bondings) will determine the phase behavior of the ternary system (DSCG, polymer and water). As DSCG molecules self-associate to form liquid crystal aggregates or droplets, the hydrogen bonds between the solvated polymer and the surface of the droplets become polyvalent in nature, and thus prevent further sequestering of individual DSCG molecules into the droplet. This polymer binding on the surface of the droplet in turn presents a steric stabilization between the droplets that is similar to the mechanism accounting for the prevention of flocculation of solid colloids (Sato, T. et al., *Stabilization of Colloidal Dispersions by Polymer Adsorption*. 1980; p 155; Meier, D. J. *Journal of Physical Chemistry* 1967, 71, (6), 1861-8).

Because DSCG molecules on the surface of the liquid crystal droplets are mobile, the propensity for the polymers to form hydrogen bonds with the DSCG molecules is critical for determining the orientation of DSCG mesogens on the droplet surface. Examining the properties between polyols and polyacrylic amides, the aim is to identify the major difference in each of their interactions with DSCG molecules that may account for the different droplet configurations. Surprisingly, documented acidities of a hydroxyl group and a primary amide group are very close (Ballinger, P. et al., *J. Am. Chem. Soc.* 1960, 82, 795-8). Thus, it is believed that electrostatic interaction between the polymer and DSCG is not a determining factor for the different droplet configurations. However, with a given hydrogen bond acceptor, hydroxyl groups in general form much stronger hydrogen bonds than primary amide bonds (Luk, Y.-Y. et al., *Surf. Sci.* 2004, 570, (1-2), 43-56). In the light of this difference in hydrogen bonding strength, other polyols were examined, including pullulan, and hydroxypropyl cellulose (HPC), and one additional polyamide, poly N-isopropylacrylamide (PNIPAAm). While all of the polyols afforded DSCG droplets with radial configuration, PNIPAAm, a polyamide, afforded droplets with tangential alignment (bipolar configuration) of DSCG on the surface. This result suggests that strong hydrogen bonding from the polymer solution tends to afford DSCG droplets with radial configuration, whereas weak hydrogen bonding facilitates DSCG droplets with tangential configurations. It is also interesting to note that the interfacial chemistry giving rise to less stable droplets have a droplet configuration (tangential alignment) that is also expected by the "topological stabilization" to be less stable (Terentjev, E. M., *Europhys. Lett.* 1995, 32, (7), 607-12).

Conclusion

While aqueous solutions of DSCG below 11 wt % do not exhibit birefringence at ambient temperature (~22° C.), the presence of non-ionic polymers induces the formation of liquid crystal droplets of DSCG in water at a concentration as low as 6 wt % (DSCG). The functional groups on the polymers determine both the stability of liquid crystal droplets and the orientation of the liquid crystals at the interface (i.e., droplet configuration). The functional groups of a polymer in the continuous aqueous medium also determine the stability and the configuration of the liquid crystal droplets. While polyethers do not afford observable liquid crystal droplets, polyalcohols support the formation of a stable emulsion of water solvated DSCG droplets with radial configurations and polyamides afford a tangential configuration. Polyanions appear to be miscible with DSCG to form a mixture of isotropic and anisotropic phases without the formation of droplets. Polycations do not afford any birefringence when mixed with DSCG. Collectively, these results indicate that the nature of the molecular interactions between the polymer and the DSCG determine both the droplet stability and the liquid crystal orientation at the surface of the droplet. The stability of droplets appears to be maintained by a partition between the molecular interactions in the bulk of the liquid crystal (π-stacking and salt bridge formation) and at the interface (hydrogen bonding) between the polymers and the DSCG while all of these molecular interactions are solvated in water. This work shows that emulsion systems consisting of non-amphiphilic molecules are possible. Considering the vast variety of molecular interactions apart from hydrophobic interactions, rational design of water-in-water emulsion should be possible. Because the liquid crystal phase comprised of DSCG molecules does not disrupt specific protein-protein binding events, (Luk, Y.-Y. et al., *Chem. Mater.* 2005, 17, (19), 4774-4782) polymer dispersed lyotropic liquid crystal is compatible with research that requires the partitioning of different biological molecules. Furthermore, by cross-linking the polymers, this water-in-water emulsion can provide a new hydrogel system embedded with liquid crystals that can be responsive to external stimuli.

Example 2

Water-in-Water Emulsion to New Hydrogel

New Colloidal Science: Water-in-Water Emulsion of Chromonic Liquid Crystals.

Figure 8:
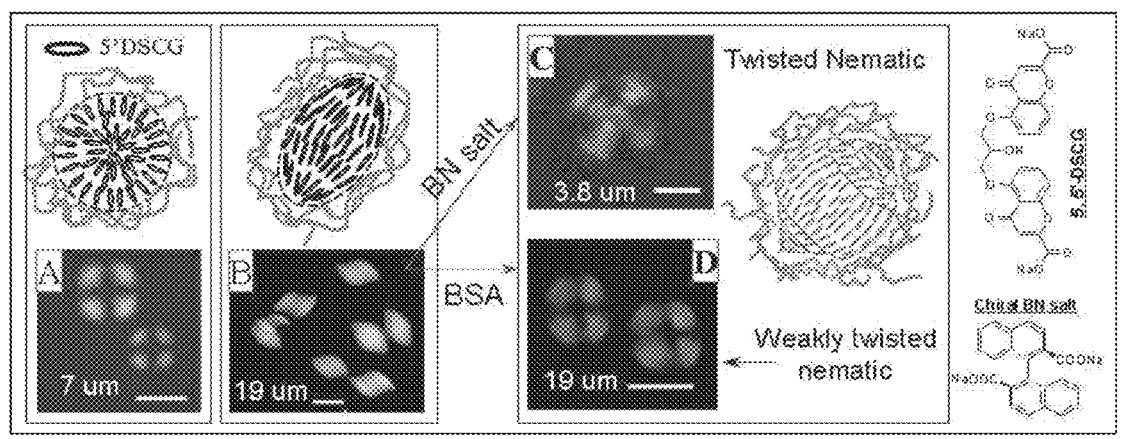
FIGS. 8A-8D are images under crossed polars and schemes of fundamentally new water-in-water emulsion. (A) 10.9 wt % polyvinyl alcohol & 6.4 wt % DSCG; DSCG liquid crystals align perpendicular to the droplet surface. (B) 12 wt % polyacrylamide & 8 wt % DSCG, DSCG aligns parallel to droplet surface. (C) 4 wt % binaphthyl (BN) salt, and (D) 0.5 wt % of BSA protein added into the system of (B), the liquid crystal adopts onion configuration (cholesteric phase) with twisting orientation of each layer of molecules for system (C) and (D).

The present approach to making biocompatible novel structure involves making protein-laden hydrogel based on a recently discovered water-in-water emulsion (FIG. 8) (Simon, K. A., P. Sejwal, R. B. Gerecht, and Y.-Y. Luk, Water-in-Water Emulsions Stabilized by Non-Amphiphilic Interactions: Polymer-Dispersed Lyotropic Liquid Crystals. Langmuir, 2007. 23(3): p. 1453-1458), where droplets of water-solvated liquid crystal—disodium cromoglycate (DSCG), can be stabilized from coalescence in water by the presence of certain water-soluble polymers (polyacrylamides and polyols). Traditional water-in-water emulsions involve having different biopolymers preferentially partition with its own type and forming different phases in the common solvent-water (Poortinga, A. T., Microcapsules from Self-Assembled Colloidal Particles Using Aqueous Phase-Separated Polymer Solutions. Langmuir, 2008. 24(5): p. 1644-1647; Spagna, G., R. N. Barbagallo, P. G. Pifferi, R. M. Blanco, and J. M. Guisan, Stabilization of a beta-glucosidase from *Aspergillus niger* by binding to an amine agarose gel. J. Mol. Catal. B: Enzym., 2000. 11(2-3): p. 63-69; Tolstogusov, V. B., Thermodynamic Incompatibility of Food Macromolecules, in Food Colloids and Polymers: Stability and Mechanical Properties, E. Dickinson and P. Walstra, Editors. 1993, Royal Socieity of Chemistry: Cambridge, U. K. p. 94-102; Tolstoguzov, V., Thermodynamic aspects of biopolymer functionality in biological systems, foods, and beverages. Critical Reviews in Biotechnology, 2002. 22(2): p. 89-174; Tolstoguzov, V., Texturising by phase separation. Biotechnology Advances, 2006. 24(6): p. 626-628). In contrast, the present work shows that small molecules (e.g., DSCG) can also exhibit water-in-water emulsion phenomena. The orientation of the liquid crystals (DSCG molecules) in the droplets is controlled by the chemistry of the polymer (FIGS. 8A-8B) and can respond to the presence of chiral additives or proteins giving rise to novel chiral droplets (FIGS. 8C-8D), providing a fertile ground for new studies in soft condensed matter (Poulin, P., Novel phases and colloidal assemblies in liquid crystals. Current Opinion in Colloid & Interface Science, 1999. 4(1): p. 66-71). The mechanism for stabilizing the emulsion in the system of the present invention is fundamentally different from the traditional water-in-water (W/W) emulsion. Only thermodynamic incompatibility of different biopolymers is responsible for the traditional water-in-water emulsion (Tolstogusov, V. B., Thermodynamic Incompatibility of Food Macromolecules, in Food Colloids and Polymers: Stability and Mechanical Properties, E. Dickinson and P. Walstra, Editors. 1993, Royal Socieity of Chemistry: Cambridge, U. K. p. 94-102; Tolstoguzov, V., Thermodynamic aspects of biopolymer functionality in biological systems, foods, and beverages. Critical Reviews in Biotechnology, 2002. 22(2): p. 89-174). But, for the present system, in addition to the incompatibility of different types of molecular interactions, including dispersion forces (pi-stacking), hydrogen bonding, and salt bridges entirely solvated in water, multivalent binding between the polymer and DSCG molecules on the surfaces of the droplets also arise to prevent coalescence and Ostwald ripening of the droplets. This polymer coating on liquid crystal droplets is fundamentally new and is extremely useful for working with proteins because the whole system (polymer and DSCG) does not denature proteins (Luk, Y.-Y., C.-H. Jang, L.-L. Cheng, B. A. Israel, and N. L. Abbott, Influence of lyotropic liquid crystals on the ability of antibodies to bind to surface-immobilized antigens. Chemistry of Materials, 2005. 17(19): p. 4774-4782). A 3-component (water, DSCG and polyacrylamide) phase diagram shows that the water-in-water emulsion exists with a concentration of DSCG from 3-12 wt %. Previous study has shown that high concentration of DSCG (11 wt % in water) in liquid crystal phase does not disrupt the specific binding between antigen and antibody (Luk, Y.-Y., C.-H. Jang, L.-L. Cheng, B. A. Israel, and N. L. Abbott, Influence of lyotropic liquid crystals on the ability of antibodies to bind to surface-immobilized antigens. Chemistry of Materials, 2005. 17(19): p. 4774-4782).

Making Porous Hydrogel with Immobilized Proteins Preferably Located Towards and on the Pore Surfaces.

Many methods exist for making porous hydrogel (Park, K., Superporous hydrogels for pharmaceutical and other applications. Drug Delivery Technology, 2002. 2(5): p. 38, 40-44; Park, K., J. Chen, and H. Park, Superporous hydrogel composites: A new generation of hydrogels with fast swelling kinetics, high swelling ratio and high mechanical strength. Polym. Drugs Drug Delivery Syst. FIELD Full Journal Title: Polymeric Drugs & Drug Delivery Systems, 2001: p. 145-155; Woerly, S., Porous hydrogels for neural tissue engineering. Mater. Sci. Forum 1997. 250: p. 53-68). Also, there have been reports of using traditional lyotropic liquid crystal assemblies as templates and as polymerizable scaffold for the fabrication of new materials (Gin, D. L., J. E. Bara, R. D. Noble, and B. J. Elliott, Polymerized lyotropic liquid crystal assemblies for membrane applications. Macromol. Rapid Commun., 2008. 29(5): p. 367-389; Gin, D. L., X. Lu, P. R. Nemade, C. S. Pecinovsky, Y. Xu, and M. Zhou, Recent advances in the design of polymerizable lyotropic liquid-crystal assemblies for heterogeneous catalysis and selective separations. Adv. Funct. Mater., 2006. 16(7): p. 865-878; Mueller, A. and D. F. O'Brien, Supramolecular Materials via Polymerization of Mesophases of Hydrated Amphiphiles. Chem. Rev. (Washington, D.C.), 2002. 102(3): p. 727-757; O'Brien, D. F., B. Armitage, A. Benedicto, D. E. Bennett, H. G. Lamparski, Y.-S. Lee, W. Srisiri, and T. M. Sisson, Polymerization of Preformed Self-Organized Assemblies. Acc. Chem. Res., 1998. 31(12): p. 861-868; Gin, D. L. and W. Gu, Nanoporous catalytic materials with organic frameworks. Adv. Mater. (Weinheim, Ger.), 2001. 13(18): p. 1407-1410; Gin, D. L., W. Gu, B. A. Pindzola, and W.-J. Zhou, Polymerized Lyotropic Liquid Crystal Assemblies for Materials Applications. Acc. Chem. Res., 2001. 34(12): p. 973-980; Nguyen, S. T., D. L. Gin, J. T. Hupp, and X. Zhang, Supramolecular chemistry: functional structures on the mesoscale. Proc. Natl. Acad. Sci. U.S.A., 2001. 98(21): p. 11849-11850; Noble, R. D., D. L. Gin, D. Camper, J. Bara, X. Zeng, and C. Koval, Design and characterization of novel membrane materials from imidazolium-based room temperature ionic liquids and liquid crystal structures. PMSE Prepr., 2006. 95: p. 267).

However, using water-in-water emulsion as template for making materials is new, and the system retains the activity of the proteins involved in the synthesis of the materials. Extending from the discovery of water-in-water emulsion, it was discovered that porous hydrogel with shell-like morphology can be created by polymerizing and cross-linking the monomers (acrylamide) in situ with the presence of DSCG, in which pores of encapsulated DSCG molecules are coated by a layer of cross-linked polymers. Subsequently, the DSCG molecules can be readily removed from the hydrogel matrix through diffusion out of the gel materials (essentially a dialysis) by soaking the sample in excess of water (FIG. 9). Scanning electron microscopy reveals a connected shell structure (instead of a Swiss cheese morphology) in the hydrogel materials (FIG. 10) supporting the notion of polymer coating on the droplets. In this particular embodiment, the pore size ranges from 20-40 μm in diameter, which can facilitate the rapid transport of proteins as well as bacteria (~1 μm) and mammalian cells (10-30 μm).

Example 3

Microcapsule Hydrogel

Because the water-in-water (W/W) emulsion of 5'DSCG differs from known W/W emulsion of biopolymers in that polymer coatings on the liquid crystal droplets are required, it was envisioned that this water-in-water emulsion offers new knowledge in colloidal science, and many new phenomena can be explored. For instance, the general scheme of porous hydrogel formation based on W/W emulsions (FIG. 9) suggests that the density of the polymer is higher on the DSCG droplet than in the bulk solution. Thus, if sufficiently less monomers and cross-linkers is used, the higher concentration of the monomers and crosslinkers close to the droplet surface will be polymerized and crosslinked on the droplets rather than in the bulk. Such selective polymerization should result in a novel core-shell structure of hydrogel material. By decreasing the concentration of monomers (acrylamide) used for making porous hydrogel from 6 wt % to 4 wt % and that of cross-linkers from 0.051 wt % to 0.02 wt %, core-shell structures of ellipsoidal shapes were obtained as shown by transmission electron microscopy (FIG. 11). These elongated microcapsules possess critical features that are required for making artificial cells (Chang, T. M. S., Therapeutic applications of polymeric artificial cells. Nat. Rev. Drug Discovery, 2005. 4(3): p. 221-235; Miller, O. J., K. Bemath, J. J. Agresti, G. Amitai, B. T. Kelly, E. Mastrobattista, V. Taly, S. Magdassi, D. S. Tawfik, and A. D. Griffiths, Directed evolution by in vitro compartmentalization. Nat. Methods, 2006. 3(7): p. 561-570; Picart, C. and D. E. Discher, Materials science: Embedded shells decalcified. Nature (London, U. K.), 2007. 448(7156): p. 879-880; Rasmussen, S., L. Chen, D. Deamer, D. C. Krakauer, N. H. Packard, P. F. Stadler, and M. A. Bedau, Evolution: Transitions from nonliving to living matter. Science 2004. 303(5660): p. 963-965; Prakash, S., J. R. Bhathena, and H. Chen, Introduction to artificial cells: concept, history, design, current status and future. Artif. Cells, *Cell Eng. Ther.,* 2007: p. 3-14; Zhang, Y., W. C. Ruder, and P. R. LeDuc, Artificial cells: building bioinspired systems using small-scale biology. Trends Biotechnol., 2008. 26(1): p. 14-20), and bear the potential for a wide range of applications including drug delivery (Caruso, F., R. A. Caruso, and H. Moehwald, Nanoengineering of inorganic and hybrid hollow spheres by colloidal templating. Science, 1998. 282(5391): p. 1111-1114; Chang, T. M. S., Therapeutic applications of polymeric artificial cells. Nat. Rev. Drug Discovery, 2005. 4(3): p. 221-235; Prakash, S., J. R. Bhathena, and H. Chen, Introduction to artificial cells: concept, history, design, current status and future. Artif. Cells, Cell Eng. Ther., 2007: p. 3-14; Zhang, Y., W. C. Ruder, and P. R. LeDuc, Artificial cells: building bioinspired systems using small-scale biology. Trends Biotechnol., 2008. 26(1): p. 14-20; Wang, Y., S. Gao, W.-H. Ye, H. S. Yoon, and Y.-Y. Yang, Co-delivery of drugs and DNA from cationic core-shell nanoparticles self-assembled from a biodegradable copolymer. Nat. Mater., 2006. 5(10): p. 791-796; Cleland, J. L. and D. I. C. Wang, Refolding and aggregation of bovine carbonic anhydrase B: quasi-elastic light scattering analysis. Biochemistry, 1990. 29(50): p. 11072-8; Zelikin, A. N., Q. Li, and F. Caruso, Degradable polyelectrolyte capsules filled with oligonucleotide sequences. Angew. Chem., Int. Ed., 2006. 45(46): p. 7743-7745; Prakash, S. and T. M. S. Chang, Microencapsulated genetically engineered live *E. coli* DH5 cells administered orally to maintain normal plasma urea level in uremic rats. Nat. Med. (N.Y.), 1996. 2(8): p. 883-887).

First, the inside and outside of these μm-sized hydroshells are both hydrophilic. Second, the diffusion of reagents in and out of the capsule is highly efficient because of the swelling property of the hydrogel. Third, there is a density gradient in the gel material from the interior surface extending to the outer surface of capsule, which can potentially be engineered with functional groups for active control of transport. Fourth, the immobilization of proteins will likely occur preferentially on the interior surface of the capsules and with preferred orientations.

Here, there will be a focus on characterization of the location and activity of immobilized enzyme on this class of hydro-shells.

In addition, it is hypothesized that a bicontinuous phase consisting of liquid crystal phase and polymer isotropic solution (instead of polymer dispersed liquid crystal droplets) will be obtained by controlling the parameters such as the amount of DSCG relative to the monomers, and the propensity for the polymer to coat the droplets. The structures, properties, and catalytic activities of this bicontinuous materials will also be characterized.

The preposition for the formation of W/W emulsion and synthesis of porous hydrogel is due to thermodynamic incompatibility of molecules in water and polymer coating on surfaces of the droplets. These two mechanisms suggest that other structures, beside porous hydrogel, can be made by simply varying the experimental parameters of the synthesis such as the percentage of liquid crystal molecules, the crosslinker and the monomer, as well as the chemical structure of the gel materials. It has been demonstrated that by decreasing the concentration of the monomers and crosslinkers, isolated and elongated hydroshells can be obtained instead of porous hydrogel. Here, the preferred location of immobilized protein on microcapsule hydro-shell will be characterized. Because the density of the polymer coating decreases from the surface of the DSCG droplet outwardly to the bulk solution, a density gradient is created in the gel materials. To characterize the location of immobilized proteins on this density gradient of hydro-shell, FITC-tagged avidin will be immobilized on the hydro-shells and the fluorescent signal will be measured. Bovine serum albumin (BSA) will also be incorporated into the hydro-shell, then the hydro-shell will be treated with fluorescently tagged anti-BSA antibody. These experiments will (a) study the binding activity for immobilized antigen on hydro-shell, (b) infer on the diffusion of proteins in and out of the hydro-shell, and (c) corroborate the result from direct attachment of FITC-tagged avidin.

Example 4

Bicontinuous Hydrogel

Figure 12:
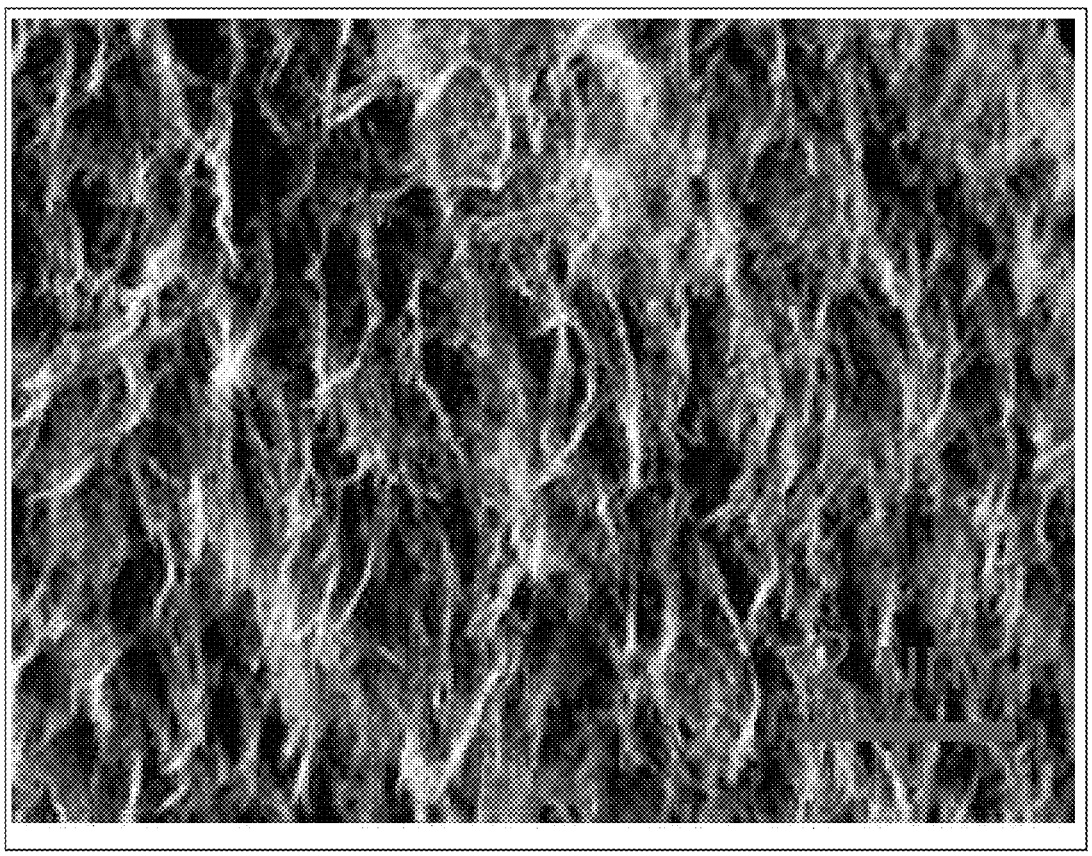
FIG. 12 is an SEM image of hydrogel prepared with 16 wt % AAm, 5 wt % NIPAM, 8.234 wt % DSCG.

Hydrogel with Bicontinuous structure. It is hypothesized that decreasing binding affinity of the polymer to the DSCG droplets can increase coalescence of the droplets to the point of forming a bicontinuous phase. For example, using a mixture of poly-N-isopropylacrylamide (polyNIPAM) and poly acrylamide achieves a hydrogel with a structure that highly resembles bicontinuous morphology (FIG. 12). Because such bicontinuous hydrogel provides enormous surface area that can be decorated with desired protein receptors or enzymes (Jang, J.-H., S. J. Jhaveri, B. Rasin, C. Koh, C. K. Ober, and E. L. Thomas, Three-Dimensionally-Patterned Submicrometer-Scale Hydrogel/Air Networks That Offer a New Platform for Biomedical Applications. Nano Lett., 2008. 8(5): p. 1456-1460; Kulyagin, O., T. Leizer, and M. S. Silverstein, Porous and bicontinuous hydrogel systems through emulsion templating. PMSE Prepr., 2008. 98: p. 754-755), this material has potential for improving or enabling a wide range of applications such as biosensor development and 3-dimensional cell culture. By controlling the amount of immobilized enzymes, measurements and comparisons will be made of the activity of immobilized aldolase on the isolated hydroshells and the bicontinuous hydrogel with those on the porous hydrogel.

Example 5

New Gel Materials Useful for Enhancing the Activity of Immobilized Enzymes

Apart from the advantage of reusability of enzymes immobilized on materials, the supporting materials also provide an opportunity to increase the activity of immobilized enzyme as compared to that of free enzymes in solution. The first hypothesis is that because the proteins are immobilized preferentially towards and on the surface of the pores of the hydrogel in the present method, and because the immobilization likely uses surface lysine residues that are not buried in the active site, there is an increased local concentration of the enzymes with preferred orientations that expose the active sites. Such control of protein orientation and local concentration likely will increase the catalytic efficiency as compared to that of free enzymes in solution. To test this hypothesis, measurements will be made of the activities of immobilized enzymes in comparison to that of free enzyme in solution. First, a measurement will be made of the amount of enzyme being immobilized on the hydrogel during one-pot fabrication using the Bradford assay to measure how much proteins have not been polymerized into the hydrogel and thus diffused out of the gel along with DSCG molecules. Second, a measurement will be made of the pseudo affinity constant ($K_m$) and maximum velocity ($V_{max}$) of the enzyme and the substrate by measuring the initial rate versus the substrate concentration. These two parameters will reflect the effect of immobilization of proteins on the hydrogel. Measurement will also be made of $V_{max}$ as a function of the amount of immobilized enzymes ([$E_T$]). Because the accessibility to the immobilized enzymes decreases from the surface of the pores to the inside of the hydrogel materials, it is expected that the maximum catalytic rate will plateau as the total concentration of enzyme increases, instead of the established linear relationship of $V_{max}=k_{cat}*[E_T]$ for free enzymes in a solution, where $V_{max}$ is the maximum rate of reaction and $k_{cat}$ is the turnover constant and $E_T$ is total concentration of enzymes.

Figure 13:
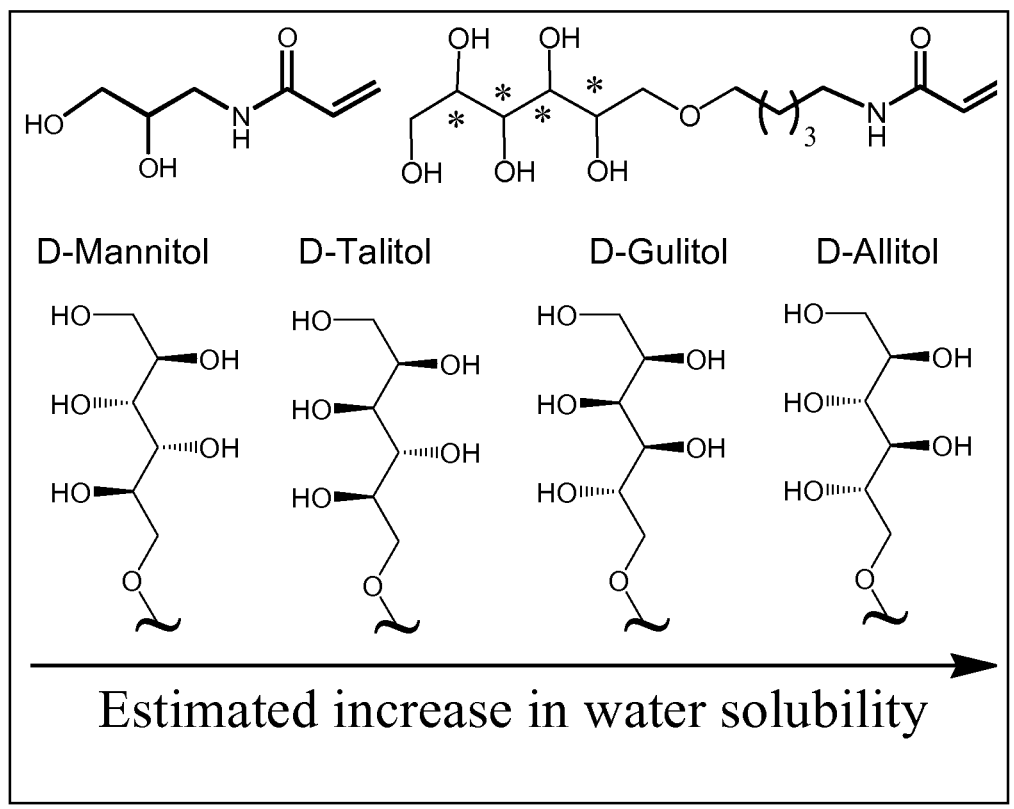
FIG. 13 depicts structures of proposed monomers for five new hydrogels.
Figure 14:
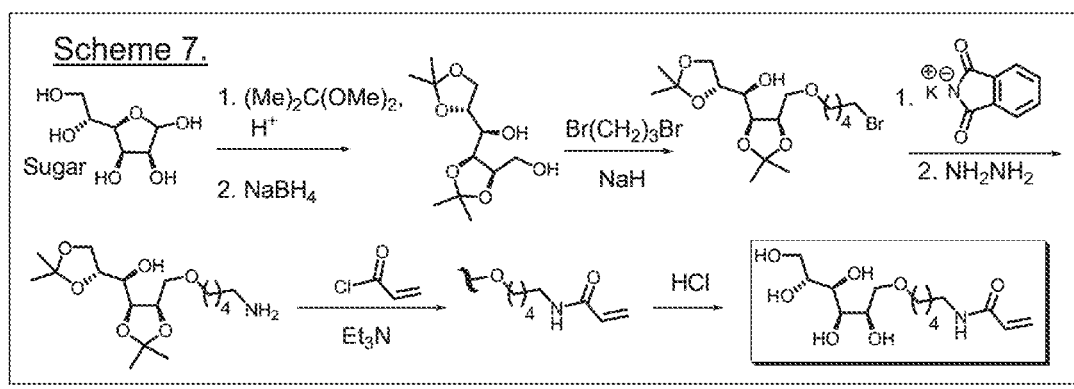
FIG. 14 depicts reaction schemes related to the preparation of protein-laden hydrogels.

A second hypothesis is that the gel materials can influence the enzymatic reaction by different mechanism. For example, in regions close to the surface of the gel materials, the equilibrium of substrate mannose can be shifted towards the active form for aldolase due to the low acidity of polyacrylic amide materials. To test this hypothesis, synthesis of four new hydrogel materials based on chiral polyol will be conducted (FIG. 13) and measurements will be made of the activity of aldolase and β-1,4-galactosyltransferase (β4Gal-T1) as a function of the gel materials. The types of polymers that can support water-in-water emulsions of DSCG are non-ionic, including polyacrylamides, polyols (Simon, K. A., P. Sejwal, R. B. Gerecht, and Y.-Y. Luk, Water-in-Water Emulsions Stabilized by Non-Amphiphilic Interactions: Polymer-Dispersed Lyotropic Liquid Crystals. Langmuir, 2007. 23(3): p. 1453-1458), and poly vinylpyrrolidone. A general synthetic scheme has been designed and validated for making chiral polyol-based hydrogels from different sugar molecules (FIG. 14). Starting with different sugars, four hydrogels with different stereochemistry of the hydroxyl pendent groups will be obtained. Because the substrate (peptide or protein) for β4Gal-T1 does not involve an equilibrium like mannose, the activity of aldolase and β4Gal-T1 will exhibit different dependence on the gel chemistry. The four diastereomers of the polyols on the synthesized hydrogels will provide a wide range of different properties including chiral microenvironment, water solubility and hydrogen bonding ability. As such, the present invention can be used to form the materials basis for achieving more difficult biological functions such as protein synthesis and post-translational modification.

Example 6

Biocatalytic Power of Protein-Laden Connected Hydro-Shell

As noted previously, many methods have been developed to immobilize proteins on materials. Here, research is considered to (i) study the effect of the chemistry of the gel material on enzymatic activity of immobilized proteins, (ii) tailor different microenvironments on the porous hydrogel for enabling the immobilized enzymes to have a higher catalytic activity than that of free enzymes in solution, (iii) provide a new one-pot method using water-in-water emulsion to make protein-immobilized hydrogel, and (iv) introduce a hierarchy in the novel structures of hydrogel allowing preferred location of immobilized proteins.

Immobilization of Protein on Preferred Location.

Figure 9:
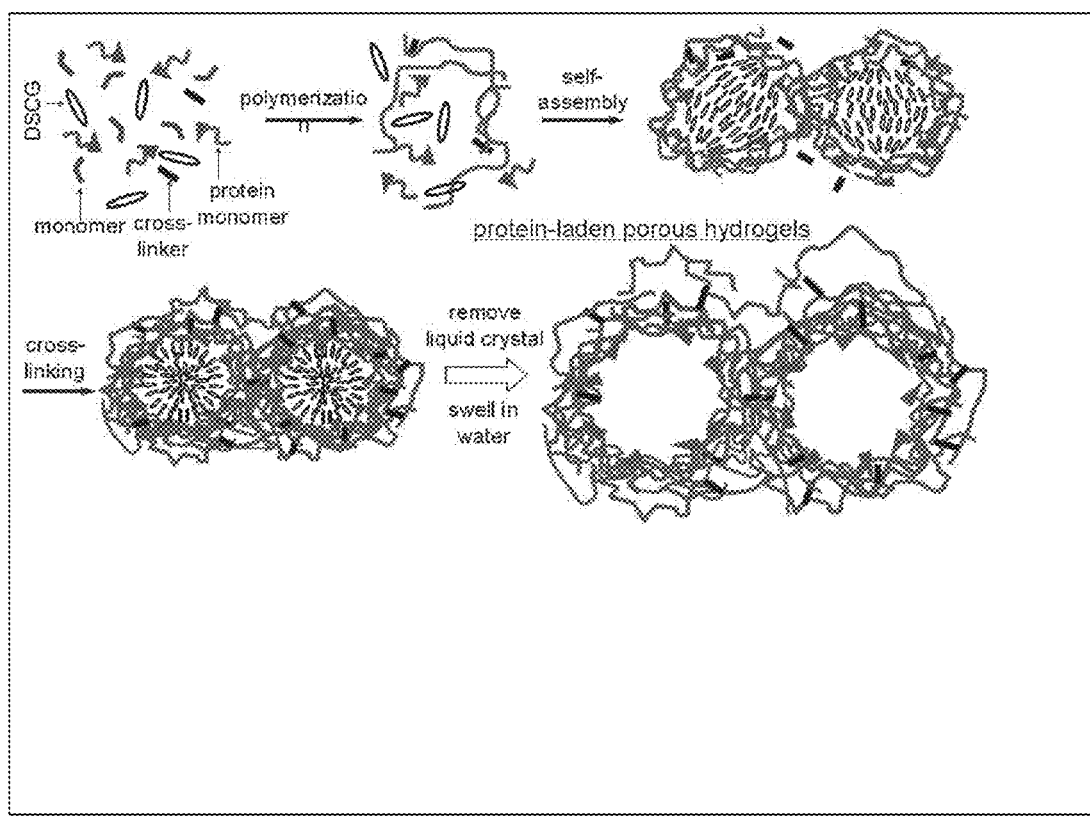
FIG. 9 is a schematic showing one-pot fabrication of protein-laden connected hydroshell: polymerization of monomers, phase separation forming polymer-dispersed LC droplets, cross-linking the polymer coating on LC droplets, removal of the 5' DSCG molecules through diffusion by soaking the sample in water.
Figure 15:
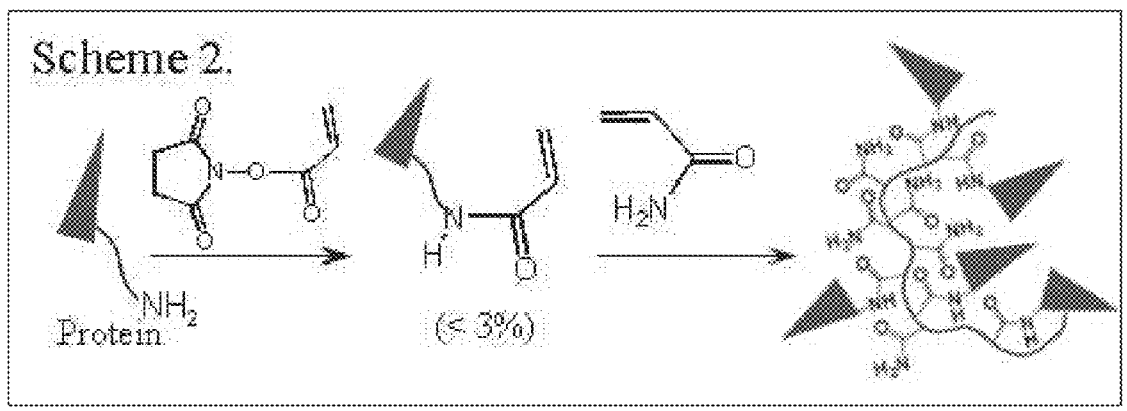
FIG. 15 depicts a reaction scheme related to the modification of proteins.
Figure 16:
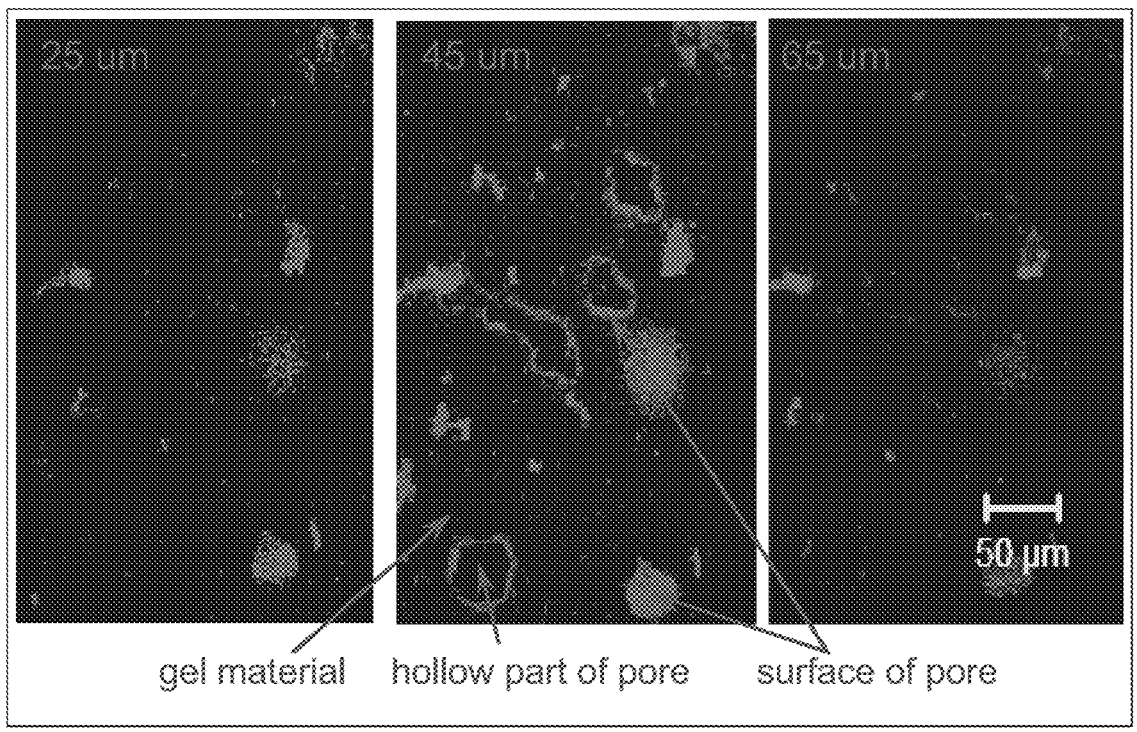
FIG. 16 is a confocal fluorescent image of porous hydrogel made by w/w emulsion, the confocal depth is shown in um.

Strikingly, when there is a protein modified with polymerizable moiety (FIG. 15) present in the pre-gel solution, the proteins are polymerized into the gel preferably towards and on the surface of the pores that are in contact with the DSCG molecules (FIG. 9). The chemistry for protein immobilization, modified from a previously reported method, uses the abundant lysine groups on a protein to coupled with N-succimidylacrylate in phosphate buffered saline (pH 7.4) to afford vinyl-modified proteins (FIG. 15) (Miyata, T., N. Asami, and T. Uragami, A reversibly antigen-responsive hydrogel. Nature (London), 1999. 399(6738): p. 766-769; Shoemaker, S. G., A. S. Hoffman, and J. H. Priest, Synthesis and Properties of Vinyl Monomer/Enzyme Conjugates. Applied Biochemistry and Biotechnology, 1987. 15: p. 11-24). This acryloyl-modified protein was mixed with other acrylamide monomers (3:97) and DSCG (~8 wt %) in one-pot polymerization and cross-linked to produce protein-laden porous hydrogel. The preferred location of immobilized protein was confirmed by measuring confocal fluorescence of an immobilized fluorescent protein (FITC-tagged avidin) (Frey, M. D. and B. J. Radola, Rapid staining of proteins in ultrathin-layer isoelectric focusing in polyacrylamide gels. Electrophoresis, 1982. 3(1): p. 27-32): Fluorescent signal was observed only on the surface and the layer of the pores (FIG. 16). As a control, when the loading of the FITC-tagged avidin is increased from 7450 fold (from 200 nM to 1.49 mM), fluorescent signal are observed in the entire gel materials.

Studies were conducted of the enzymatic activities of 3 different enzymes (horseradish peroxidase, amylase, and aldolase) immobilized on polyacrylamide porous hydrogel prepared in the one-pot method (FIG. 9). Horseradish peroxidase (HRP) was used to catalyze a chemiluminescence reaction of luminol dissolved in solution, which generates a visible blue light (424 nm) (Cormier, M. J. and P. M. Prichard, An investigation of the mechanism of the luminescent peroxidation of luminol by stopped flow techniques. The Journal of Biological Chemistry, 1968. 243(18): p. 4706-14); amylase to catalyze the breakdown of polysaccharide (β-cyclodextrin) by hydrolyzing α-1,4-glycosidic linkages (Turner, P., A. Labes, O. H. Fridjonsson, G. O. Hreggvidson, P. Schoenheit, J. K. Kristjansson, O. Holst, and E. N. Karlsson, Two novel cyclodextrin-degrading enzymes isolated from thermophilic bacteria have similar domain structures but differ in oligomeric state and activity profile. J. Biosci. Bioeng., 2005. 100(4): p. 380-390; Yang, S.-J., H.-S. Lee, C.-S. Park, Y.-R. Kim, T.-W. Moon, and K.-H. Park, Enzymatic analysis of an amylolytic enzyme from the hyperthermophilic archaeon *Pyrococcus fuiriosus* reveals its novel catalytic properties as both an alpha-amylase and a cyclodextrin-hydrolyzing enzyme. Appl. Environ. Microbiol., 2004. 70(10): p. 5988-5995; Uitdehaag, J. C. M., L. Dijkhuizen, and B. W. Dijkstra, Cyclodextrin glycosyltransferase as a model enzyme to study the reaction mechanism of the alpha-amylase family. Spec. Publ.-R. Soc. Chem., 2002. 275(Carbohydrate Bioengineering): p. 82-86; Guzman-Maldonado, H. and O. Paredes-Lopez, Amylolytic enzymes and products derived from starch: a review. Crit. Rev. Food Sci. Nutr., 1995. 35(5): p. 373-403; Svensson, B., K. S. Bak-Jensen, H. Mori, J. Sauer, M. T. Jensen, B. Kramhoft, T. E. Gottschalk, T. Christensen, B. W. Sigurskjold, N. Aghajari, R. Haser, N. Payre, S. Cottaz, and H. Driguez, The engineering of specificity and stability in selected starch degrading enzymes. Spec. Publ.-R. Soc. Chem., 1999. 246(Recent Advances in Carbohydrate Bioengineering): p. 272-281), and aldolase (N-Acetylneuraminic acid aldolase, a type I aldolase from *E. coli*) to catalyze the ligation between monossacharides (mannose) and pyruvates to form sialic acids (Uchida, Y., Y. Tsukada, and T. Sugimori, Purification and properties of N-acetylneuraminate lyase from *Escherichia coli*. J Biochem, 1984. 96(2): p. 507-22; Takayama, S., G. J. McGarvey, and C.-H. Wong, Microbial aldolases and transketolases: new biocatalytic approaches to simple and complex sugars. Annu. Rev. Microbiol., 1997. 51: p. 285-310).

Figure 18:
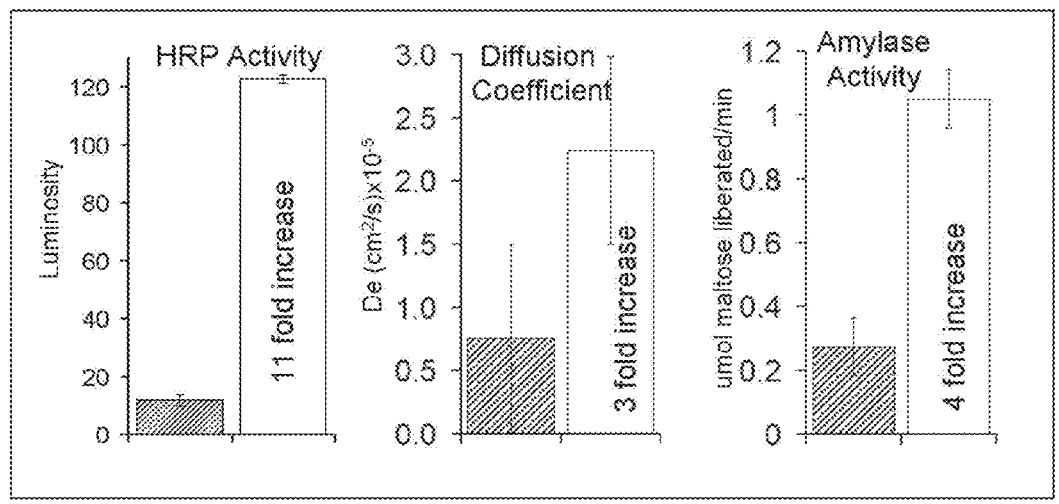
FIG. 18. are graphs showing protein activities and diffusion coefficient for non-porous (shaded bar) and porous (white bar) hydrogel.

Whereas porous HRP-laden hydrogel emits intense blue light (FIG. 17A), non-porous versions show essentially no light emission (FIG. 17B). Porous hydrogel soaked in a solution of free HRP followed by immersion in a luminol solution shows blue light emission in the whole solution (FIG. 17C) supporting that HRP is covalently immobilized on the hydrogel in the cases for FIG. 17A. The activity of amylase was characterized by a colorimetric assay that depends on the reduction of dinitrosalicylic acid by the anomeric group of enzymatic reaction product (degraded sugar fragments from β-cyclodextrin, result not included) (Miller, G. L., Dinitrosalicylic acid reagent for determination of reducing sugar. Anal. Chem., 1959. 31: p. 426-8). The diffusion of bovine serum albumin (BSA) from the hydrogels was characterized by first soaking the hydrogel in a BSA solution followed by immersion in fresh buffer. The diffusion of BSA from hydrogel into the fresh buffer over time is determined through Bradford assay, in which the concentration of BSA in the buffer is measured by the UV absorbance change resulting from the protein reacting with a Coomassie blue dye (Bradford, M. M., A rapid and sensitive method for the quantitation of microgram quantities of protein utilizing the principle of protein-dye binding. Analytical Biochemistry, 1976. 72(1-2):

p. 248-54). FIG. 18 summarizes the quantified enzymatic activities of HRP and amylase, as well as the diffusion coefficient of BSA from porous and non-porous hydrogel. For both HRP and amylase, the enzymatic activities are higher on porous hydrogel than non-porous hydrogel. Interestingly, for HRP, the increase in enzymatic activities in porous over non-porous hydrogel is significantly higher than that of the magnitude in the increase of diffusion coefficient; whereas for amylase, the magnitude in the increase of enzymatic activity is similar to that in diffusion coefficient. This result suggests that diffusion due to porosity alone does not sufficiently account for the increase in enzyme activity on hydrogel. Together, it is believed that the enzyme activity is highly retained, and potentially enhanced, on non-porous hydrogel.

Example 7

Synthesis of Sialic Acid Using Porous Hydrogel

Figure 19:
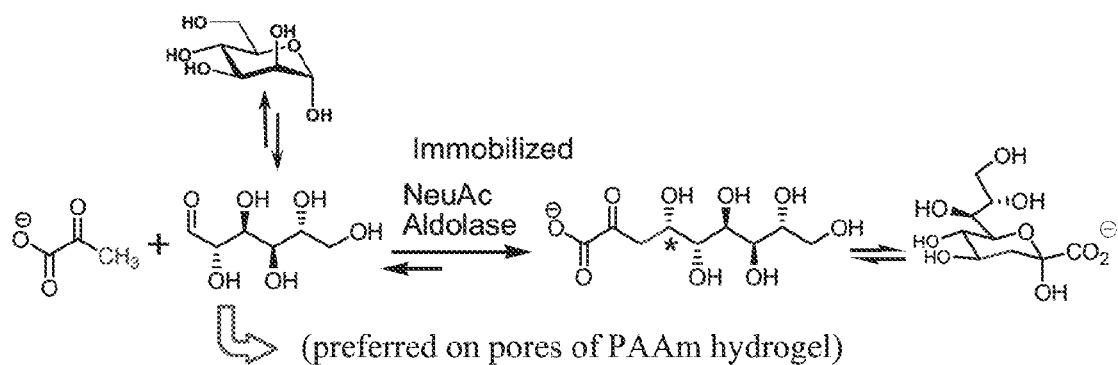
FIG. 19 depicts a reaction scheme showing cyclic and linear forms of mannose substrate in relation to the hydrogel of the present invention.
Figure 20:
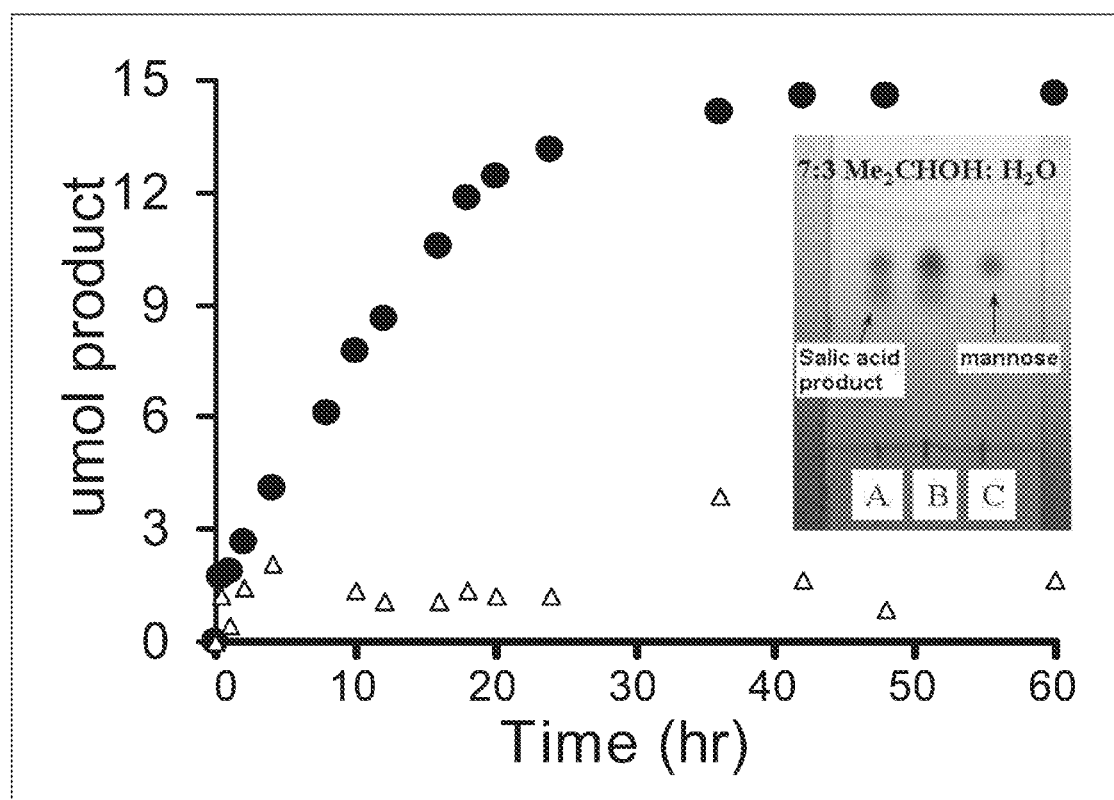
FIG. 20 is a graph showing the amount of sialic acid produced by porous hydrogel with (filled circle) and without (unfilled triangle) immobilized aldolase over time. The solution constains 293 mM of mannose and 10 mM of pyruvate in a pH 7.5 PBS buffer. The hydrogel is swelled with pyruvate solution; volume of solution absorbed by the gel is obtained by the different mass between wet and dry weights of the hydrogels. The inset shows TLC of the sialic acid product.

Sialic acids are compounds that are of therapeutic interest (Kim, M. J., W. J. Hennen, H. M. Sweers, and C. H. Wong, Enzymes in carbohydrate synthesis: N-acetylneuraminic acid aldolase catalyzed reactions and preparation of N-acetyl-2-deoxy-D-neuraminic acid derivatives. J. Am. Chem. Soc., 1988. 110(19): p. 6481-6; Lin, C. H., T. Sugai, R. L. Halcomb, Y. Ichikawa, and C. H. Wong, Unusual stereoselectivity in sialic acid aldolase-catalyzed aldol condensations: synthesis of both enantiomers of high-carbon monosaccharides. J. Am. Chem. Soc., 1992. 114(26): p. 10138-45). The activity of aldolase for synthesizing sialic acids has been quantified. This enzymatic reaction makes a carbon-carbon bond instead of breaking one. It was hypothesized that the pore surfaces of the hydrogel of the present invention can change the equilibrium between the cyclic and linear form of the mannose substrate (FIG. 19). FIG. 20 shows the amount of sialic acid generated by porous hydrogel laden with aldolase over time by measuring the depletion of one of the substrates, pyruvate (Kim, M. J., W. J. Hennen, H. M. Sweers, and C. H. Wong, Enzymes in carbohydrate synthesis: N-acetylneuraminic acid aldolase catalyzed reactions and preparation of N-acetyl-2-deoxy-D-neuraminic acid derivatives. J. Am. Chem. Soc., 1988. 110(19): p. 6481-6; Lin, C. H., T. Sugai, R. L. Halcomb, Y. Ichikawa, and C. H. Wong, Unusual stereoselectivity in sialic acid aldolase-catalyzed aldol condensations: synthesis of both enantiomers of high-carbon monosaccharides. J. Am. Chem. Soc., 1992. 114(26): p. 10138-45). The product, sialic acid, is confirmed by mass spectroscopy and thin layer chromatography. The enzyme kinetic shows the same product equilibrium as that catalyzed by free enzyme. It is noted that the enzyme-laden porous hydrogels of the present invention can be dried by speed vacuum (but not lyphilization) and rehydrated without loss of activity, and the hydrated hydrogel can be reused for at least 3 times without noticeable decrease in activity.

Example 8

Figure 21:
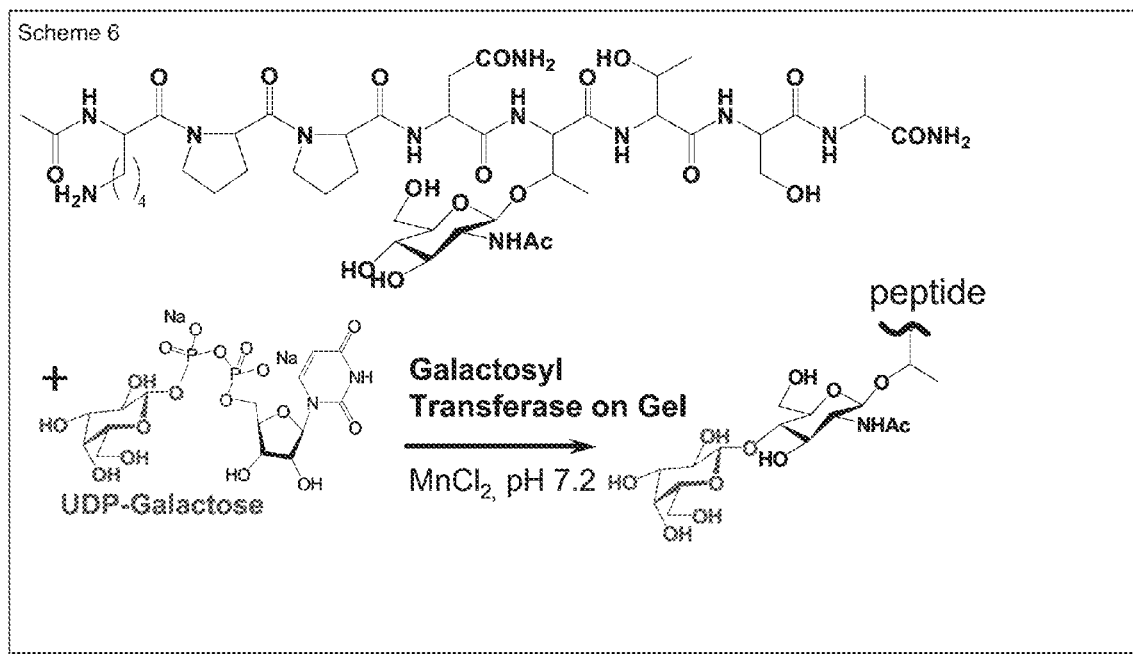
FIG. 21 depicts a reaction scheme related to glycosylation of peptides and proteins with sugar molecules by β-1,4-galactosyltransferase.

Modification of Protein Drug by Immobilized Trans-Golgi Glycosyltransferase on Hydrogel To confirm the general capability of porous hydrogel made by water-in-water emulsion for supporting and enhancing immobilized enzymatic activities, studies will be conducted of a particularly challenging enzymatic reaction that will require more stringent in vivo-like conditions: glycosylation of peptides and proteins (rather than small molecule substrates) with sugar molecules by β-1,4-galactosyltransferase (FIG. 21).

β-1,4-galactosyltransferase (β4Gal-T1) is a functionally versatile membrane protein bound in the lipid bilayer of Golgi apparatus in mammalian cells (Qasba, P. K., B. Ramakrishnan, and E. Boeggeman, Structure and function of beta-1,4-galactosyltransferase. Curr. Drug Targets 2008. 9(4): p. 292-309; Schachter, H., I. Jabbal, R. L. Hudgin, L. Pinteric, E. J. McGuire, and S. Roseman, Intracellular localization of liver sugar nucleotide glycoprotein glycosyltransferases in a Golgi-rich fraction. J Biol Chem FIELD Full Journal Title: The Journal of biological chemistry, 1970. 245(5): p. 1090-100; Fraser, I. H. and S. Mookerjea, Studies on the purification and properties of UDP-galactose-glycoprotein galactosyltransferase from rat liver and serum. Biochem. J., 1976. 156(2): p. 347-55). Its functions involve glycosylation of targeted peptide and protein substrates (Qasba, P. K., B. Ramakrishnan, and E. Boeggeman, Structure and function of beta-1,4-galactosyltransferase. Curr. Drug Targets 2008. 9(4): p. 292-309; Granovsky, M., T. Bielfeldt, S. Peters, H. Paulsen, M. Meldal, J. Brockhausen, and I. Brockhausen, UDPgalactose:glycoprotein-N-acetyl-D-galactosamine 3-beta-D-galactosyltransferase activity synthesizing O-glycan core 1 is controlled by the amino acid sequence and glycosylation of glycopeptide substrates. Eur. J. Biochem., 1994 221(3): p. 1039-46), it also catalyze synthesis of dissacharides. Interestingly, this protein is also found on cell membrane and is believed to function as a cell adhesion molecule (Evans, S. C., L. C. Lopez, and B. D. Shur, Dominant negative mutation in cell surface beta 1,4-galactosyltransferase inhibits cell-cell and cell-matrix interactions. J. Cell Biol., 1993. 120(4): p. 1045-57; Lopez, L. C., A. Youakim, S. C. Evans, and B. D. Shur, Evidence for a molecular distinction between Golgi and cell surface forms of beta 1-4-galactosyltransferase. J. Biol. Chem., 1991. 266(24): p. 15984-91). It is believed that although β4Gal-T1 is a membrane protein, which is often more delicate and less stable than a globular protein, retaining or enhancing the activity of this protein immobilized on porous hydrogel is feasible because the transmembrane domain of β4Gal-T1 only comprises a small portion of the protein (Qasba, P. K., B. Ramakrishnan, and E. Boeggeman, Structure and function of beta-1,4-galactosyltransferase. Curr. Drug Targets 2008. 9(4): p. 292-309). The challenge and the significance is that the catalytic domain is unusually large, consisting of about 270 amino acid residues (Shaper, N. L., G. F. Hollis, J. G. Douglas, I. R. Kirsch, and J. H. Shaper, Characterization of the full length cDNA for murine beta-1,4-galactosyltransferase. Novel features at the 5'-end predict two translational start sites at two in-frame AUGs. J. Biol. Chem. FIELD Full Journal Title: Journal of Biological Chemistry, 1988. 263(21): p. 10420-8; Malissard, M. and E. G. Berger, Improving the solubility of the catalytic domain of human beta-1,4-galactosyltransferase 1 through rationally designed amino-acid replacements. Eur. J. Biochem., 2001. 268(15): p. 4352-4358; Malissard, M., L. Borsig, S. Di Marco, M. G. Gruetter, U. Kragl, C. Wandrey, and E. G. Berger, Recombinant soluble beta-1,4-galactosyltransferases expressed in *Saccharomyces cerevisiae*. Purification, characterization and comparison with human enzyme. Eur. J. Biochem., 1996. 239(2): p. 340-348), and thus provides a stringent case for evaluating the general biocompatibility and capability of porous hydrogel to support enzymatic activities. As an advantage for immobilization, among the ten existing lysine residues in β4Gal-T1, which can be modified with acrylic moiety for immobilization, none of them are conserved among this class of enzymes from different animal sources, and thus are unlikely to be critical for maintaining enzymatic activity of the enzyme (Qasba, P. K., B. Ramakrishnan, and E. Boeggeman, Structure and function of beta-1,4-galactosyltransferase. Curr. Drug Targets 2008. 9(4): p. 292-309); Malissard, M. and E. G. Berger, Improving the solubility of the catalytic domain of human beta-1,4-galactosyltransferase 1 through rationally designed amino-acid replacements. Eur. J. Biochem., 2001. 268(15): p. 4352-4358; Malissard, M., L. Borsig, S. Di Marco, M. G. Gruetter, U. Kragl, C. Wandrey, and E. G. Berger, Recombinant soluble beta-1,4-galactosyltransferases expressed in *Saccharomyces cerevisiae*. Purification, characterization and comparison with human enzyme. Eur. J. Biochem., 1996. 239(2): p. 340-348).

It is proposed that the enzymatic activity will be measured of immobilized β4Gal-T1 on glycosylation of peptides (FIG. 21) (Granovsky, M., T. Bielfeldt, S. Peters, H. Paulsen, M. Meldal, J. Brockhausen, and I. Brockhausen, UDPgalactose:glycoprotein-N-acetyl-D-galactosamine 3-beta-D-galactosyltransferase activity synthesizing O-glycan core 1 is controlled by the amino acid sequence and glycosylation of glycopeptide substrates. Eur. J. Biochem., 1994. 221(3): p. 1039-46; Seitz, O. and C.-H. Wong, Chemoenzymic solution- and solid-phase synthesis of O-glycopeptides of the Mucin domain of MAdCAM-1. A general route to O-LacNAc, O-Sialyl-LacNAc, and O—Sialyl-Lewis-X peptides. J. Am. Chem. Soc., 1997. 119(38): p. 8766-8776), and protein Ovalbumin (Prieels, J. P., M. Dolmans, M. Schindler, and N. Sharon, The binding of glycoconjugates to human-milk D-galactosyltransferase. Eur. J. Biochem., 1976. 66(3): p. 579-82; Sheares, B. T. and P. W. Robbins, Glycosylation of ovalbumin in a heterologous cell: analysis of oligosaccharide chains of the cloned glycoprotein in mouse L cells. Proc. Natl. Acad. Sci. U.S.A. FIELD Full Journal Title: Proceedings of the National Academy of Sciences of the United States of America, 1986. 83(7): p. 1993-7). Ovalbumin has two potential glycosylation sites for β4Gal-T1 (Sheares, B. T. and P. W. Robbins, Glycosylation of ovalbumin in a heterologous cell: analysis of oligosaccharide chains of the cloned glycoprotein in mouse L cells. Proc. Natl. Acad. Sci. U.S.A. FIELD Full Journal Title: Proceedings of the National Academy of Sciences of the United States of America, 1986. 83(7): p. 1993-7). The kinetic data ($K_m$ and $V_{max}$) for β4Gal-T1 on both of the two substrates are known (Granovsky, M., T. Bielfeldt, S. Peters, H. Paulsen, M. Meldal, J. Brockhausen, and I. Brockhausen, UDPgalactose:glycoprotein-N-acetyl-D-galactosamine 3-beta-D-galactosyltransferase activity synthesizing O-glycan core 1 is controlled by the amino acid sequence and glycosylation of glycopeptide substrates. Eur. J. Biochem., 1994. 221(3): p. 1039-46; Seitz, O. and C.-H. Wong, Chemoenzymic solution- and solid-phase synthesis of O-glycopeptides of the Mucin domain of MAdCAM-1. A general route to O-LacNAc, O—Sialyl-LacNAc, and O—Sialyl-Lewis-X peptides. J. Am. Chem. Soc., 1997. 119(38): p. 8766-8776; Sheares, B. T. and P. W. Robbins, Glycosylation of ovalbumin in a heterologous cell: analysis of oligosaccharide chains of the cloned glycoprotein in mouse L cells. Proc. Natl. Acad. Sci. U.S.A. FIELD Full Journal Title: Proceedings of the National Academy of Sciences of the United States of America, 1986. 83(7): p. 1993-7). To be precisely quantitative, measurements will first be made of the amount of enzyme actually immobilized on the hydrogel by using a "Bradford" assay that will measure the amount of protein that are not immobilized on the hydrogel due to incomplete reaction during the one pot hydrogel fabrication. The amount of immobilized protein will be obtained by subtracting the diffused enzyme from the total enzyme used in the reaction. The product and the enzyme kinetics of glycosylation of the peptide will be measured by liquid chromatography mass spectroscopy. The product of the glycosylation of Ovalbumin will be purified by HPLC and characterized by MALDI, and the enzyme kinetics will be assayed by using radiolabelled UDP-galactose.

Example 9

New Brominated Furanones

Biofilm inhibitors with controlled regiochemistry. Previously, a class of biofilm inhibitor was discovered from the extracts of marine macro-alga (seaweed) *Delisea pulchra*, which exhibits remarkable anti-fouling features (de Nys R., A. D. Wright, G. M. Konig, and O, Sticher, New Halogenated Furanone from the Marine Alga *Delisea pulchra* (cf. fimbriata). Tetrahedron, 1993. 49(48): p. 11213-11220). These inhibitors consist of about 30 different brominated furanones (small molecules with 5-member rings substituted with bromides) (de Nys, R., A. D. Wright, G. M. Konig, and O. Sticher, New Halogenated Furanone from the Marine Alga *Delisea pulchra* (cf. fimbriata). Tetrahedron, 1993. 49(48): p. 11213-11220; Kazlauskas, R., P. T. Murphy, R. J. Quinn, and R. J. Wells, A new class of halogenated lactones from the red alga *Delisea fimbriata* (bonnemaisoniaceae) Tetrahedron Letters, 1977. 1(18): p. 37-40). These molecules have been shown to control a wide spectrum of multicellular behaviors of bacteria, including biofilm formation, at concentrations non-toxic to mammalian cells (Baveja, J. K., M. D. P. Willcox, E. B. H. Hume, N. Kumar, R. Odell, and L. A. Poole-Warren, Furanones as Potential Anti-Bacterial Coating on Biomaterials. Biomaterials, 2004. 25: p. 5003-5012; Hentzer, M., H. Wu, J. B. Andersen, K. Riedel, T. B. Rasmussen, N. Bagge, N. Kumar, M. A. Schembri, Z. Song, P. Kristoffersen, M. Manefield, J. W. Costerton, S. Molin, L. Eberl, P. Steinberg, S. Kjelleberg, N. Høiby, and M. Givskov, Attenuation of *Pseudomonas aeruginosa* Virulence by Quorum Sensing Inhibitors. The European Molecular Biology Organization Journal, 2003. 22: p. 3803-3815; Cava, R. J., F. J. DiSalvo, L. E. Brus, K. R. Dunbar, C. B. Gorman, S. M. Haile, L. V. Interrante, J. L. Musfeldt, A. Navrotsky, R. G. Nuzzo, W. E. Pickett, A. P. Wilkinson, C. Ahn, J. W. Allen, P. C. Burns, G. Ceder, C. E. D. Chidsey, W. Clegg, E. Coronado, H. Dai, M. W. Deem, B. S. Dunn, G. Galli, A. J. Jacobson, M. Kanatzidis, W. Lin, A. Manthiram, M. Mrksich, D. Norris, A. J. Nozik, X. Peng, C. Rawn, D. Rolison, D. J. Singh, B. H. Toby, S. Tolbert, U. B. Wiesner, P. M. Woodward, and P. Yang, Future directions in solid state chemistry: report of the NSF-sponsored workshop. Progress in Solid State Chemistry, 2002. 30(1-2): p. 1-101; Chapman, R. G., E. Ostuni, M. N. Liang, G. Meluleni, E. Kim, L. Yan, G. Pier, H. S. Warren, and G. M. Whitesides, Polymeric Thin Films That Resist the Adsorption of Proteins and the Adhesion of Bacteria. Langmuir, 2001. 17(4): p. 1225-1233; Ren, D., L. A. Bedzyk, S. M. Thomas, R. W. Ye, and T. K. Wood, Differential Gene Expression Shows Natural Brominated Furanones Interfere with the Autoinducer-2 Bacterial Signaling System of *Escherichia coli*. Biotechnology and Bioengineering, 2004. 88: p. 630-642). Many of the past studies on the biological activities of this class of molecules are conducted with a mixture of molecules or with undefined regiochemistry. A systematic study of the effect of structural variation of furanones on the biofilm formation is still lacking.

Figure 22:
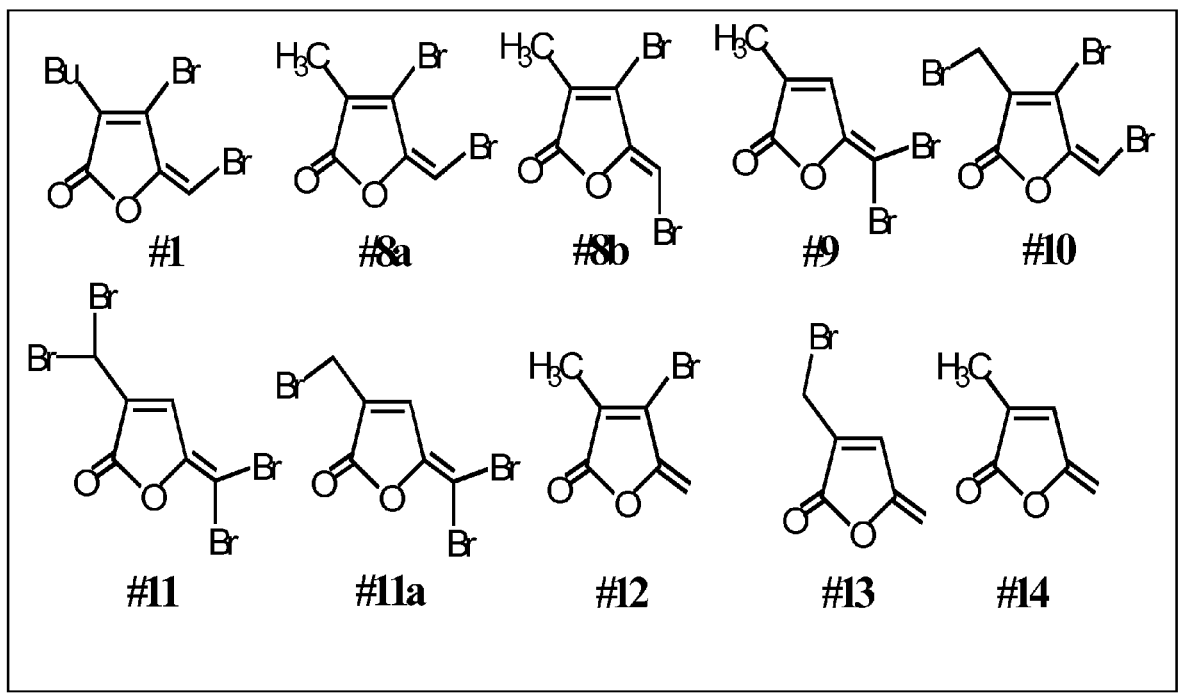
FIG. 22 illustrates the structures of new brominated furanones with controlled regiochemistry. Structure #1 represents natural furanone.

In one aspect of the present invention, a class of brominated furanones was recently synthesized with control in both the degree of bromination and the regiochemistry (FIG. 22). The control of molecular structure will greatly assist to help address the open questions mentioned above. For instance, furanone #13 only supports $S_N2$ nucleophilic substitution, and not Michael addition-elimination, whereas furanone #12 can only proceed by Michael addition-elimination and not $S_N2$ reaction. The study of inhibitory activity and toxicity of these molecules will thus shed light on the mechanism of the small molecule inhibition, and help the design of new drugs.

For mechanistic study, the protein TraR from *Agrobacterium tumefaciens* will be a point of focus. This protein has been shown to specifically bind to a variety of acyl-homoserine lactones (AHL) (Zhu, J. and S. C. Winans, The quorum-sensing transcriptional regulator TraR requires its cognate signaling ligand for protein folding, protease resistance, and dimerization. Proceedings of the National Academy of Sciences of the United States of America, 2001. 98(4): p. 1507-1512; Zhu, J. and S. C. Winans, Autoinducer binding by the quorum-sensing regulator TraR increases affinity for target promoters in vitro and decreases TraR turnover rates in whole cells. Proceedings of the National Academy of Sciences of the United States of America, 1999. 96(9): p. 4832-4837). As brominated furanones are known to compete with AHL, the TraR is an ideal model protein for mechanistic study of the quorum sensing inhibition by brominated furanones.

Preliminary Inhibition Results.

Interestingly, the new furanones of the present invention, as compared with natural ones, inhibit the biofilm formation by a wide variety of micro-organisms and the growth of pathogenic fungus, *Candida albicans*, extending the activity to the eukaryotic kingdom. At non-toxic concentration (cell growth not affected), furanone #8, 9, and 10 (60 µg/mL) repressed *E. coli* biofilm formation on stainless steel surface by 75, 86, and 91% of the surface coverage, respectively.

Figure 23:
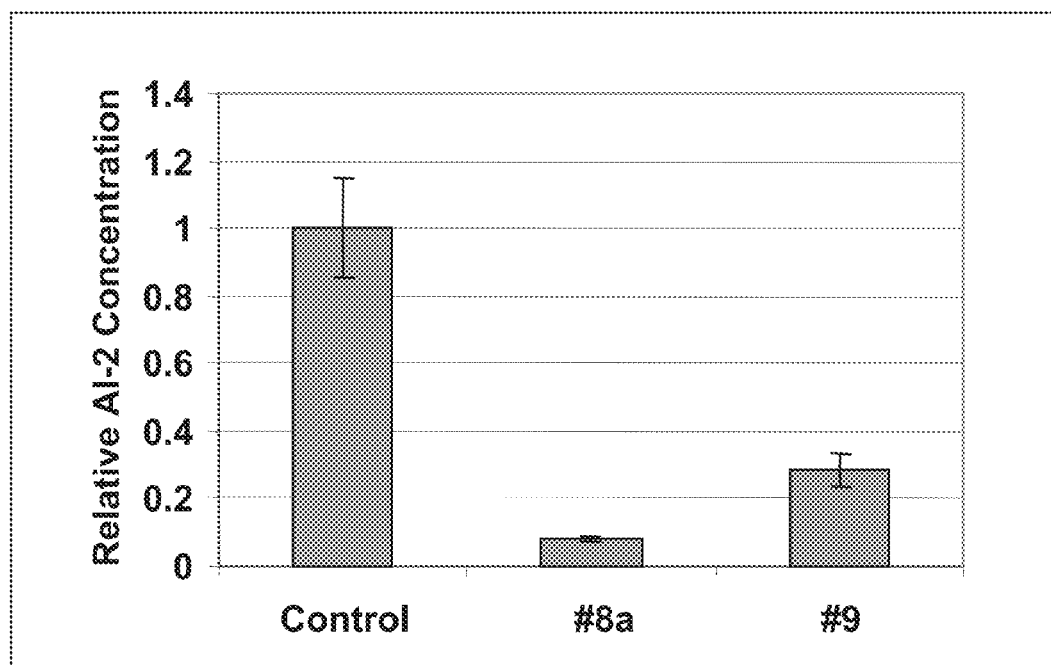
FIG. 23 is a graph showing inhibition of AI-2 synthesis by new brominated furanones.

Biofilm formation relies on bacteria's secretion and sensing (quorum sensing) of signal molecules (called auto-inducer). Whereas previous results show inhibition of biofilm formation based on auto-inducer 1 (AI-1, acetylated homoserine lactone), the class of furanones of the present invention also inhibits biofilm formation based on the quorum sensing of antoinducer-2 (AI-2, borate complexed with 4,5-Dihydroxy-2,3-pentanedione). Furanone #8 and 9 (60 µg/mL) inhibited AI-2 synthesis in *E. coli* 12.5- and 3.5-fold. In contrast, 100 µg/mL of natural furanone #1 inhibited AI-2 synthesis by only 2-fold (FIG. 23) (Ren, D., L. A. Bedzyk, S. M. Thomas, R. W. Ye, and T. K. Wood, Differential Gene Expression Shows Natural Brominated Furanones Interfere with the Autoinducer-2 Bacterial Signaling System of *Escherichia coli*. Biotechnology and Bioengineering, 2004. 88: p. 630-642). The relative concentration of AI-2 was measured by a bioluminescence assay by using the reporter strain *Vibrio harveyi* BB 170 (Ren, D., L. A. Bedzyk, S. M. Thomas, R. W. Ye, and T. K. Wood, Differential Gene Expression Shows Natural Brominated Furanones Interfere with the Autoinducer-2 Bacterial Signaling System of *Escherichia coli*. Biotechnology and Bioengineering, 2004. 88: p. 630-642; Surette, M. G., M. B. Miller, and B. L. Bassler, Quorum Sensing in *Escherichia coli, Salmonella typhimurium*, and *Vibrio harveyi*: A New Family of Genes Responsible for Autoinducer Production. Proceedings of the National Academy of Sciences, 1999. 96: p. 1639-1644).

Figure 24:
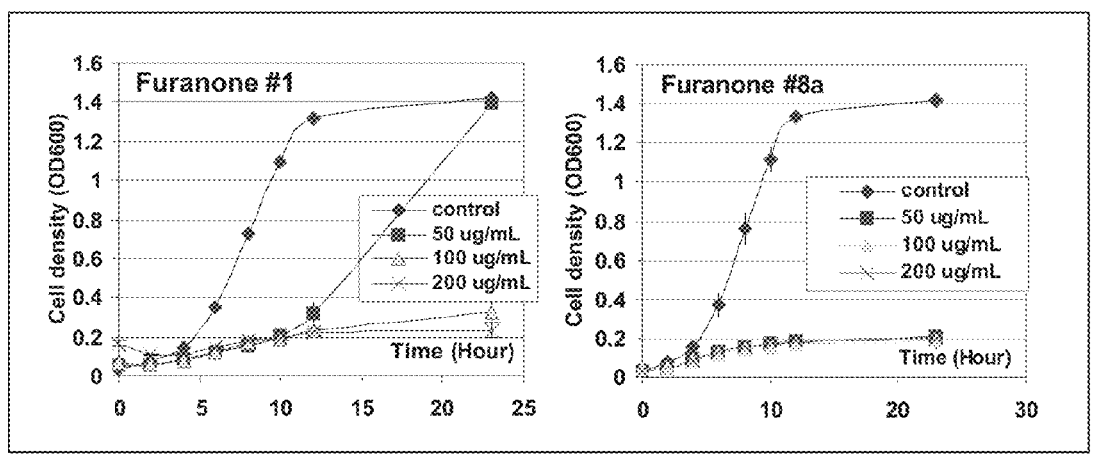
FIG. 24 depicts graphs showing inhibition of pathogenic fungus *Candida albicans* is stronger by new furanone #8a than natural furanone #1.

Interestingly, new furanone #8 of the present invention is more potent than the natural furanone #1 at inhibiting the growth of pathogenic fungus *Candida albicans* at the concentrations that are not toxic to *E. coli* (FIG. 24). These discoveries suggest that new furanones are promising for controlling fungal biofilms and related problems (e.g., wood decay and infections due to the airborne fungal spores). Having higher activities than the natural furanones, this class of brominated furanones is resourceful for targeting many other harmful microbial phenotypes. This new series of brominated furanones will be encapsulated into a porous hydrogel of the present invention to explore a controlled drug release mechanism for controlling the formation of biofilms.

In one particular embodiment, the new brominated furanones of the present invention can be synthesized as follows:

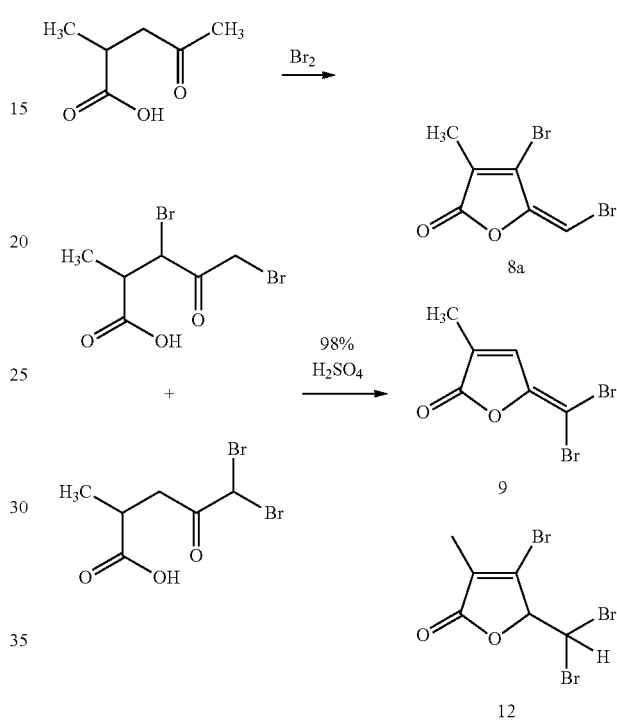

In another particular embodiment, the new brominated furanones of the present invention can linked to adamantane. One synthetic pathway for doing so is as follows:

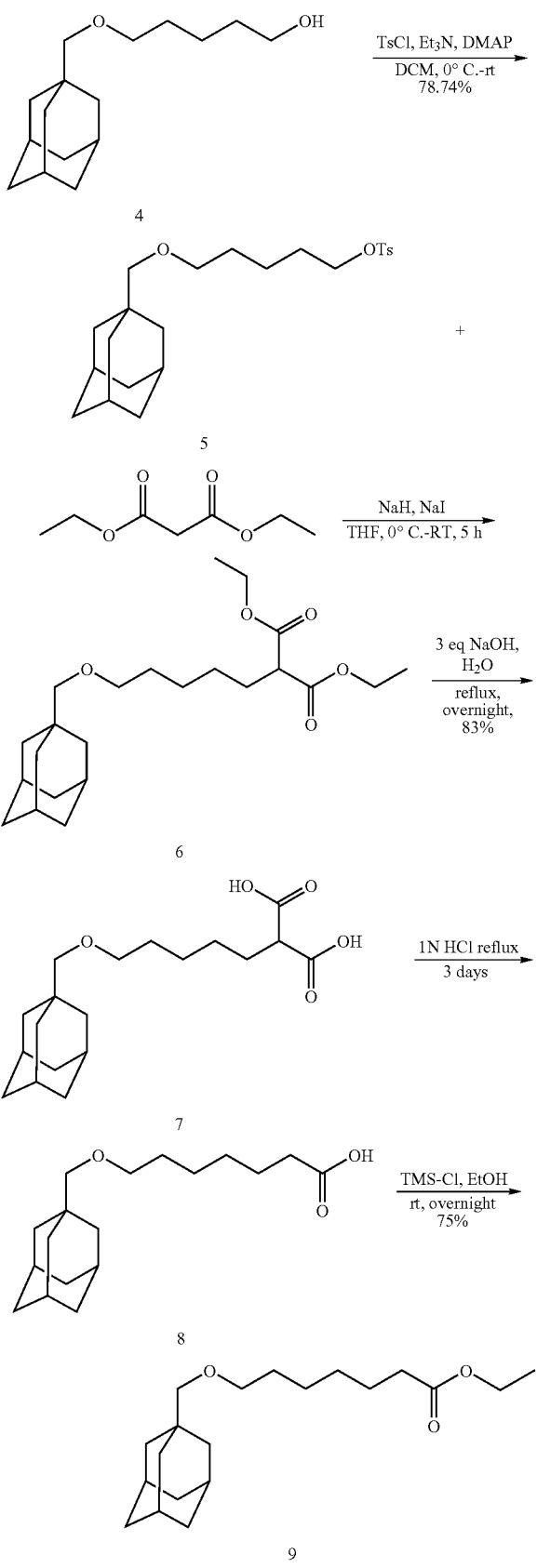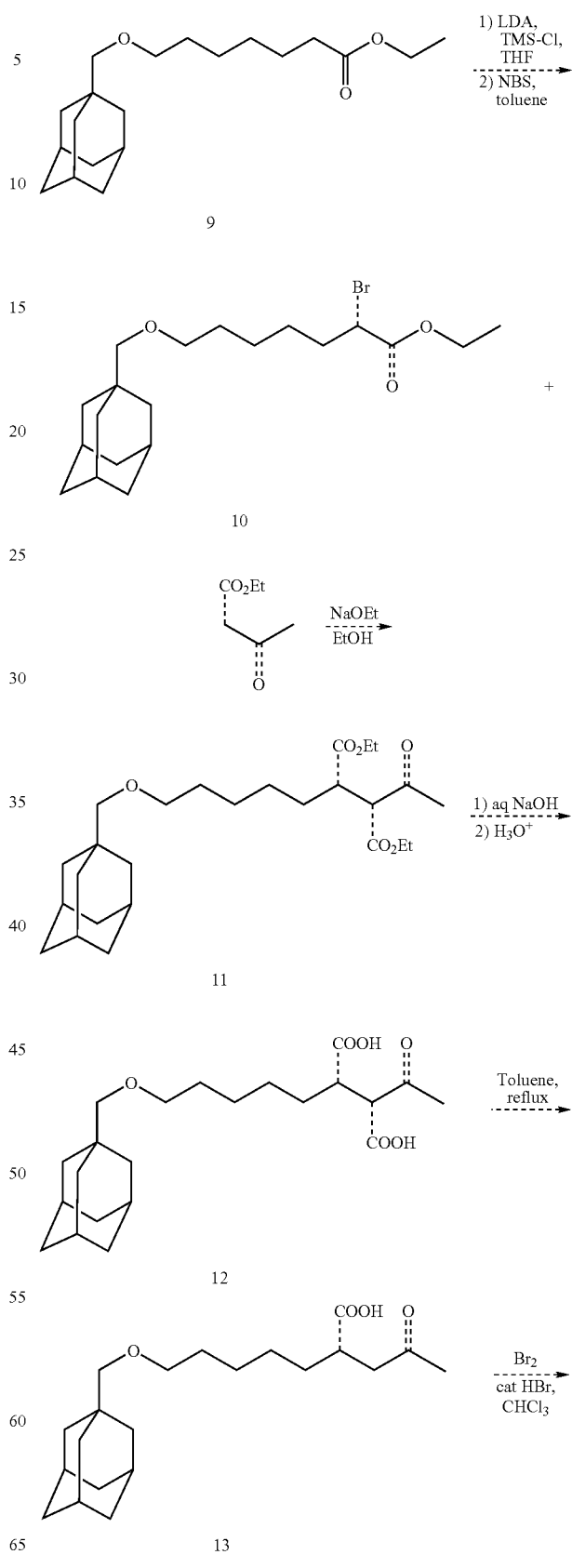

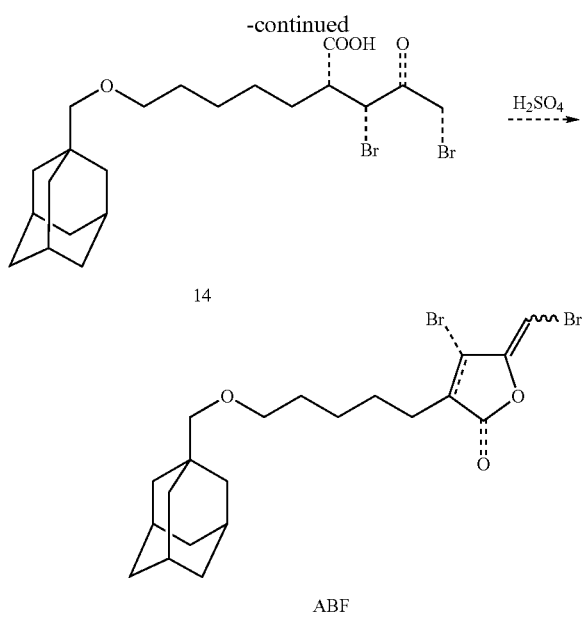

ABF

Example 10

Using Enzyme-Immobilized Hydrogels to Catalyze the Degradation of Biofilms

Incorporating Enzymes in the Materials to Degrade the Polysaccharides of the Biofilm.

Enabled by the feasibility of the new fabrication methods, multiple enzymes will be incorporated into the porous hydrogel for degrading many types of chemical bonds of polysaccharide secreted by the bacteria in the biofilm. While using enzymes to degrade polysaccharides is a well-established science and mature application in industry (Shainoff, J. R., Zonal immobilization of proteins. Biochemical and Biophysical Research Communications, 1980. 95(2): p. 690-5), there are only a very few attempts at using enzyme to degrade the polysaccharide matrix for biofilm (Ong, E., J. M. Greenwood, N. R. Gilkes, D. G. Kilbum, R. C. Miller, Jr., and R. A. J. Warren, The cellulose-binding domains of cellulases: tools for biotechnology. Trends Biotechnol., 1989. 7(9): p. 239-43; Miyata, T., N. Asami, and T. Uragami, A reversibly antigen-responsive hydrogel. Nature (London), 1999. 399(6738): p. 766-769). Furthermore, there is a lack of engineering to modify both the interior and the surfaces of a material with active proteins.

Fabrication of the Porous Hydrogel Loaded with Enzyme.

Figure 10:
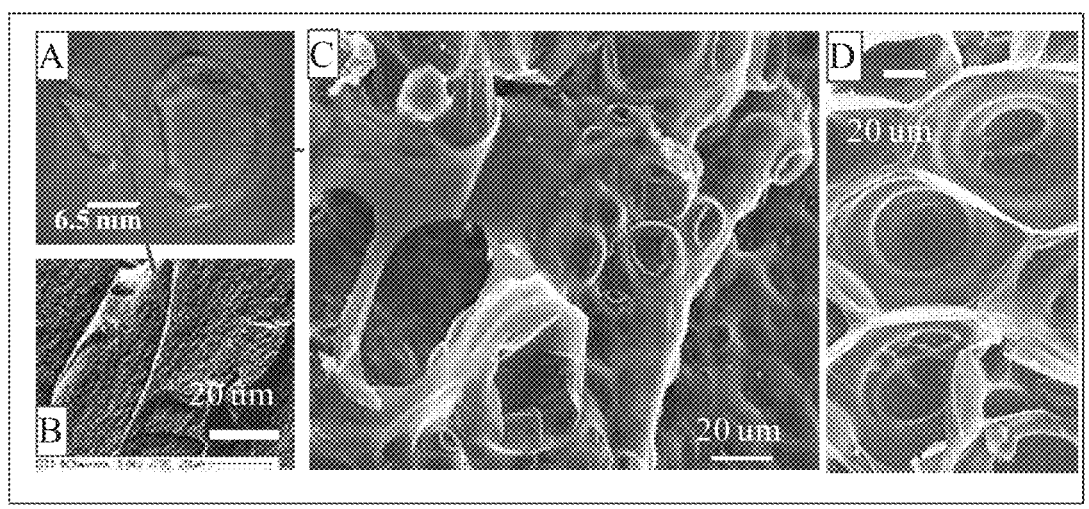
FIGS. 10A-10D are micrographs depicting the following: (A) Swelling of porous and non-porous polyacrylamide (PAAm) hydrogels prepared with and without the presence of DSCG. SEM images of PAAm hydrogel prepared with 12 wt % AAm, 1 wt % BIS, 0.4 wt % APS, 0.2 wt % TEMED, (B) without 5'DSCG or (C) with 8 wt % 5'DSCG, and (D) with 8 wt % 5'DSCG and 2 wt % binaphthyl salt.
Figure 11:
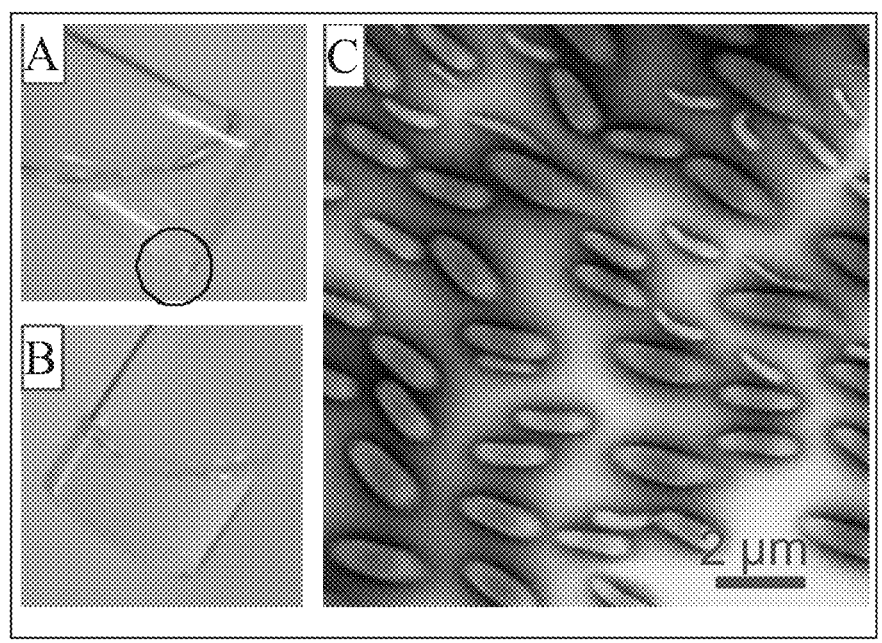
FIGS. 11A-11C are illustrations of isolated hydroshells based on w/w emulsions: (A) partially dissolved hydroshell solution (prepared from 8 wt % DSCG, 6 wt % AAm, 0.02 wt % BIS, 0.36 wt % APS, 0.18% TEMED) in excess water. (B) Shaking of (A) affords homogeneous solution. (C) TEM images of isolated hydroshells.
Figure 17:
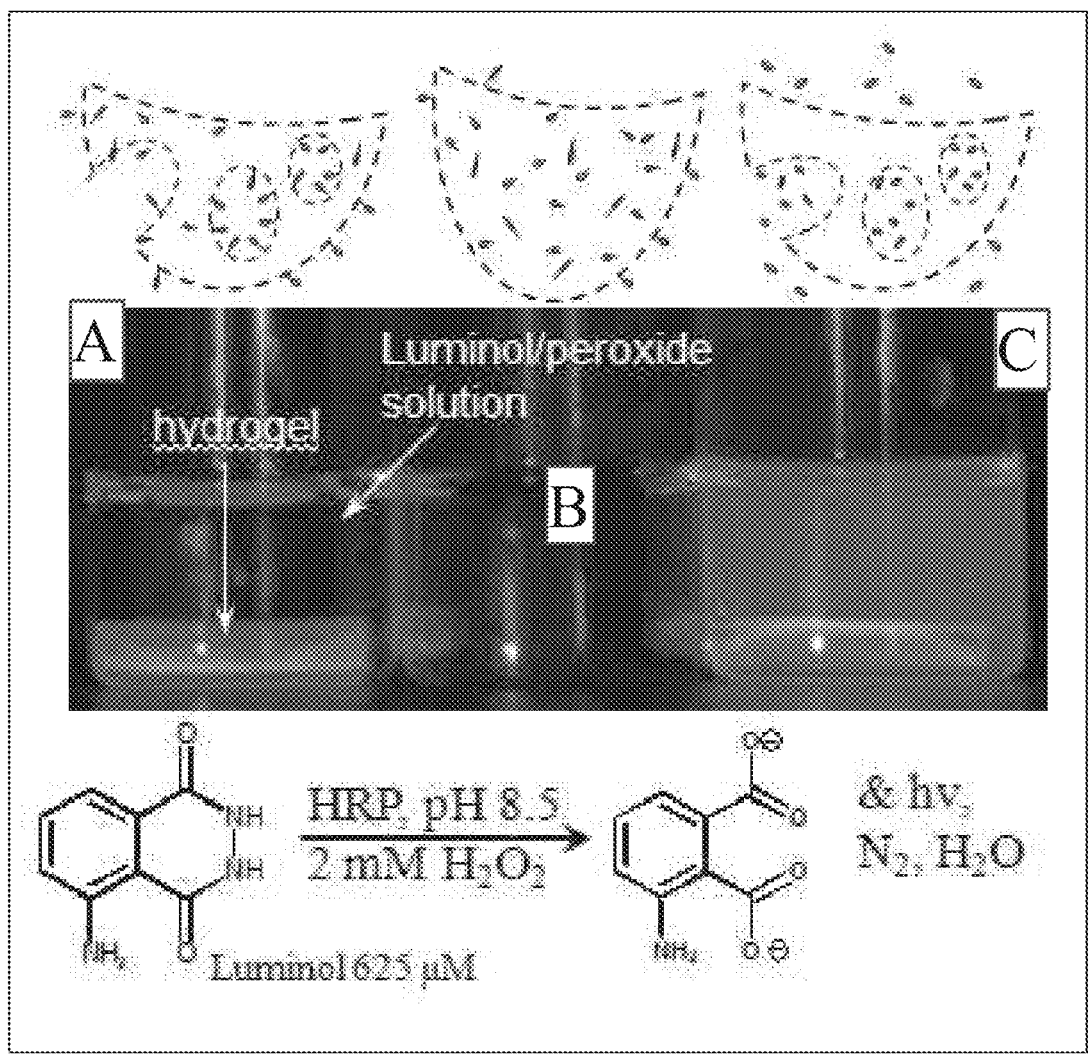
FIGS. 17A-17C depict biocatalysis of luminol reaction by HRP covalently immobilized on porous polyacrylic amide hydrogel (A), non-porous hydrogel (B), and by HRP non-covalently absorbed in a porous hydrogel (C). Schematic representations of hydrogels are shown above each figure.

Here, the porosity in the enzyme-linked hydrogel is created by taking advantage of the formation of water-in-water emulsion, and the subsequent removal of the DSCG molecule through diffusion (FIGS. 10, 16, and 17). The fabrication consists of three steps (Lin, V. S. Y., K. Motesharei, K.-P. S. Dancil, M. J. Sailor, and M. R. Ghadiri, A porous silicon-based optical interferometric biosensor. Science (Washington, D.C.), 1997. 278(5339): p. 840-843; Blanco, R. M. and J. M. Guisan, Protecting effect of competitive inhibitors during very intense insolubilized enzyme-activated support multipoint attachments: trypsin (amine)-agarose (aldehyde) system. Enzyme and Microbial Technology, 1988. 10(4): p. 227-32).

First, the enzymes will be modified with polymerizable units (—NH(CO)CH═CH2) via the coupling between the primary amine groups (from lysine groups on the protein) and N-succinimidylacrylate (NSA) units. Second, the monomers—enzyme-linked acrylic amide (~1-5%) and acrylic amide or polyol units (~95-99%)—will be mixed with DSCG molecules, and the porous hydrogel will be afforded by the usual radical polymerization. In one mixture, the polymer and the DSCG will phase separate to form water-in-water emulsion consisting of droplets of DSCG molecules coated with the cross-linked polymers. These two chemical processes proceed in situ in one flask. Third, the hydrogel will be subsequently immersed in pure water repeatedly to remove the DSCG molecules through diffusion, affording a highly porous hydrogel tethered with enzymes. It is important to note that this fabrication is enabled by the previous finding that DSCG liquid crystal phase does not disrupt antibody-antigen bindings (Ljungquist, C., B. Jansson, T. Moks, and M. Uhlen, Thiol-directed immobilization of recombinant IgG-binding receptors. Eur. J. Biochem. FIELD Full Journal Title: European Journal of Biochemistry, 1989. 186(3): p. 557-61; Picart, C. and D. E. Discher, Materials science: Embedded shells decalcified. Nature (London, U. K.), 2007. 448(7156): p. 879-880), which is essential as the antibodies and antigens will be in contact with DSCG liquid crystal phase (droplets) during the cross-linking of the hydrogels.

While previous work by others has established that proteins tethered using this chemistry in hydrogel are active for reversible antigen-antibody binding (Lin, V. S. Y., K. Motesharei, K.-P. S. Dancil, M. J. Sailor, and M. R. Ghadiri, A porous silicon-based optical interferometric biosensor. Science (Washington, D.C.), 1997. 278(5339): p. 840-843; Blanco, R. M. and J. M. Guisan, Protecting effect of competitive inhibitors during very intense insolubilized enzyme-activated support multipoint attachments: trypsin (amine)-agarose (aldehyde) system. Enzyme and Microbial Technology, 1988. 10(4): p. 227-32), the focus here we will be on using the tethered enzymes to catalyze the degradation of the polysaccharide matrix secreted by the bacteria—a process necessary for the formation of biofilm. The polysaccharide matrix of biofilm is composed of a wide range of different homo- and heteropolysaccharides, including dextrans, cellulose, amylopectin, glycogen, alginate, levans and polymannans (Ong, E., J. M. Greenwood, N. R. Gilkes, D. G. Kilburn, R. C. Miller, Jr., and R. A. J. Warren, The cellulose-binding domains of cellulases: tools for biotechnology. Trends Biotechnol., 1989. 7(9): p. 239-43). This wide range of polysaccharide structures invites the use of commercially available enzymes. Here, individual enzymes will be tethered into the porous hydrogel for degrading specific type of polysaccharide, as well as a mixture of different polysaccharide lyases. The individual enzymes include dextranase, cellulose, and amylase, as well as trypsin and Subtilisin A (enzymes with broad specificity to break down proteins). A large mixture of enzymes without completely defined content will also be tethered. For example, Pectinex from Novo Nordisk contains pectintranseliminase, polygalacturonase and pectinesterase, and small amounts of hemicellulases and cellulases.

Example 11

Figure 25:
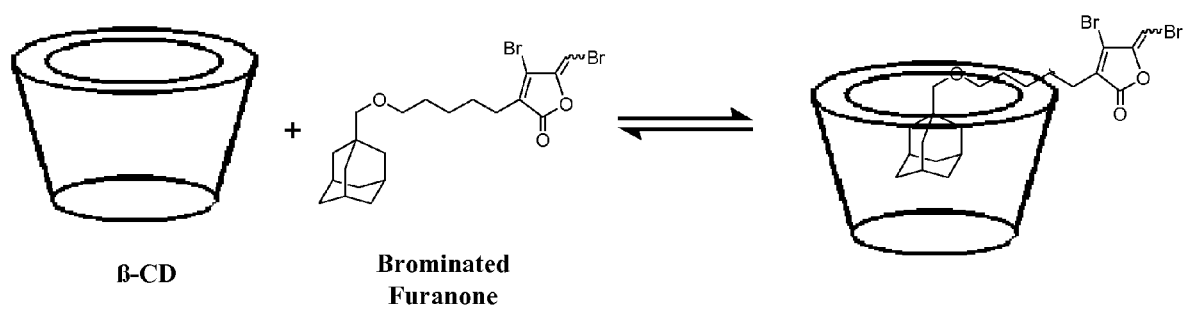
FIG. 25 depicts a reaction scheme relating to the non-covalent immobilization of a brominated furanone.

Use of a Non-Covalently Immobilized Drug on a Hydrogel to Inhibit Biofilm Formation A 3-dimensional porous structure will be built to form a dynamic artificial biointerface to control the formation of biofilm (see FIG. 25). The plan for making this structure integrates three elements: (i) a porous hydrogel structure (pore diameters ~20-40 µm), (ii) the ability to non-covalently encapsulate drugs in the hydrogel materials, and (iii) a mechanism for the hydrogel to be responsive to the stimuli. Drug can be antibiotics. An example of generic structure carrying a drug is as follows:

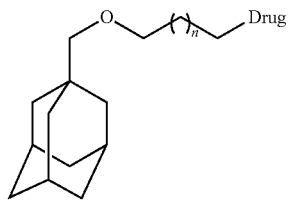

Synthesis of Linear Polyacrylic Polymer Tethering β-Cyclodextrins.

Figure 26:
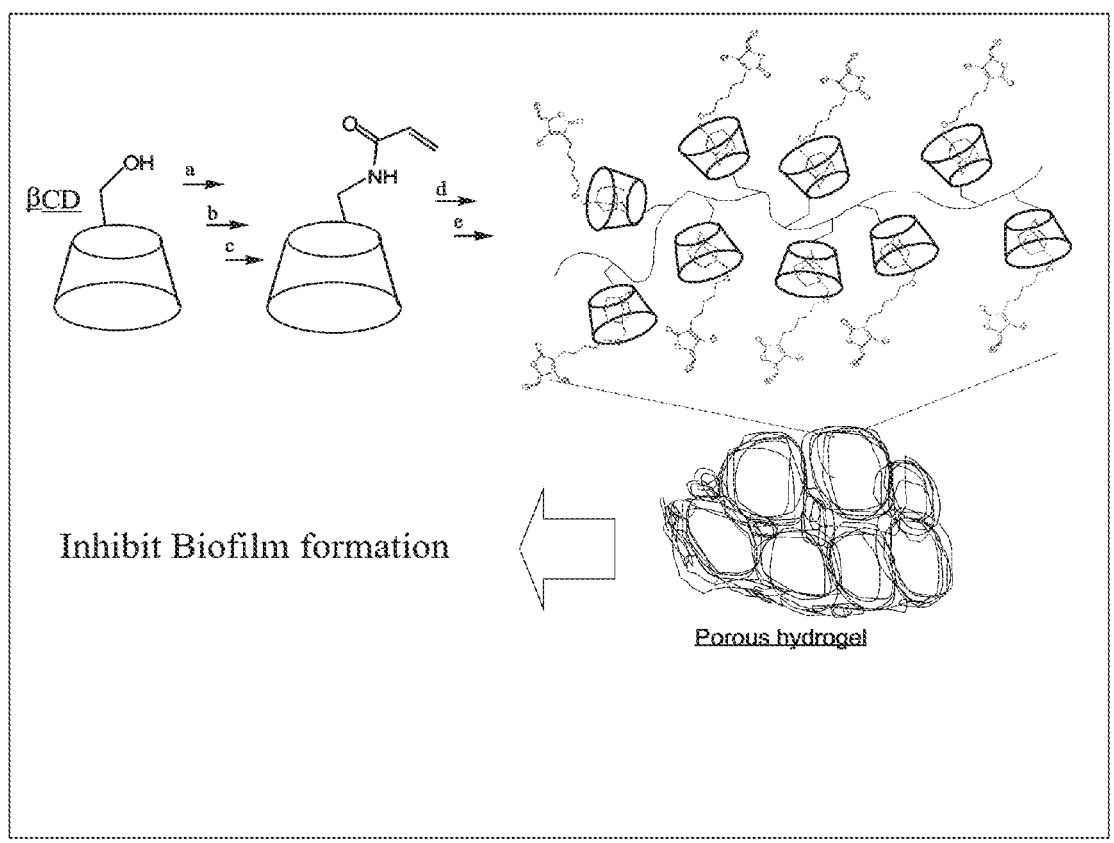
FIG. 26 is a schematic showing the synthesis of CD-tethered hydrogel: a. $Ts_2O/H_2O$, monosubstitution; b. $NH_3$; c. activated acrylic acid; d. radical polymerization in water; e. reversible non-covalent encapsulation of furanones.

The synthesis for modifying β-cyclodextrins (βCD) with amide bonds (Svensson, B., K. S. Bak-Jensen, H. Mori, J. Sauer, M. T. Jensen, B. Kramhoft, T. E. Gottschalk, T. Christensen, B. W. Sigurskjold, N. Aghajari, R. Haser, N. Payre, S. Cottaz, and H. Driguez, The engineering of specificity and stability in selected starch degrading enzymes. Spec. Publ.-R. Soc. Chem., 1999. 246(Recent Advances in Carbohydrate Bioengineering): p. 272-281) readily facilitates the monosubstitution of βCD with a polymerizable acrylic unit (—NH(C=O)CH=CH$_2$) (FIG. 26). This acrylic amide tethered with βCD will be polymerized with other monomers (acrylic amide or polyols) to form linear polymers and hydrogels that can encapsulate furanones through the annular cavity of the cyclodextrin.

Quantification of Furanone Encapsulation by Linear Polymers Tethered with β-Cyclodextrins.

Because brominated furanones are hydrophobic and highly UV-active, induced circular dichroism is a well-suited technique to quantify the amount of furanones encapsulated by βCD in the linear polymer in water. The loading capacity of furanones in hydrogel with and without βCD substitution will also be reported.

Fabrication of Porous Hydrogel Containing βCD.

Non-ionic water-soluble functional groups on polymers have been identified as being suitable for affording stable water-in-water emulsion of DSCG molecules (Luk, Y.-Y., C.-H. Jang, L.-L. Cheng, B. A. Israel, and N. L. Abbott, Influence of lyotropic liquid crystals on the ability of antibodies to bind to surface-immobilized antigens. Chemistry of Materials, 2005. 17(19): p. 4774-4782). Cyclodextrin, possessing multiple hydroxyl groups, is suitable for making the porous hydrogel of the present invention. Also, the synthesis of the brominated furanones of the present invention makes use of a radical reaction to afford the final product. Therefore, both βCD and brominated furanones will be compatible for in situ radical polymerization of water-in-water emulsion to prepare porous hydrogels loaded with brominated furanones through βCD.

Reloading of Drug Materials.

For mature biofilms, the potency of inhibitor becomes significantly reduced. However, the porosity of interface may allow the transport of drugs from underneath the formed biofilm through diffusion. This diffusion is deemed impossible or extremely difficult on non-porous surfaces. By applying brominated furanones to the formed biofilm on porous hydrogel, one can evaluate the changes in the biofilm.

Example 12

Modification of Surfaces Using a Hydrogel

Figure 27:
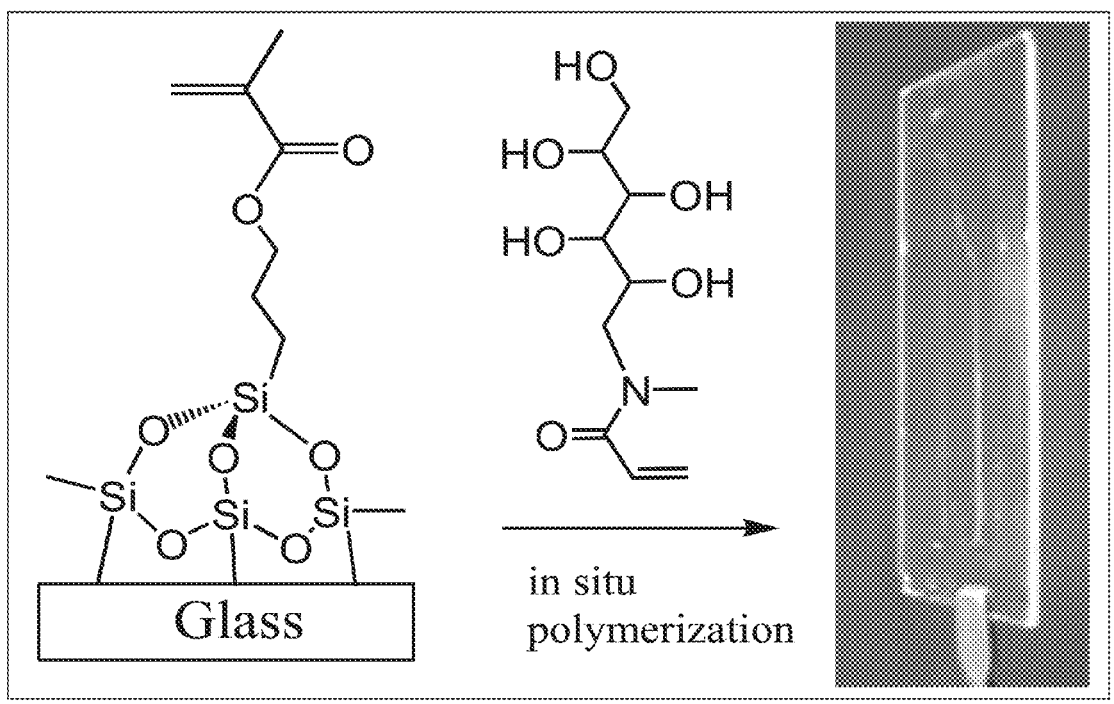
FIG. 27 illustrates the grafting of hydrogels on glass slides.

The chemistry for grafting hydrogels can be readily developed for many surfaces, for example, by incorporating the immobilization chemistry of monolayers. FIG. 27 demonstrates a thin layer (~13 μm) of hydrogel grafted on glass substrate by in situ polymerization of a polyol derivatized acrylamide on glass slide modified with acrylic groups.

Applicability of this Interfacial Approach.

Figure 28:
FIG. 28 is a schematic showing enzymatic degradation of polysaccharides by porous hydrogel polysaccharide. Porous hydrogel is loaded with enzymes.

Although biofouling is different on different surface materials, this multifunctional interface is broadly applicable to many surfaces, because once the hydrogel is immobilized on a surface, the supporting surface material becomes quite irrelevant. The requirement of an otherwise structured monolayer to support the bio-inert surface chemistry is also eliminated. Because many hydrogel materials are non-toxic and are already used in biomedical research, this approach of constructing a 3-dimensional porous structure loaded with active protein at interface also has the potential for use in living systems (see FIG. 28). For instance, by coating a medical implant with a thin layer of nontoxic porous hydrogel loaded with active proteinase, the undesired immuno-resistance can be reduced by degrading the protein adsorption on the surface of the implant.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

What is claimed is:

1. A non-amphiphile-based hydrogel composition comprising:
   a plurality of liquid crystal droplets, each of which comprises a non-amphiphilic lyotropic mesogen;
   a water soluble polymer comprising a polymerized monomer that is covalently coupled to a protein that surrounds each of said liquid crystal droplets and forms a contact surface therebetween to define a hydrogel having a plurality of pores at each of said liquid crystal droplets, wherein said protein is selectively immobilized at said contact surface between said polymer and each of said liquid crystal droplets; and
   water.

2. The composition according to claim 1, wherein said water-soluble polymer and non-amphiphilic lyotropic mesogen are present in amounts selected from the group consisting of: (a) the water-soluble polymer is present in an amount of about 1 wt. % to about 30 wt. %, and the non-amphiphilic lyotropic mesogen is present in an amount of about 2 wt. % to about 20 wt. %; (b) the water-soluble polymer is present in an amount of about 6 wt. % to about 8 wt. %, and the non-amphiphilic lyotropic mesogen is present in an amount of about 8 wt. % to about 10 wt. %; and (c) the water-soluble polymer is present in an amount of about 5 wt. % to about 8 wt. %, and the non-amphiphilic lyotropic mesogen is present in an amount of about 5 wt. % to about 8 wt. %.

3. The composition according to claim 1, wherein said non-amphiphilic lyotropic mesogen comprises a lyotropic chromonic liquid crystal.

4. The composition according to claim 3, wherein said lyotropic chromonic liquid crystal comprises disodium cromoglycate (DSCG).

5. The composition according to claim 4, wherein said DSCG is present in an amount of about 3 wt. % to about 20 wt. %, based on the total weight of said DSCG and said water-soluble polymer.

6. The composition according to claim 1, wherein said water-soluble polymer includes a functional group selected from the group consisting of a hydroxyl group, an amide group, and a pyrrolidone group.

7. The composition according to claim 1, wherein said water-soluble polymer is selected from the group consisting of a polyacrylamide, a polyol, a polyvinylpyrrolidone, a polysaccharide, and water-soluble fluoride-bearing polymer.

8. The composition according to claim 7, wherein said polyacrylamide is poly(N-isopropylacrylamide).

9. The composition according to claim 1, wherein said water-soluble polymer is crosslinked.

10. The composition according to claim 1, wherein said protein comprises an enzyme.

11. The composition according to claim 10, wherein said enzyme is selected from the group consisting of a horseradish peroxidase, an amylase, an aldolase, a lyase, a lipase, a protease, a nitrilase, an amino acylase, an amidase deaminase, an amino acid transaminase, a dehydrogenase, an amino acid oxidase, an amine transaminase, a hydroxy oxidase, a ketoreductase, an ene reductase, and combinations thereof.

12. The composition according to claim 1, wherein said protein comprises a polymerizable vinyl group.

13. A porous hydrogel composition comprising a cross-linked water-soluble polymer network containing a plurality of pores having an interior surface, wherein the pores are comprised of a cross-linked water-soluble polymer having a polymerized monomer that is covalently coupled to a protein that surrounds a liquid crystal droplet, each of which comprise a non-amphiphilic lyotropic mesogen, and said protein is selectively immobilized on the interior surface between the polymer and the liquid crystal droplets.

14. The hydrogel composition according to claim 13, wherein the pores comprise interconnected pores, non-interconnected pores, or a combination of interconnected and non-interconnected pores.

15. The hydrogel composition according to claim 13, wherein said plurality of pores have an average pore diameter of about 5 µm to about 40 µm.

16. The hydrogel composition according to claim 13 further comprising a biocatalytic compound, wherein said biocatalytic compound is either covalently or non-covalently immobilized.

17. The hydrogel composition according to claim 16, wherein the biocatalytic compound is effective for inhibiting the formation of biofilm.

18. The hydrogel composition according to claim 16, wherein the biocatalytic compound is a protein selected from the group consisting of an antigen, an antibody, and an enzyme.

19. The hydrogel composition according to claim 18, wherein the enzyme is effective for degrading a polysaccharide in solution.

20. The hydrogel composition according to claim 18, wherein said enzyme is selected from the group consisting of a horseradish peroxidase, an amylase, an aldolase, a lyase, a lipase, a protease, a nitrilase, an amino acylase, an amidase deaminase, an amino acid transaminase, a dehydrogenase, an amino acid oxidase, an amine transaminase, a hydroxy oxidase, a ketoreductase, an ene reductase, and combinations thereof.

21. A three-dimensional cell culture having a scaffold comprised of the hydrogel composition according to claim 13.

22. A substrate comprising a layer formed on the substrate, wherein said layer comprises the hydrogel composition according to claim 13.

* * * * *